(12) United States Patent
Forbes et al.

(10) Patent No.: US 11,285,174 B2
(45) Date of Patent: Mar. 29, 2022

(54) MACROPHAGE-BASED THERAPY FOR USE IN THE TREATMENT OF LIVER INJURY

(71) Applicant: THE UNIVERSITY COURT OF THE UNIVERSITY OF EDINBURGH, Edinburgh (GB)

(72) Inventors: Stuart Forbes, Edinburgh (GB); Philip Starkey Lewis, Edinburgh (GB); Lesley Forrester, Edinburgh (GB)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 351 days.

(21) Appl. No.: 16/331,787

(22) PCT Filed: Sep. 18, 2017

(86) PCT No.: PCT/GB2017/052769
§ 371 (c)(1),
(2) Date: Mar. 8, 2019

(87) PCT Pub. No.: WO2018/051136
PCT Pub. Date: Mar. 22, 2018

(65) Prior Publication Data
US 2019/0240256 A1    Aug. 8, 2019

(30) Foreign Application Priority Data

Sep. 19, 2016  (GB) ..................................... 1615923
May 5, 2017    (GB) ..................................... 1707183

(51) Int. Cl.
| | | |
|---|---|---|
| A61K 35/15 | (2015.01) | |
| A61P 1/16 | (2006.01) | |
| A61P 1/00 | (2006.01) | |
| A61K 9/00 | (2006.01) | |
| A61K 31/167 | (2006.01) | |
| C12N 5/0735 | (2010.01) | |
| C12N 5/074 | (2010.01) | |

(52) U.S. Cl.
CPC ............ *A61K 35/15* (2013.01); *A61K 9/0019* (2013.01); *A61K 31/167* (2013.01); *A61P 1/00* (2018.01); *A61P 1/16* (2018.01); *C12N 5/0606* (2013.01); *C12N 5/0696* (2013.01); *C12N 2501/22* (2013.01); *C12N 2501/2304* (2013.01); *C12N 2501/2313* (2013.01)

(58) Field of Classification Search
CPC ...................................................... A61K 35/15
See application file for complete search history.

(56) References Cited

FOREIGN PATENT DOCUMENTS

| CN | 103977029 | | 8/2014 |
|---|---|---|---|
| CN | 103977029 A | * | 8/2014 |
| WO | 2016114723 A1 | | 7/2016 |

OTHER PUBLICATIONS

Gordon Siamon et al "Alternative activation of macrophages: mechanism and functions" Immunity, 32(5):593-604 (2010).
Gordon Siamon "Alternative activation of macrophages" The Journal of Immunology, 3(1):23-35 (2003) Abstract.
Holt Michael et al "Identification and characterization of infiltrating macrophages in acetaminophen-induced liver injury" Journal of Leukocyte Biology, 84: 1410-1421 (2008).
Murray Peter et al, "Macrophage Activation and Polarization: Nomenclature and Experimental Guidelines", Immunity, 41(1):14-20 (2014).
Nishida et al, "Adoptive transfer of macrophages ameliorates renal fibrosis in mice" Biochemical and Biophysical Research Communications, 332(1):11-16 (2005) Abstract.
Notification of Transmittal and International Search Report and Written Opinion corresponding to International Patent Application No. PCT/GB2017/052769, dated Jan. 19, 2018, 18 pages.
Sica Antonio et al, "Macrophage plasticity and polarization: in vivo veritas" Journal of Clinical Investigation, 122(3):787-795 (2012).
Tacke Frank et al "Macrophage heterogeneity in liver injury and fibrosis", Journal of Hepatology, 60(5):1090-1096 (2014).
Thomas James et al, "Macrophage Therapy for Murine Liver Fibrosis Recruits Host Effector Cells Improving Fibrosis, Regeneration, and Function" Hepatology, 53(6):2003-2015 (2011).
Zhuang Lihui et al, "Pure populations of murine macrophages from cultured embryonic stem cells. Application to studies of chemotaxis and apoptotic cell clearance", Journal of Immunological Methods, 385(1):1-14 (2012) Abstract only.
International Preliminary Report on Patentability corresponding to International Patent Application No. PCT/GB2017/052769, dated Mar. 28, 2019, 9 pages.

* cited by examiner

*Primary Examiner* — Daniel C Gamett
(74) *Attorney, Agent, or Firm* — Myers Bigel, P.A.

(57) ABSTRACT

The present invention relates to alternatively activated macrophages (AAMs) for use in the treatment of liver injury and methods of treating and preventing liver injury using AAMs.

11 Claims, 43 Drawing Sheets

Specification includes a Sequence Listing.

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: iNOS forward primer

<400> SEQUENCE: 1
aacacccggg acatgagac                                                19

<210> SEQ ID NO 2
<211> LENGTH: 20
<212> TYPE: DNA
<213> ORGANISM: Artificial Sequence
<220> FEATURE:
<223> OTHER INFORMATION: iNOS reverse primer

<400> SEQUENCE: 2
cctgggagga tcaggaagtc                                               20

<210> SEQ ID NO 3
<211> LENGTH: 19
<212> TYPE: DNA
<213> ORGANISM: Artificial Sequence
<220> FEATURE:
<223> OTHER INFORMATION: CD86 forward primer

<400> SEQUENCE: 3
gaagccgaat cagcctagc                                                19

<210> SEQ ID NO 4
<211> LENGTH: 20
<212> TYPE: DNA
<213> ORGANISM: Artificial Sequence
<220> FEATURE:
<223> OTHER INFORMATION: CD86 reverse primer

<400> SEQUENCE: 4
cagcgttact atcccgctct                                               20

<210> SEQ ID NO 5
<211> LENGTH: 18
<212> TYPE: DNA
<213> ORGANISM: Artificial Sequence
<220> FEATURE:

```
<223> OTHER INFORMATION: ARG1 forward primer

<400> SEQUENCE: 5
gaatctgcat gggcaacc                                                    18

<210> SEQ ID NO 6
<211> LENGTH: 22
<212> TYPE: DNA
<213> ORGANISM: Artificial Sequence
<220> FEATURE:
<223> OTHER INFORMATION: ARG1 reverse primer

<400> SEQUENCE: 6
gaatcctggt acatctggga ac                                               22

<210> SEQ ID NO 7
<211> LENGTH: 20
<212> TYPE: DNA
<213> ORGANISM: Artificial Sequence
<220> FEATURE:
<223> OTHER INFORMATION: FIZZ1 forward primer

<400> SEQUENCE: 7
tatgaacaga tgggcctcct                                                  20

<210> SEQ ID NO 8
<211> LENGTH: 21
<212> TYPE: DNA
<213> ORGANISM: Artificial Sequence
<220> FEATURE:
<223> OTHER INFORMATION: FIZZ1 reverse primer

<400> SEQUENCE: 8
aggcagttgc aagtatctcc a                                                21

<210> SEQ ID NO 9
<211> LENGTH: 19
<212> TYPE: DNA
<213> ORGANISM: Artificial Sequence
<220> FEATURE:
<223> OTHER INFORMATION: TWEAK forward primer

<400> SEQUENCE: 9
caggatggag cacaagcag                                                   19

<210> SEQ ID NO 10
<211> LENGTH: 20
<212> TYPE: DNA
<213> ORGANISM: Artificial Sequence
<220> FEATURE:
<223> OTHER INFORMATION: TWEAK reverse primer

<400> SEQUENCE: 10
ggctggagct gttgattttg                                                  20

<210> SEQ ID NO 11
<211> LENGTH: 19
<212> TYPE: DNA
<213> ORGANISM: Artificial Sequence
<220> FEATURE:
<223> OTHER INFORMATION: MMP9 forward primer

<400> SEQUENCE: 11
acgacataga cggcatcca                                                   19
```

<210> SEQ ID NO 12
<211> LENGTH: 20
<212> TYPE: DNA
<213> ORGANISM: Artificial Sequence
<220> FEATURE:
<223> OTHER INFORMATION: MMP9 reverse primer

<400> SEQUENCE: 12
gctgtggttc agttgtggtg                                        20

<210> SEQ ID NO 13
<211> LENGTH: 19
<212> TYPE: DNA
<213> ORGANISM: Artificial Sequence
<220> FEATURE:
<223> OTHER INFORMATION: MMP12 forward primer

<400> SEQUENCE: 13
gctgctccca tgaatgaca                                         19

<210> SEQ ID NO 14
<211> LENGTH: 20
<212> TYPE: DNA
<213> ORGANISM: Artificial Sequence
<220> FEATURE:
<223> OTHER INFORMATION: MMP12 reverse primer

<400> SEQUENCE: 14
aagcattgca cacggttgta                                        20

<210> SEQ ID NO 15
<211> LENGTH: 19
<212> TYPE: DNA
<213> ORGANISM: Artificial Sequence
<220> FEATURE:
<223> OTHER INFORMATION: MMP13 forward primer

<400> SEQUENCE: 15
gccagaactt cccaaccat                                         19

<210> SEQ ID NO 16
<211> LENGTH: 21
<212> TYPE: DNA
<213> ORGANISM: Artificial Sequence
<220> FEATURE:
<223> OTHER INFORMATION: MMP13 reverse primer

<400> SEQUENCE: 16
tcagagccca gaattttctc c                                      21

<210> SEQ ID NO 17
<211> LENGTH: 20
<212> TYPE: DNA
<213> ORGANISM: Artificial Sequence
<220> FEATURE:
<223> OTHER INFORMATION: CD40 forward primer

<400> SEQUENCE: 17
gccaagaagc caaccaataa                                        20

<210> SEQ ID NO 18
<211> LENGTH: 21
<212> TYPE: DNA
<213> ORGANISM: Artificial Sequence
<220> FEATURE:
<223> OTHER INFORMATION: CD40 reverse primer

```
<400> SEQUENCE: 18
tggcatccat gtaaagtctc c                                             21

<210> SEQ ID NO 19
<211> LENGTH: 20
<212> TYPE: DNA
<213> ORGANISM: Artificial Sequence
<220> FEATURE:
<223> OTHER INFORMATION: CD80 forward primer

<400> SEQUENCE: 19
aagcaagggg ctgaaaagat                                               20

<210> SEQ ID NO 20
<211> LENGTH: 19
<212> TYPE: DNA
<213> ORGANISM: Artificial Sequence
<220> FEATURE:
<223> OTHER INFORMATION: CD80 reverse primer

<400> SEQUENCE: 20
aagggcaagg tggggtaat                                                19

<210> SEQ ID NO 21
<211> LENGTH: 20
<212> TYPE: DNA
<213> ORGANISM: Artificial Sequence
<220> FEATURE:
<223> OTHER INFORMATION: TGM2 forward primer

<400> SEQUENCE: 21
tcaccttcag tgtcgtgacc                                               20

<210> SEQ ID NO 22
<211> LENGTH: 22
<212> TYPE: DNA
<213> ORGANISM: Artificial Sequence
<220> FEATURE:
<223> OTHER INFORMATION: TGM2 reverse primer

<400> SEQUENCE: 22
cagcatctct tagtggaaaa cg                                            22

<210> SEQ ID NO 23
<211> LENGTH: 20
<212> TYPE: DNA
<213> ORGANISM: Artificial Sequence
<220> FEATURE:
<223> OTHER INFORMATION: MRC1 forward primer

<400> SEQUENCE: 23
tgttttggtt gggattgaca                                               20

<210> SEQ ID NO 24
<211> LENGTH: 21
<212> TYPE: DNA
<213> ORGANISM: Artificial Sequence
<220> FEATURE:
<223> OTHER INFORMATION: MRC1 reverse primer

<400> SEQUENCE: 24
tctccataag cccagttttc a                                             21
```

MACROPHAGE-BASED THERAPY FOR USE IN THE TREATMENT OF LIVER INJURY

STATEMENT OF PRIORITY

This application is a 35 U.S.C. § 371 national phase application of International Application Serial No. PCT/GB: 2017/052769, filed Sep. 18, 2017, which claims the benefit, of United Kingdom Patent Application No. 1615923.8, filed Sep. 19, 2016, and which claims the benefit, of United Kingdom Patent Application No. 1707183.8, filed May 5, 2017, the entire contents of each of which are incorporated by reference herein.

BACKGROUND

Acetaminophen (paracetamol, APAP) overdose is a common cause of acute liver injury (ALI) in the clinic and is the leading cause of acute liver failure (ALF) in the United States (1-5). APAP also serves as a paradigm hepatotoxin for pre-clinical studies and the molecular mechanisms that underpin APAP hepatotoxicity are now well understood, accounting for at least four decades of research. However, in the clinic, the therapeutic management of APAP-induced ALI is primarily limited to n-acetyl cysteine (NAC) therapy which serves as an effective antidote early after drug ingestion (typically within 10 hours). However, the effectiveness of NAC therapy is substantially diminished in patients who present late after APAP ingestion (i.e. longer than 10 hours) (6). Treatment for late-presenting patients is largely centred on supportive care, and liver transplantation may be required in patients who subsequently develop ALF. Due to the shortages of suitable organ donors and associated life-long immunosuppression required, liver-transplantation is clearly not an ideal therapeutic intervention. Therefore, novel therapies that are applicable to patients who present late with APAP poisoning are urgently sought.

APAP poisoning is characterised by rapid onset necrosis of centrilobular hepatocytes in the liver. Without immediate clinical intervention, substantial liver injury can progress into liver failure associated with a sepsis-like response known as systemic inflammatory response syndrome (SIRS) typically characterised by immune activation, encephalopathy, hypothermia, and a high risk of multi-organ failure and death (7). Recent work has shown that tissue resident macrophages (Kupffer Cells, KCs) that serve to maintain the hepatic innate immunity become depleted early after APAP challenge which leads to an immunological deficit in the liver during injury (8). Macrophages are thought to stimulate ductular cells to proliferate through the secretion of TNF-related weak inducer of apoptosis (TWEAK) (Bird, T. G. et al. Bone marrow injection stimulates hepatic ductular reactions in the absence of injury via macrophage-mediated TWEAK signaling. *Proc Natl Acad Sci USA* 110, 6542-6547, doi:10.1073/pnas.1302168110 (2013); Jakubowski, A. et al. TWEAK induces liver progenitor cell proliferation. *J Clin 548 Invest* 115, 2330-2340, doi:10.1172/jci23486 (2005)). Whilst these ductular cells may be associated with fibrosis (Williams, M. J., Clouston, A. D. & Forbes, S. J. Links between hepatic fibrosis, ductular reaction, and progenitor cell expansion. *Gastroenterology* 146, 349-356, doi: 10.1053/j.gastro.2013.11.034 (2014)) they may also contain regenerative hepatic progenitor cells (HPC) (Lu, W. Y. et al. Hepatic progenitor cells of biliary origin with liver repopulation capacity. *Nat Cell Biol* 17, 971-983, doi:10.1038/ncb3203 (2015)). KCs also provide an immunological barrier from gut-derived pathogens which become dysregulated during liver injury further risking systemic toxicity (9, 10). There are further systemic immunological effects which lead to a depletion and dysfunction of circulating monocytes which are recruited to the liver in a CCR2-dependent manner (11-13). A conflicting literature exists pertaining to the role of macrophages during liver injury which likely reflects the complex and plastic nature of macrophage biology during tissue injury and regeneration.

Stem cells in a healthy liver have an enormous capacity for regeneration but chronic injury induced by viral infection, alcohol abuse, exposure to toxins and metabolic disorders leads to fibrotic scaring, cirrhosis and the ultimate failure of that regenerative process (Friedman, S. L. Mechanisms of hepatic fibrogenesis. *Gastroenterology* 134, 1655-1669, doi:10.1053/j.gastro.2008.03.003 (2008)).

The only treatment available is organ transplantation but with increasing demand and a limited number of donors, there is an urgent requirement for alternative therapies (Soltys, K. A. et al. Barriers to the successful treatment of liver disease by hepatocyte transplantation. *J Hepatol* 53, 769-774, doi:10.1016/j.jhep.2010.05.010 (2010)).

Novel therapies which can be used in the treatment of liver injury are urgently sought. It is an objection of the invention to provide novel therapies for the liver injury. Advantageously, such therapies would be able to accelerate the resolution of liver necrosis, suppress the system inflammatory response and promote liver regeneration.

BRIEF SUMMARY OF THE DISCLOSURE

In accordance with the present invention there is provided alternatively-activated macrophages (AAMs) for use in the prevention or treatment of liver injury, such as a chronic or acute liver injury.

Suitably, the livery injury may be an acute liver injury, such as a liver injury associated with the use of a drug or an overdose of a drug. Suitably, the liver injury may result from the use of one or more drugs selected from the group consisting of: acetaminophen, clarithromycin, statins, nicotinic acid, amiodarone, methotrexate, isoniazid, nitrofurantoin, augmentin, aspirin, indomethacin, ibuprofen, naproxen, piroxicam, nabumetone, diclofenac, tacrine or disulfiram. Suitably, the drug may be acetaminophen. Suitably, the liver injury may result from poisoning, such as mushroom poisoning.

Suitably, the AAMs may be administered when the liver is showing signs of necrosis. Suitably, the AAMs may be administered 10 hours or more following poisoning or drug overdose.

Alternatively-activated (M2-like) macrophages may be prepared by polarising macrophages with IL-4, IL-13, CSF-1 or a combination thereof. Suitably, bone-marrow derived macrophages (BMDMs) may be polarised with IL-4 and IL-13. Advantageously, the alternatively-activated macrophages may be prepared from a macrophage sample from a subject to be treated such that the AAMs are autologous to the subject having a liver injury.

Suitably, the alternatively-activated macrophages may be derived from pluripotent cells, such as induced pluripotent stem cells (iPSCs) or embryonic stem cells (ES cells).

Suitably, the alternatively-activated macrophages are formulated for intravenous administration.

Suitably, the alternatively-activated macrophages may be provided at a dose of $10^7$ to $10^9$ cells.

In another aspect, the present invention provides a method of preventing or treating liver injury in a subject, comprising a therapeutically effective amount of alternatively-activated macrophages to said subject.

Suitably, the liver injury may be an acute liver injury, such as a liver injury associated with the use of a drug or an overdose of a drug. Suitably, the liver injury may result from the use of one or more drugs selected from the group consisting of: acetaminophen, clarithromycin, statins, nicotinic acid, amiodarone, methotrexate, isoniazid, nitrofurantoin, augmentin, aspirin, indomethacin, ibuprofen, naproxen, piroxicam, nabumetone, diclofenac, tacrine or disulfiram. Suitably, the drug may be acetaminophen.

Suitably, the AAMs may be administered when the liver is showing signs of necrosis. Suitably, the AAMs may be administered 10 hours or more following poisoning or drug overdose.

Alternatively-activated (M2-like) macrophages may be prepared by polarising macrophages with IL-4, IL-13, CSF-1 or a combination thereof. Suitably, bone-marrow derived macrophages (BMDMs) may be polarised with IL-4 and IL-13. Advantageously, the alternatively-activated macrophages may be prepared from a macrophage sample from a subject to be treated such that the AAMs are autologous to the subject having a liver injury.

Suitably, the alternatively-activated macrophages may be derived from pluripotent cells, such as induced pluripotent stem cells (iPSCs) or embryonic stem cells (ES cells).

Suitably, the administration may be intravenous and/or may be are provided at a dose of $10^7$ to $10^9$ cells.

BRIEF DESCRIPTION OF THE DRAWINGS

Embodiments of the invention are further described hereinafter with reference to the accompanying drawings, in which.

DETAILED DESCRIPTION

Figure 1:
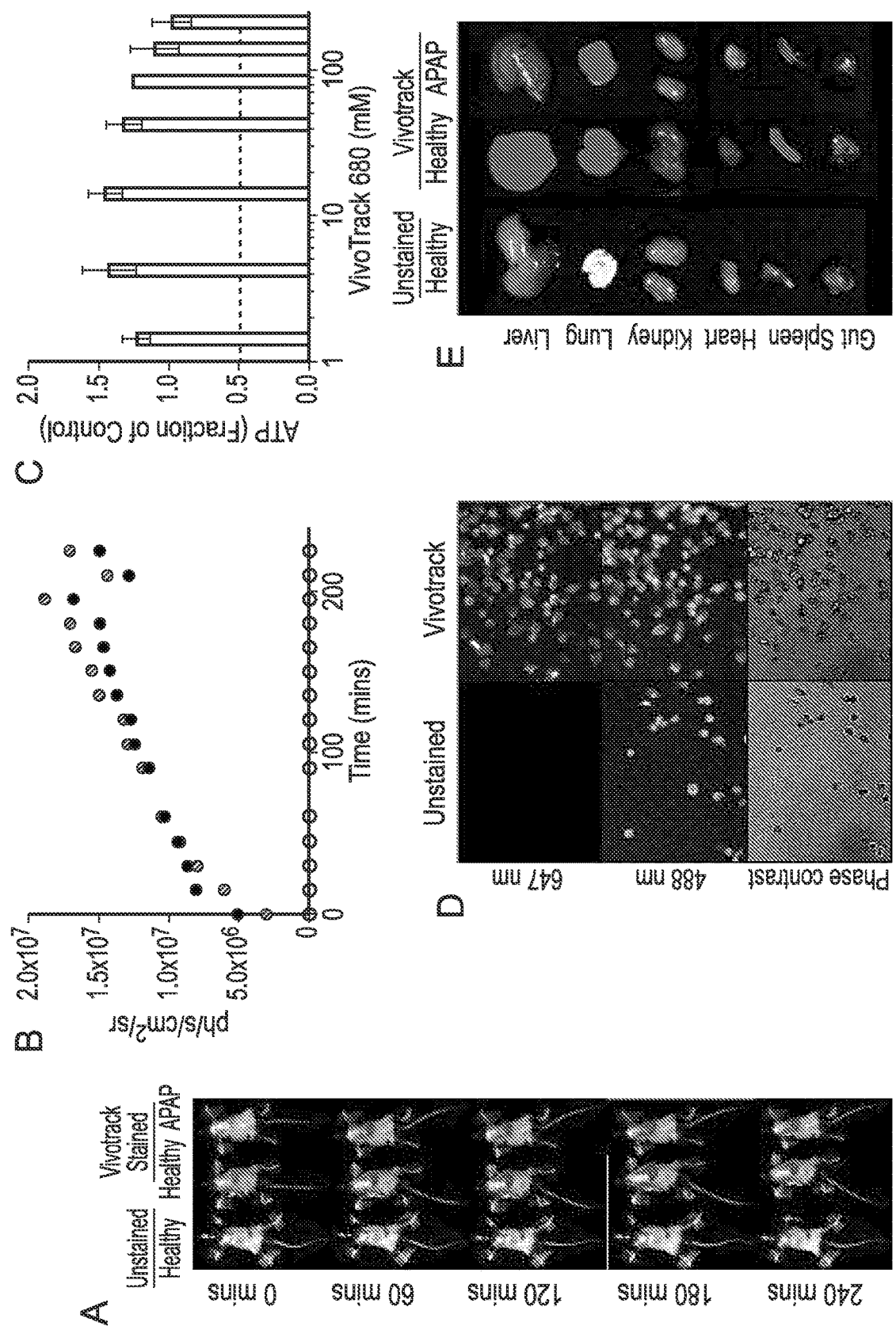
FIG. 1 shows BMDMs administered intravenously rapidly engraft in liver and spleen. (A) Infrared fluorescent optical imaging shows Vivotrack-labelled BMDMs ($5 \times 10^6$, i.v.) accumulating in the upper abdomen within 4 hrs in healthy and APAP-poisoned mice (B) Quantification of the fluorescent signal from an abdominal ROI measured every 15 mins shows accumulation up to 4 hrs. Open circles represent mice receiving unstained BMDMs and closed circles represent mice receiving Vivotrack-stained BMDMs (black circles, healthy; red circles, APAP-poisoned). (C) BMDMs tolerate Vivotrack as shown by cellular ATP levels post-labelling. (D) Fluorescent microscopy shows strong uniform staining of GFP-positive BMDMs post-labelling but not in unlabelled BMDMs (E) Ex vivo imaging of organs show BMDM localisation in liver, lung, and spleen at 4 hours post-transplant (i.v.) in healthy and APAP-poisoned mice. (F) Organ by organ fluorescence quantification shows BMDM localisation in liver, lung, and spleen in both healthy mice receiving unstained cells (grey bars), and mice receiving stained cells (black bars, healthy; red bars, APAP-poisoned). The fluorescent signal appears 70% less in the liver of APAP-poisoned mice versus healthy equivalents suggesting less hepatic engraftment in injured liver. (G) Immunohistochemical 3,3'-Diaminobenzidine (DAB)-staining against fluorescein isothiocyanate (FITC) in CFSE-stained macrophages shows positive staining in cells with typical macrophage morphology in liver and spleen parenchyma (black arrows). BMDMs appear within and around necrotic areas in the liver (identified with strong background staining around the central vein (CV); left image middle row). No BMDMs were detected in kidney, lung, or brain tissue. Bar graphs in panels show the mean value around the standard deviation.
Figure 1:
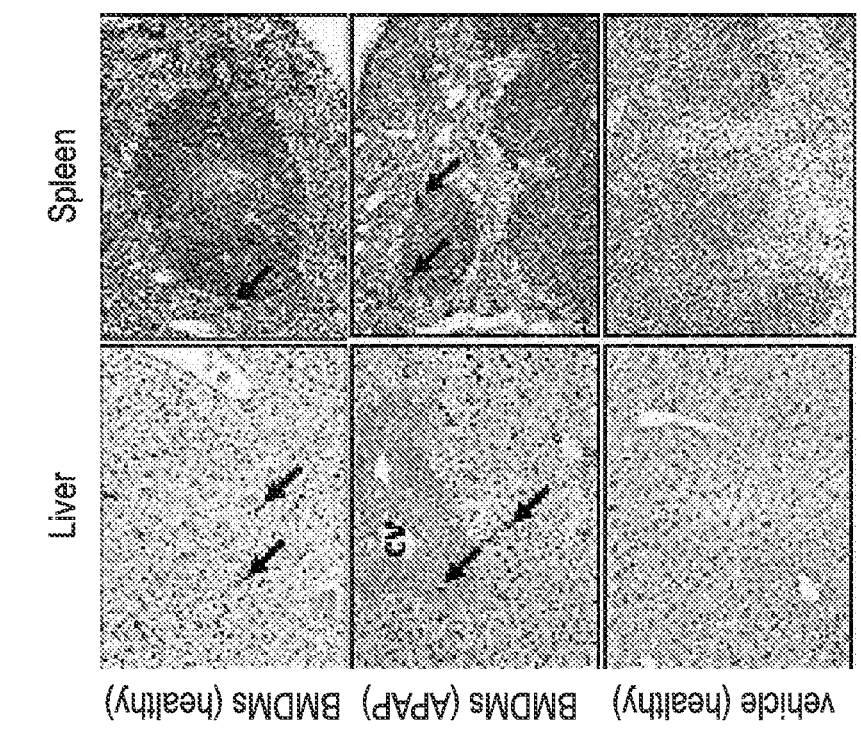
Figure 1:
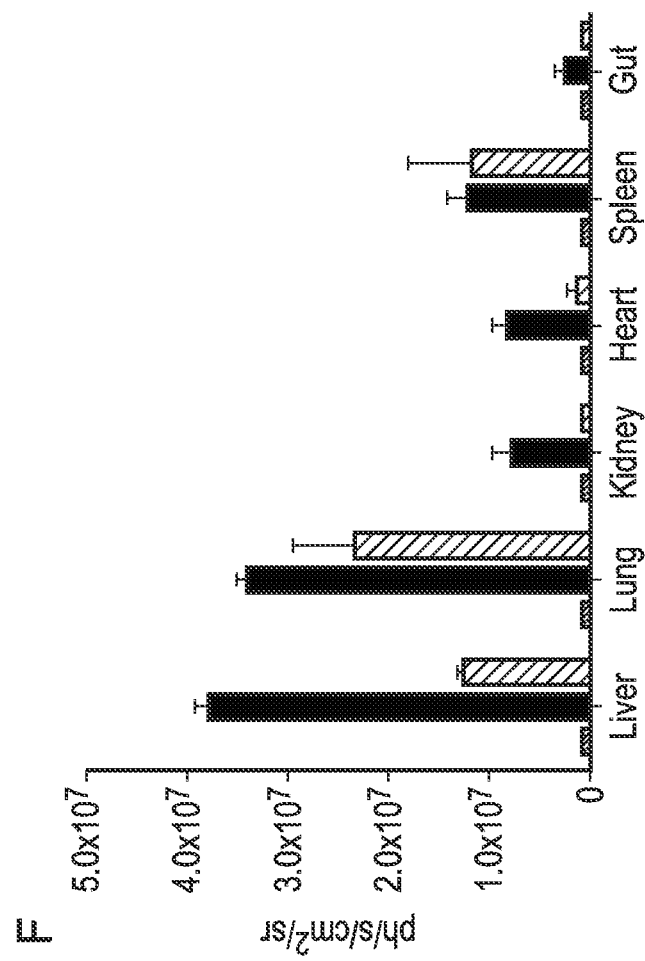

The present inventors have surprisingly found that alternatively-activated macrophages (AAMs) have particular utility in the treatment of injuries to the liver. Surprisingly, administration of AAMs may result in one or more of the following advantageous effects: a reduction in necrosis, an increase in liver cell proliferation, a reduction of levels of pro-inflammatory cytokines, an increase is phagocytosis at the injury site and a reduction in the proportion of endogenous inflammatory infiltrating macrophages. Accordingly, AAM therapy may advantageously: accelerate the resolution of hepatitis necrosis, suppress the system inflammatory response, reduce hepatic fibrosis, reduce hepatic scaring and/or promote liver regeneration.

Haematopoietic cells derived from ESCs in vitro are thought to be more closely related to blood cells associated with the primitive wave of haematopoiesis in the yolk sac during development (Zambidis, E. T., Peault, B., Park, T. S., Bunz, F. & Civin, C. I. in Blood Vol. 106 860-870 (2005)). Tissue resident macrophages are known to be derived from the primitive wave of haematopoiesis, well before the appearance of haematopoietic stem cells (HSC) in the embryo and develop in the absence of Myb (Schulz, C. et al. A lineage of myeloid cells independent of Myb and hematopoietic stem cells. Science 336, 86-90, doi:10.1126/science.1219179 (2012)). Suitably, the macrophages described herein may be tissue-resident-like-macrophages. Alternatively, the macrophages described herein may be monocyte-derived-like-macrophages. Tissue-resident-like-macrophages may be characterised by having lower levels of expression of Myb and Ccr2 and higher expression of Pu.1.

Alternatively-activated (M2-like) macrophages are known in the art and may be prepared by polarising bone-marrow derived macrophages with T helper 2 (th2) cytokines interleukin-4 (IL-4) and IL-13. For example, AAMs are detailed in Gordon et al. Immunity 32, May 28, 201, pages 593-604. Advantageously, the AAMs may be produced from macrophages as described in the Examples of the present invention.

AAMs may be characterised by their high expression of Chil3 (Ym1), Retnla (Fizz), Mrc1 (Mannose Receptor 1), and Arg1 (Arginase).

"liver injury", as used herein, refers to hepatotoxicity. Merely by way of example, liver injury is incurred by the subject as a result of autoimmune hepatitis, primary graft non-function, small-for-size syndrome, malignancy and/or drug-induced liver injury. Suitably, drug-induced liver injury may be the result the use of one or more drugs selected from the list consisting of: clarithromycin, statins, nicotinic acid, amiodarone, methotrexate, isoniazid, nitrofurantoin, augmentin, aspirin, indomethacin, ibuprofen, naproxen, piroxicam, nabumetone, diclofenac, tacrine or disulfiram. More suitably, drug-induced liver injury is as a result of acetaminophen overdose.

Long term damage to the liver can lead to chronic liver injury. Merely by way of example, chronic liver injury can be caused viral hepatitis, alcohol, obesity and metabolic disorders. Chronic liver injury may result in fibrosis, hepatic scarring and cirrhosis, which are characterised by the replacement of normal liver tissue by scar tissue. The invention has surprisingly discovered that administered ESDMs significantly reduced the amount of hepatic fibrosis, down-regulated the number of fibrogenic myofibroblasts and activated liver progenitor cells (particularly PanCK+ ductular cells) in vivo. Moreover, it has been surprisingly found that ESDMs can repopulate depleted Kupffer cell compartments. Without wishing to be bound by theory, it is believed that ESDMs may secrete matrix metalloproteinases (MMPs) that break down extracellular matrix (ECM) components of scar tissue. Suitably, ESDMs polarised to a M2-like macrophage may also have utility in the treatment of a chronic liver injury.

The present invention has also surprisingly found that macrophages primed in culture to an AAM phenotype retain this anti-inflammatory phenotype in vivo. This overcomes potential safety concerns that transplanted macrophages could become pro-inflammatory in phenotype and thereby be detrimental to the treatment of injury.

Suitably, AAMs may be administered in the regenerative phase following liver injury. For example, after 16 hours following a drug-induced liver injury. The present invention had shown that administration of AAMs in this phase reduces necrosis. For example, administration of AAMs in the regenerative phase following acetaminophen overdose has been shown in the Examples to reduce centrilobular necrosis by 60% and yield an 8-fold increase in liver cell proliferation as well as reducing the levels of circulating pro-inflammatory cytokines (such as IFN-γ, IL-6, CXCL1 and TNF-α). Thus, AAMs may accelerate the regenerative response.

Without wishing to be bound by theory, it is believed that the AAMs remove necrotic material from the liver due to their highly phagocytic phenotype.

Advantageously, the alternatively-activated macrophages may be prepared from a macrophage sample from a subject to be treated such that the AAMs are autologous to the subject having a liver injury. For example, a macrophage sample may be harvested from the subject, expanded, characterised as AAMs and reinfused.

Suitably, the alternatively-activated macrophages may be derived from human induced pluripotent stem cells. This may be advantageous for liver injury which progresses to acute liver failure quickly, such as acetaminophen poisoning.

Various methods of producing macrophages from pluripotent stem cells such as ES cells and iPSCs are known in the art, see Yeung et al. 2012 ("Conditional-ready mouse embryonic stem cell derived macrophages enable the study of essential genes in macrophage function". Sc. Rep. 2015 Mar 10; 5:8909. doi: 10.1038/srep08908), Zhuang et al. 2012 ("Pure populations of murine macrophages from cultured embryonic stem cells. Application to studies of chemotaxis and apoptotic cell clearance." J Immunol Methods. 2012 Nov. 30; 385(1-2):1-14. doi: 10.1016/j.jim.2012.06.008. Epub 2012 Jun. 18.), Sneju et al. ("Application of iPS cell-derived macrophages to cancer therapy" Oncoimmunology. 2014; 3: e27927), Hale et al. ("Induced Pluripotent Stem Cell Derived Macrophages as a Cellular System to Study Salmonella and Other Pathogens" PLOS, http://dx-.doi.org/10.1371/journal.pone.0124307), Zhang et al. ("Functional Analysis and Transcriptomic Profiling of iPSC-derived Macrophages and Their Application in Modeling Mendelian Disease" Circ Res. 2015 Jun. 19; 117(1):17-28) Mucci et al. ("Murine iPSC-Derived Macrophages as a Tool for Disease Modeling of Hereditary Pulmonary Alveolar Proteinosis due to Csf2rb Deficiency" Stem Cell Reports 2016 Aug. 9; 7(2):292-305.) and van Wigenburt et al., ("Efficient, Long Term Production of Monocyte-Derived Macrophages from Human Pluripotent Stem Cells under Partly-Defined and Fully-Defined Conditions" PLOS ONE 8(8): e71098. doi:10.1371/journal.pone.0071098). Such macrophages can be polarised to AAMs with T helper 2 (th2) cytokines interleukin-4 (IL-4) and IL-13. Polarisation with IL-4/IL-13 may result in dynamic change in gene expression for Chil3 (e.g. up to approx. 100-fold increase vs naïve BMDMs), Retnla (e.g. up to 1000-100000-fold increase), Mrc1 (e.g. up to approx. 10-fold increase), Arg1 (e.g. up to pprox. 100-1000 fold increase).

Suitably, AAMs may derive from ES cells. Accordingly, ES cell derived macrophages (ESDMs) may be generated by culturing the ES cells in the presence of colony stimulating factor-1 (CSF-1) (also known as M-CSF) and IL-3 to form embryoid bodies (EB). Whilst EBs adhere to tissue culture plastic, macrophage progenitor cells are non-adherent and thus are released into the medium. The macrophage progenitor cells may then be harvested at various time points, for example after 10 or 20 days and plated onto non-treated Petri dishes and cultured in the presence of CSF-1 alone. This process can give rise to monocyte-like cells that adhere to the plastic forming a monolayer and mature into ESDM. The maturation of the ES cells into ESDM can be monitored by detecting the presence of mature macrophage specific markers F4/80 (mouse macrophage specific) or 25F9 (human macrophage specific) and CD11 b. Additionally, human macrophages may be characterised by the absence of the monocyte marker CD93. Advantageously, the method described yields a substantially homogenous population of ESDM Alternatively, AAMs may derive from iPSC. Suitably, the method for differentiation of iPSCs to macrophages may involve supplementing culture medium with a cytokine Mix 1 (comprising bone morphogenetic protein (BMP4), vascular endothelial growth factor (VEGF) and stem cell factor (SCF)). Cells may be cut, dislodged, divided and re-cultured in fresh media supplemented with cytokine mix 1. Cells may be cultured in suspension for 3 days with a cytokine top up on Day 2, to form EBs. The EBs may then be transferred to media supplemented with cytokine Mix 2 (comprising M-CSF, IL3, Glutamax, Penicillin/Streptomycin and β-mercaptoethanol). EBs can be maintained in this medium for the remaining duration of the protocol, with spent medium being replaced with fresh medium every 3-4 days. After about 2 weeks, the EBs produced macrophage progenitors in the culture supernatant that were harvested and transferred to medium supplemented with cytokine Mix 3 (M-CSF, Glutamax, Penicillin/Streptomycin) and allowed to mature into iPSC-derived macrophages (iPSC-DM). Macrophage progenitors may continue to be harvested twice a week for approximately 2 months.

Preferably, the iPSC-derived macrophages (iPSC-DM) are from human iPSCs. Alternatively, iPSC-DM may be murine derived.

The resulting ESDMs or iPSC-DM may be subsequently polarised in vitro to adopt either a M1-like phenotype by treatment with LPS and IFNγ. Alternatively, ESDMs or iPSC-DM may be polarised to yield AAM with IL-4. Alternatively, ESDMs may be polarized to yield AAMs with IL-4, IL-13 and CSF-1. M1-like polarised macrophages are also known as classically activated macrophages (CAM). AAM derived from ESDMs may be characterised by their high expression of Chil3 (Ym1), Retnla (Fizz), Mrc1 (Mannose Receptor 1), and Arg1 (Arginase). In contrast, M1-like polarised macrophages (such as ESDM, BMDM or iPSC-DM) may be characterised by a significant increase in NO production and increased gene expression of iNos and Cd86.

The term "subject" as used herein, refers to any individual who may benefit from the treatment of a liver injury. The subject may be a human subject.

The term "treatment" as used herein refers to an intervention which prevents the progression, or reduces partially or completely the clinical symptoms with a liver injury in a subject. Suitably, the treatment may result in an increase in or an acceleration of liver regeneration.

It will be appreciated that a therapeutically effective amount of AAMs will be dependent on various factors including the weight of the subject to be treated. By way of example a therapeutically effective amount may be in the form of a dose of $1 \times 10^7$ to $1 \times 10^9$ AAMs or a therapeutically effective amount may be in the form of a dose of $2 \times 10^7$ to $2 \times 10^9$ AAMs. Specifically, a therapeutically effective amount may be in the form of a dose of $2 \times 10^7$.

Suitably, the AAMs or a pharmaceutical composition comprising AAMs may be provided in a single dose. Though it would be understood that the multiple doses could also be utilised.

Suitably, the AAMs may be comprised in a pharmaceutical composition. For example, the pharmaceutical composition may comprise a therapeutically effective amount of AAMs and a pharmaceutically acceptable carrier.

The "term pharmaceutically acceptable carrier" as used herein refers to any suitable diluent, excipient, or a combination thereof, suitable for administration into a subject. A pharmaceutically acceptable carrier may be an organic or inorganic substance, which facilities the delivery of AAMs to the subject.

In a suitable embodiment, a pharmaceutical composition of the invention may further comprise a pharmaceutically acceptable concentration of salt, buffering agents, and compatible carriers. The compositions may also include antioxidants and/or preservatives. Suitable antioxidants may be selected from the group consisting of: mentioned thiol derivatives (e.g. thioglycerol, cysteine, acetylcysteine, cystine, dithioerythreitol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid. Suitable preservatives may for instance be phenol, chlorobutanol, benzylalcohol, methyl paraben, propyl paraben, benzalkonium chloride and cetylpyridinium chloride.

The pharmaceutical composition of the present invention may be for administration to the subject via any suitable route. A suitable route of administration may be selected from the group consisting of: intravenous injection or infusion. Other methods for administering pharmaceutical compositions will be known to the skilled in the art.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Example 1

Bone Marrow Derived Macrophages

Methods

Mouse BMDMs: Femurs and tibias of C57/BL6 male mice (8-10 week old) were collected in Hanks' Balanced Salt Solution (HBSS, Gibco) containing penicillin/streptomycin (100 U/mL, 100 µg/mL). Bone marrow (BM) was flushed out with DMEM:F12 (1:1) cell culture media (Gibco) supplemented with 10% fetal bovine serum (FBS), 2 mM glutamine, and penicillin/streptomycin (100 U/mL, 100 µg/mL). Mouse BM was centrifuged (400 g, 5 mins) and then resuspended and strained though 100 µm filter, in supplemented DMEM:F12 media (20 mL) containing 20 ng/mL murine recombinant CSF1 (Peprotech). BM suspensions were then transferred to sterile ultra-low attachment flasks (Corning Inc.) and incubated at 37° C., 5% CO2 in a 20 mL volume. Every second day, 10-20% of the media was replaced with fresh media containing 400 ng CSF1. For BM DM polarisation, 24 hours prior to transplantation, cells were polarised with lipopolysaccharide (LPS, 50 ng/mL, Sigma Aldrich) and recombinant murine interferon gamma (IFNγ, 20 ng/mL, Peprotech) in ultra-low attachment flasks to generate classically-activated macrophages (CAMs). For AAMs, BMDMs were polarised with recombinant murine interleukin-4 and interleukin-13 (IL-4/IL-13, 20 ng/mL, Peprotech). For deactivated macrophages (DAMs), BMDMs were stimulated with recombinant murine interleukin-10 (IL-10, 10 ng/mL, Peprotech) for 24 hours.

Human monocyte derived macrophages: Human monocyte derived macrophages (hMDMs) were differentiated from cryopreserved CD14 monocytes essentially as described previously (19). Briefly, cyropreserved stocks were thawed rapidly and diluted in Iscove's Modified Eagle's Medium (IMEM) supplemented with 10% FBS (v/v), 2 mM glutamine, penicillin/streptomycin (500 U/mL, 500 µg/mL), and 100 ng/mL human recombinant CSF1 (Miltenyi) at 2×106 cells/mL in ultra-low attachment flasks (Corning). Cells were differentiated towards macrophages for 7 days with a 10% media change every second day containing 1 µg CSF1. After 7 days, hMDMs were harvested, counted, and plated on CellCarrier plates with human recombinant cytokines (Peprotech, details as above) towards CAMs and AAMs, or left unstimulated (naïve hMDMs). hMDMs were used for phagocytosis assays (see below).

APAP-induced liver injury and BMDM administration: All animal experiments were carried out under procedural and ethical guidelines of the British Home Office and experimental designs were independently reviewed by a veterinarian. Wildtype C57BL6 male mice (10 weeks old) were supplied by Harlan (UK) and allowed to acclimatise for a minimum of two weeks in a clean animal facility. Mice were housed in groups of five/six in open-top cages and synchronised to a 12-hour dark/light cycle with access to food and water ad libitum. Prior to APAP administration, mice were fasted at least 12 hours. Mice received either a single injection (i.p.) of APAP (350 mg/kg) dissolved in warm saline or saline alone. CFSE-stained BMDMs were resuspended in Dulbecco's Phosphate-Buffered Saline (DPBS) and administered (1×106 cells, 100 µL) via tail vein to mice under gaseous isoflurane/oxygen anaesthesia at either 4 hours or 16 hours after APAP administration. One hour before culling, mice were pulsed with 1 mg (i.p.) of 5-Bromo-2'-deoxyuridine (BrdU, Sigma Aldrich) in PBS to label proliferating cells. Mice were humanely culled by asphyxiation in a rising CO2 atmosphere. Whole blood was collected via cardiac puncture and allowed to clot overnight at 4° C. to collect serum. Liver tissue was harvested and the left lateral lobe was separated into two pieces and placed in either a freezing isopentane bath or fixed in methacarn for 24 hours. The remaining liver and other organs were fixed in formalin (4% paraformaldehyde) for 24 hours before paraffin-embedding.

In vivo cell tracking: To confirm hepatic localisation of transplanted cells administered peripherally, we utilised fluorescent imaging. BMDMs were stained in vitro with VivoTrack 680 (near infra-red fluorescent imaging agent, Perkin Elmer) prior to transplantation. BMDMs (5×106) were incubated with reconstituted VivoTrack (2 mL) in 4 mL DPBS and incubated for 15 mins at room temperature in a dark environment and subsequently washed twice to remove excess dye. Imaging was performed on healthy (DPBS-treated, i.p.) or APAP-treated mice at 16 hours. Mice were anaesthetised and maintained with gaseous oxygen/isofluorane and fur clipped before longitudinal fluorescent images were taken in the dorsal position at 15 min intervals at 687 nm excitation and 722 nm emission (background correction at 487 nm) using a PhotonIMAGER™ (Biospace Lab) imaging suite. After 5 hours mice were humanely culled and organs imaged ex vivo to confirm AAM localisation. In some experiments, BMDMs differentiated from constitutively expressing GFP mice (20) were used to confirm staining with Vivotrack 680 in vitro.

CFSE staining: BMDMs were stained with CellTrace CFSE (ThermoFisher) essentially following the manufacturer's instructions. Briefly, BMDMs were resuspended in DPBS at 1×107 cells/mL and incubated with CFSE at a final concentration of 50 µM at 37° C. in dark conditions for 20 mins. Cells were centrifuged (400 g, 5 mins) and washed in 10×DPBS volume and incubated again at 37° C. in dark conditions for 20 mins. Finally, stained cells centrifuged and resuspended in DPBS at 1×107 cells/mL and stored on ice until transplantation.

Serum preparation: Blood was allowed to clot overnight at 4° C. Serum was obtained via sequential centrifugation. Briefly, serum was separated from blood cells by centrifugation at 1500 g (5 mins, 4° C.) and pipetted off to a fresh microtube. Serum was centrifuged again (14 000 g, 5 mins, 4° C.) to pellet any residual blood cells and cell debris. Serum was transferred to fresh microtubes and frozen at −20° C. until use.

Serum chemistry evaluation: Serum chemistry was performed by measurement of alanine aminotransferase (ALT), aspartate aminotransferase (AST), alkaline phosphatase (ALP), total bilirubin, and serum albumin. ALT was measured using the method described by (21), utilising a commercial kit (Alpha Laboratories Ltd). AST and ALP were determined by a commercial kit (Randox Laboratories). Total bilirubin was determined by the acid diazo method described by Pearlman and Lee (22) using a commercial kit (Alpha Laboratories Ltd). Mouse serum albumin measurements were determined using a commercial serum albumin kit (Alpha Laboratories Ltd). All kits were adapted for use on a Cobas Fara centrifugal analyzer (Roche Diagnostics Ltd). For all assays, intra-run precision was CV <4%. In some experiments, assays were run on plasma samples with the exception of ALP activity.

Haematoxylin and eosin staining and necrosis quantification: Four micron sections of liver tissue were cut on a rotary microtome and collected on Surgipath Superior Adhesive Slides (Leica Biosystems) and dried overnight at 45° C. Sections were stained with haematoxylin and eosin on a Shandon Varistain Gemini ES Automated Slide Stainer (ThermoScientific) and mounted using the Shandon ClearVue Coverslipper (ThermoScientific). For necrosis quantification, slides were scanned to create a single image with Dotslide VS-ASW software (Olympus) using a motorised stage and an Olympus BX51 microscope, acquiring images using an Olympus PlanApo 2X lens and Olympus XC10 camera. Images were analyzed using the Trainable WEKA Segmentation plugin (23) in FIJI (24, 25). A separate classifier identifying necrotic and viable tissue was determined and applied to all tissue in each image.

BrdU immunofluorescence staining: Four micron sections of formalin-fixed paraffin-embedded (FFPE) blocks were collected on Superfrost™ Plus slides. Sections were dewaxed and rehydrated before heat-induced antigen retrieval in sodium citrate (pH 6.0) buffer. Sections were blocked in protein solution (Spring Bioscience, Pleasanton, Calif.) for 30 mins, before incubation with rat anti-BrdU primary antibody (Abcam) for 30 mins or isotype-control rat IgG (Vector Laboratories). Sections were washed extensively with PBS before application of goat anti-Rat IgG Secondary Antibody, Alexa Fluor® 555 conjugate for 60 mins in a dark environment. Sections were washed again with PBS before mounting in DAPI-containing fluoromount G and a coverslip. Sections were imaged on Operetta high content imaging system (PerkinElmer) and quantified based on percentage of positive cells containing signal at 546 nm in DAPI-positive regions (nuclei). For colocalisation experiments, dual stains were performed with Hnf4a (goat anti-mouse, Santa Cruz) and CD31 (rabbit anti-mouse, Abcam) using an Alexa Fluor® 488 conjugate (incubated for 60 mins in a dark environment).

Serum and liver quantification of pro-inflammatory cytokines: A panel of pro-inflammatory cytokines (IFN-γ, IL-10, IL-12p70, IL-1β, IL-2, IL-4, IL-5, IL-6, KC/GRO, TNF-α) were multiplexed in mouse serum or liver homogenates using luminescent-based V-plex pro-inflammatory panel 1 (mouse) kit (Meso Scale Diagnostics) essentially according to the manufacturer's instructions. For liver homogenates, 75 mg liver tissue was lysed in cold lysis buffer (150 mM NaCl, 20 mM Tris, 1 mM EDTA, 1 mM EGTA, 1% Triton X-100 (v/v), 2×protease inhibitor cocktail, (Sigma Aldrich) using a Tissue Tearor homogeniser (Biospec Products). Crude homogenates were centrifuged (20,000 g, 10 mins, 4° C.) to remove cell debris. Protein concentrations were determined on supernatants using the Bicinchoninic Acid (BCA) assay method. For cytokine quantification, 25 µL of serum or 100 µg liver homogenate was added to each well and mixed with diluent 41 in a volume of 50 µL and incubated for 2 hours on a shaking plate-mixer (600 rpm). Wells were washed extensively (PBS, 0.05% Tween 20 v/v) before application of a cocktail of secondary antibodies. Plate was assayed on a QuickPlex SQ 120 analyzer (Meso Scale Diagnostics) and analytes were quantified based on linear regression against the standard curve of each analyte. Standards were assayed in duplicate as recommended. Due to the high intra-assay precision and high number of biological replicates, samples were assayed in singlet.

Gene expression analysis to confirm appropriate BMDM cytokine-induced polarisation on ultra-low attachment plastics in vitro: BMDMs were seeded at 2.5×105 cells/well in 24 well plastic plates or 24-well ultra-low attachment plates. Cells were allowed to adhere overnight in complete media (DMEM:F12 media containing 20 ng/mL CSF1). Media was removed and replaced with DMEM:F12 media with and without appropriate cytokines (n=3; see methods above) for 48 hours to drive polarisation. RNA was harvested from cells using the RNeasy Mini Kit (Qiagen) according to the manufacturer's instructions. RNA was quantified spectrophotometrically using Nanodrop ND-1000 (Thermo Scientific) and reverse transcribed using Quantitect Reverse Transcription kit (Qiagen) including genomic DNA removal step. Gene expression was quantified using QuantiTect SYBR Green PCR Kit (Qiagen) in 384-well format on a Roche Lightcycler 480 II (Roche, Basel, Switzerland). Gene expression was measured using commercially-available Quantitect primers (Qiagen) designed for the following genes: iNos, Tnf, Mcp (for CAMs), Ym1, Fizz, Mr, Arg1 (for AAMs) and Il10 (for DAMs; Il-10-BMDMs). Relative expression was determined using the 2-ΔΔCT method versus naïve BMDMs using 18S rRNA as the housekeeping gene.

Gene expression analysis for pro-inflammatory gene expression analysis on liver tissue from APAP-treated mice: Approx. 10 mg frozen liver tissue was weighed and homogenised in 900 μL Qiazol lysis reagent (Qiagen) using the tissue tearor. Chloroform (200 μL) was added, mixed by hand, and allowed to incubate (5 mins, room temp.). RNA was removed in aqueous phase after centrifugation (12000 g, 15 mins, 4° C.) and precipitated with isopropyl alcohol. After an ethanol wash, RNA was resuspended from air-dried pellets using RNAse free water. RNA was quantified, DNase-treated, reverse transcribed as described. Quantitect primers (Qiagen) against Csf1, Csf2, Csf3, Ccl2, Ccl3, Ccl5, Ccl7, Ccl12, Cxcl1, Cxcl2, Il-6, Tnf and Tgfβ were used for gene expression analysis. Gapdh served as the housekeeping gene.

Phagocytosis assays: Unpolarised BMDMs (naïve), CAMs, or AAMs were used to investigate phagocytosis. BMDMs were incubated with apoptotic thymocytes (primary thymocytes harvested from 3-5 week old C57BL6 mice, treated with 1 μM hydrocortisone, as previous (26). Apoptotic thymocytes were labelled using CMTMR (Invitrogen) according to the manufacturer's instructions (27). BMDMs were challenged with labelled apoptotic cells for 30 mins, 1 hour, or 2 hours at a 1:5 ratio at 37° C. or 4° C. Cells were washed and phagocytosis verified by flow cytometry after staining with anti-CD11b BV650 (clone M1/70; Ebioscience) and anti-Ly6C V450 (clone HK1.4; Ebioscience). Phagocytosis was calculated as percentage of CD11 b+ CMTMR+ cells at 37° C. minus percentage of CD11 b+ CMTMR+ cells at 4° C. Percentage of Ly6C+ cells was calculated in the gate of CD11b+ CMTMR+ cells at 37° C. Mean fluorescence intensity (MFI) for CMTMR was calculated on the same gate in the same conditions. Data were acquired on a LSRII Fortessa (BD Biosciences).

Phagocytosis assays for real time experiments: Mouse BMDMs or hMDMs were plated (1×105/well) in 96-well CellCarrier microplates (PerkinElmer) overnight before stimulation with appropriate cytokines (see methods above) to drive polarisation. Before imaging, BMDMs were stained with NucBlue live cell stain (ThermoFisher) and CellMask Deep Red plasma membrane stain (ThermoFisher) according to the manufacturer's instructions. Plates were transferred to Operetta high-content imaging system (PerkinElmer) and allowed to equilibrate at 37° C. and 5% CO2. Phagocytosis was initiated by the addition of pHrodo green zymosan bioparticles (ThermoFisher) to the wells following manufacturer's instructions. Fluorescent images were taken in the DAPI channel, 488 nm, and 647 nm before, and at 5 min intervals after the addition of bioparticles for a maximum of 150 mins. Images were quantified on Columbus image analysis software (Perkin Elmer). Macrophages positive for phagocytosis were classified based on a fluorescence intensity (488 nm) greater than 500 and expressed as a fraction of all live cells (NucBlue positive cells). Mean fraction values were taken from four separate wells per group.

Liver digest, leukocyte isolation, and flow cytometry: To examine the localisation and phenotype of transplanted AAMs in vivo, CFSE-stained AAMs or vehicle was transplanted to mice at 16 hours after APAP administration. Three hours later, mice were challenged with an i.v. injection of PKH26PCL (100 μL, 0.1 mM) to label phagocytic cells. At 36 hours, blood was collected from sacrificed mice in EDTA-tubes and processed immediately on a Celltac α analyzer (Nihon Kohden) for haematological analysis. Plasma was harvested from the remainder of the blood via centrifugation (6000 rpm, 10 min, 4° C.) and frozen. Liver was digested following methods previously described (15, 28) with minor modifications. Briefly, livers were perfused with PBS and the left lateral lobe was collected at 36 hours post-APAP administration in ice-cold RPMI media. Lobes were mechanically disrupted with a scalpel in 5 mL liver digestion enzyme cocktail (Collagenase V, Sigma, 0.8 mg/mL; Collagenase D, Roche, 0.63 mg/mL; Dispase, Gibco, 1 mg/mL; DNase 1, Roche, 100 μg/mL). Homogenates were digested for 25 mins in a shaking incubator at 37° C. at 240 rpm. Liver digests were passed through a 70 μm filter and made up to 30 mL with RPMI. Digests were centrifuged (300 g, 5 mins, 4° C.) and washed before red blood cell lysis treatment (Sigma). Cells were counted and stained using a panel of antibodies to target cell surface markers with appropriate controls (i.e. unstained, fluorescence minus one). Nonspecific antibody binding was blocked by incubating cells with 10% mouse serum for 20 mins at 4° C. followed by incubation with combinations of primary antibodies (each used at 1:200 dilution) for 20 mins at 4° C. The following conjugated antibodies were used: CD11 b BV650 (clone M1/70; Ebioscience), Ly-6C V450 (clone HK1.4; Ebioscience), CD45.2 AF700 (clone 104; Ebioscience), F4/80 APC (dilution 1:100; clone BM8; Invitrogen), Ly-6G PE-Cy7 (clone 1A8; Biolegend), CD3 PE-Cy7 (clone 17A2; Biolegend), NK1.1 PE-Cy7 (clone PK136; Biolegend), CD19 PE-Cy7 (clone 6D5; Biolegend). Cell viability was assessed with Fixable Viability Dye eFluor780 (1:1000, Ebioscience) according to manufacturer's protocols. After antibody staining, samples were either analyzed immediately or fixed with BD Cell Fix (BD Bioscience) before analysis on an LSRII Fortessa (BD Biosciences) flow cytometer. Data were analyzed using FlowJo10 software (Tree Star).

Statistics: All data is presented as mean±standard deviation unless otherwise stated. For statistical tests, a student's t-test was performed on two groups of parametric data and Mann-Whitney U-test was performed on two groups of non-parametric data sets. For data sets including more than one group, a one-way ANOVA was performed on parametric datasets. Shapiro-wilk test was used to determine if datasets were normally distributed. All statistics were performed in GraphPad Prism 6.0 (GraphPad Software).

Results

BMDMs track to spleen and liver rapidly after intravenous administration: in vivo and ex vivo imaging techniques were employed to monitor the early biodistribution of BMDMs in healthy and APAP-poisoned mice. To monitor hepatic localisation, BMDMs were labelled with and without Vivotrack 680 (a fluorescent infra-red imaging agent) and transplanted (5×106, i.v.) to mice 16 hrs post-APAP administration or healthy controls. An almost linear accumulation of fluorescent signal in the upper abdomen of healthy and APAP-treated mice was observed over the first four hours suggesting gradual localisation in one or more abdominal organ (FIG. 1A, B). BMDMs tolerated Vivotrack labelling well showing no significant reduction in ATP levels post-labelling (FIG. 1C). Furthermore, fluorescent microscopy showed GFP-positive BMDMs display a strong and uniform infra-red fluorescent signal after vivotrack labelling cells versus unlabelled cells that are only visible at 488 nm (FIG. 1D). Ex vivo analysis confirmed hepatic and splenic localisation of BMDMs in healthy and APAP-treated mice 4 hours after BMDM administration (FIG. 1E). There was also substantial signal observed in lung which likely acts as a barrier for venous blood to pass though. Quantification showed that hepatic localisation was higher in healthy mice whilst splenic localisation was equivalent (FIG. 1F). Finally, using a microscopic approach, BMDMs were stained with CFSE (CellTrace, Life Technologies) in vitro, transplanted 16 hours post-APAP, and culled at 36 hours. CFSE-stained cells were detected using DAB-based immunohistochemical staining versus FITC. DAB-positive cells were detected in spleen and liver in FFPE sections that have typical macrophage morphology (FIG. 1G), but not in lung, heart or brain (data not shown). Hepatic and splenic BMDM localisation was observed in healthy and APAP-poisoned animals with some BMDMs localised in the necrotic lesion which was visualised by diffuse background DAB staining around the central vein (FIG. 1G).

Figure 2:
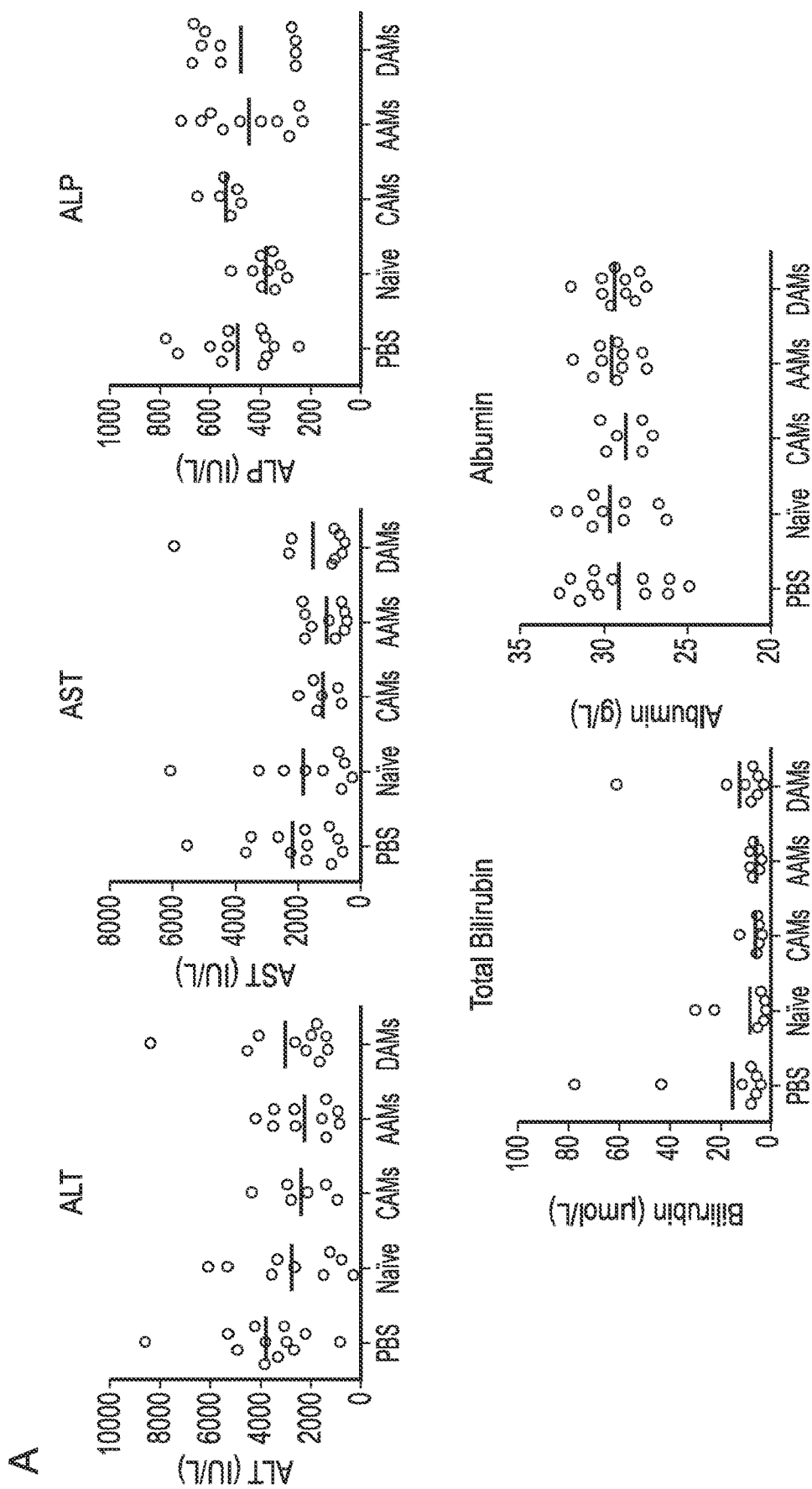
FIG. 2 shows alternatively activated macrophages (AAM) reduce hepatic necrosis following APAP-induced liver injury. Fasted mice were treated with APAP (350 mg/kg; i.p) and were treated with unmanipulated (naïve) or pre-polarised BMDMs (classically activated macrophages (CAMs), AAMs, or deactivated macrophages (DAMs)) 16 hours post-APAP administration. (A) Serum chemistry analysis of liver injury biomarkers (ALT/AST/ALP) and function markers (Total bilirubin/serum albumin) show no differences between treatment groups. Open circles represents values from individual animals per group as indicated (B) Haematoxylin and Eosin (H+E) stains indicate typical eosinophilic necrotic regions surrounding the central vein characteristic of APAP-induced liver injury. Panels show representative images from mouse liver (2× magnification). Necrotic quantification is shown bottom right as open circles per individual animals around the mean (horizontal line) in groups as shown. Asterisk indicates statistical significance ($P<0.05$, Kruskall-Wallis test).
Figure 2:
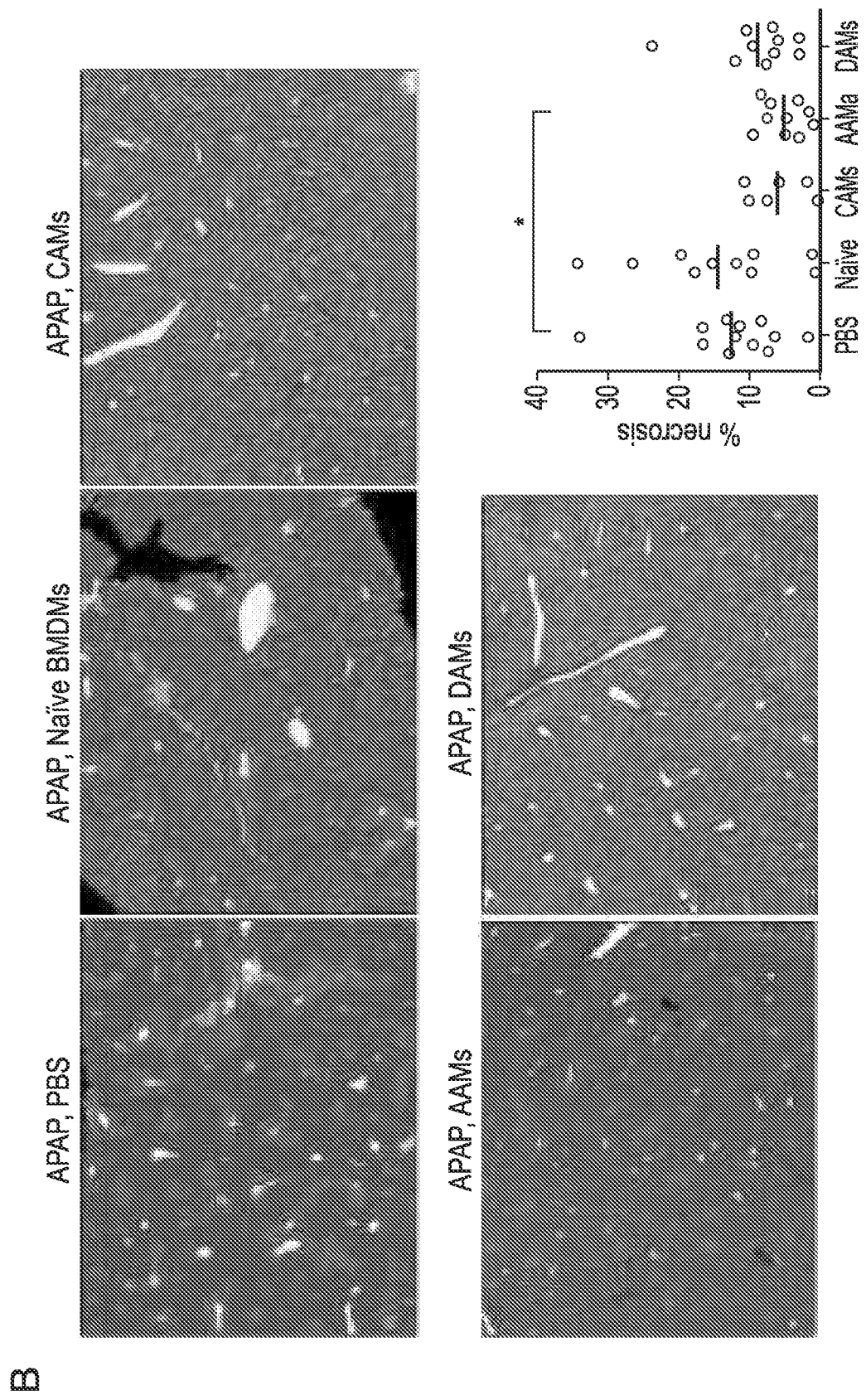
Figure 8:
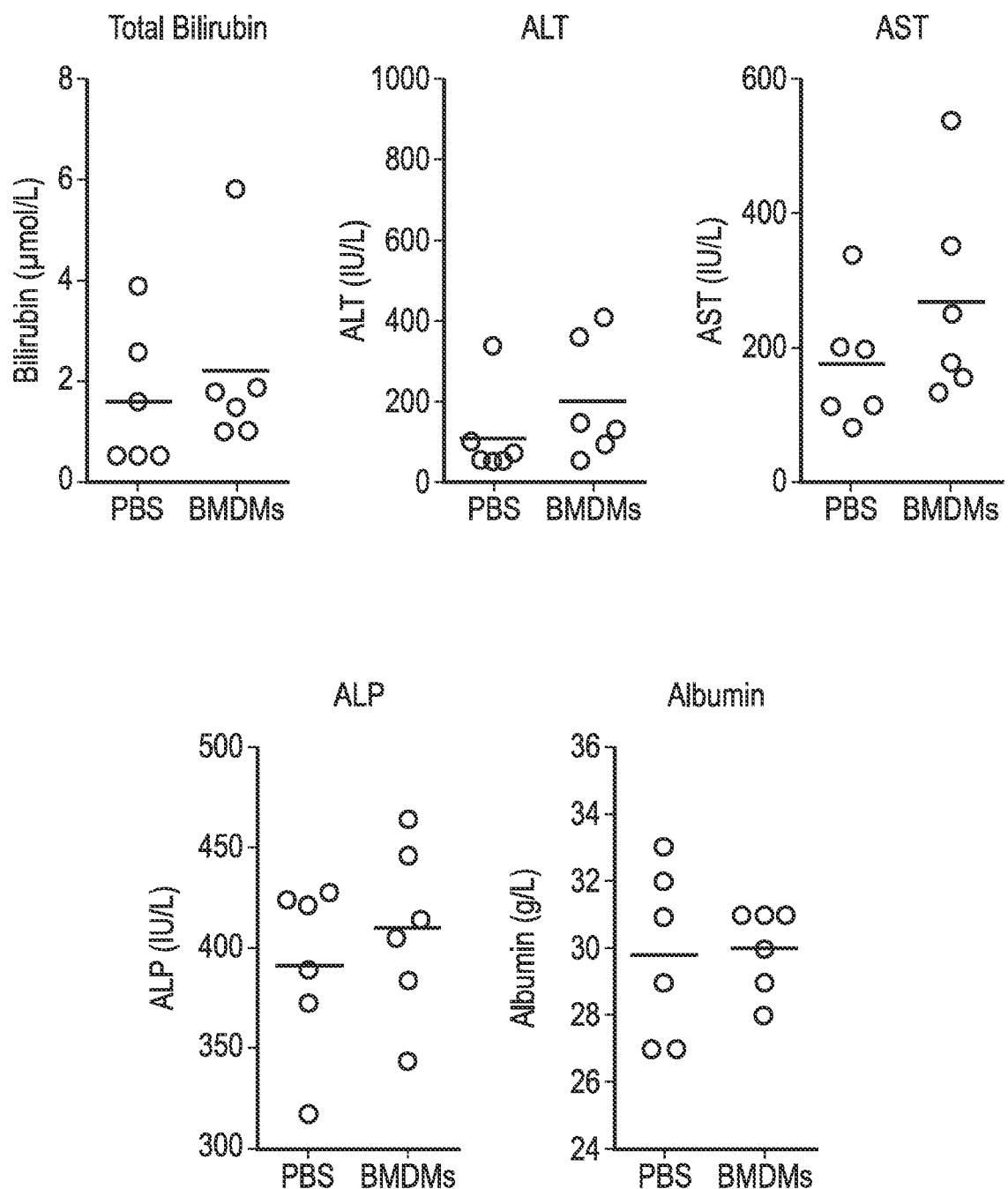
FIG. 8 shows serum chemistry following unmanipulated BMDM administration in healthy mice. Markers of liver injury and function were assayed in mouse serum harvested 20 hours following BMDM administration (1×106 cells, i.v.). Panels show values for individual mice (open circles) around the mean (black line) in groups. None of the biomarkers were statistically significant in the BMDM group versus PBS vehicle control (student's t-test).
Figure 9:
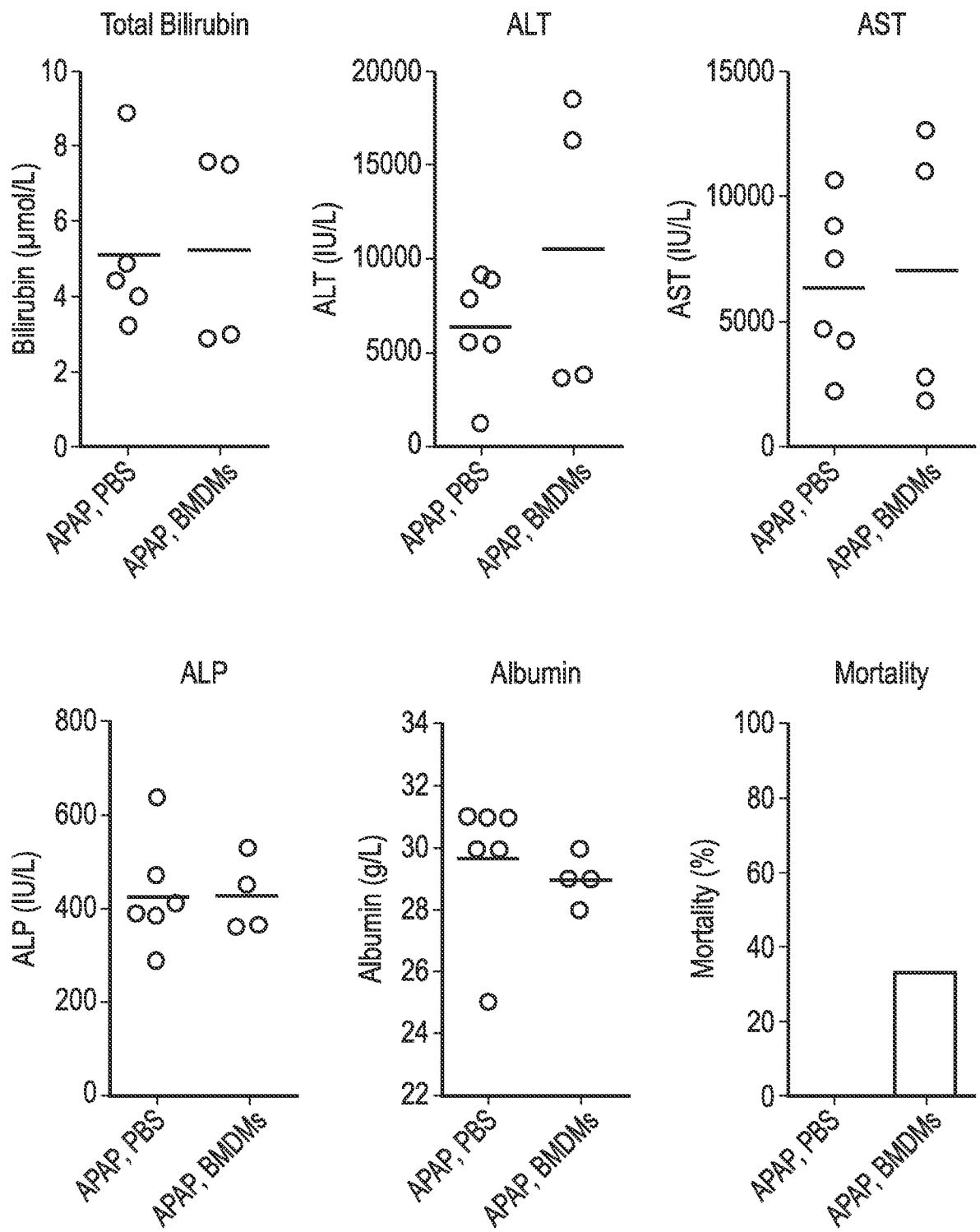
FIG. 9 shows naive BMDMs administered early (4 hours) after APAP treatment does not reduce liver injury. Markers of liver injury and function were assayed in mouse serum harvested 24 hours after APAP administration (20 hours after BMDM administration; 1×106 i.v.). Although the markers measured were not statistically significant, serum transaminases showed a higher trend in a BMDM-treated mice and deaths were only observed in BMDM-treated group (student t-test).
Figure 10:
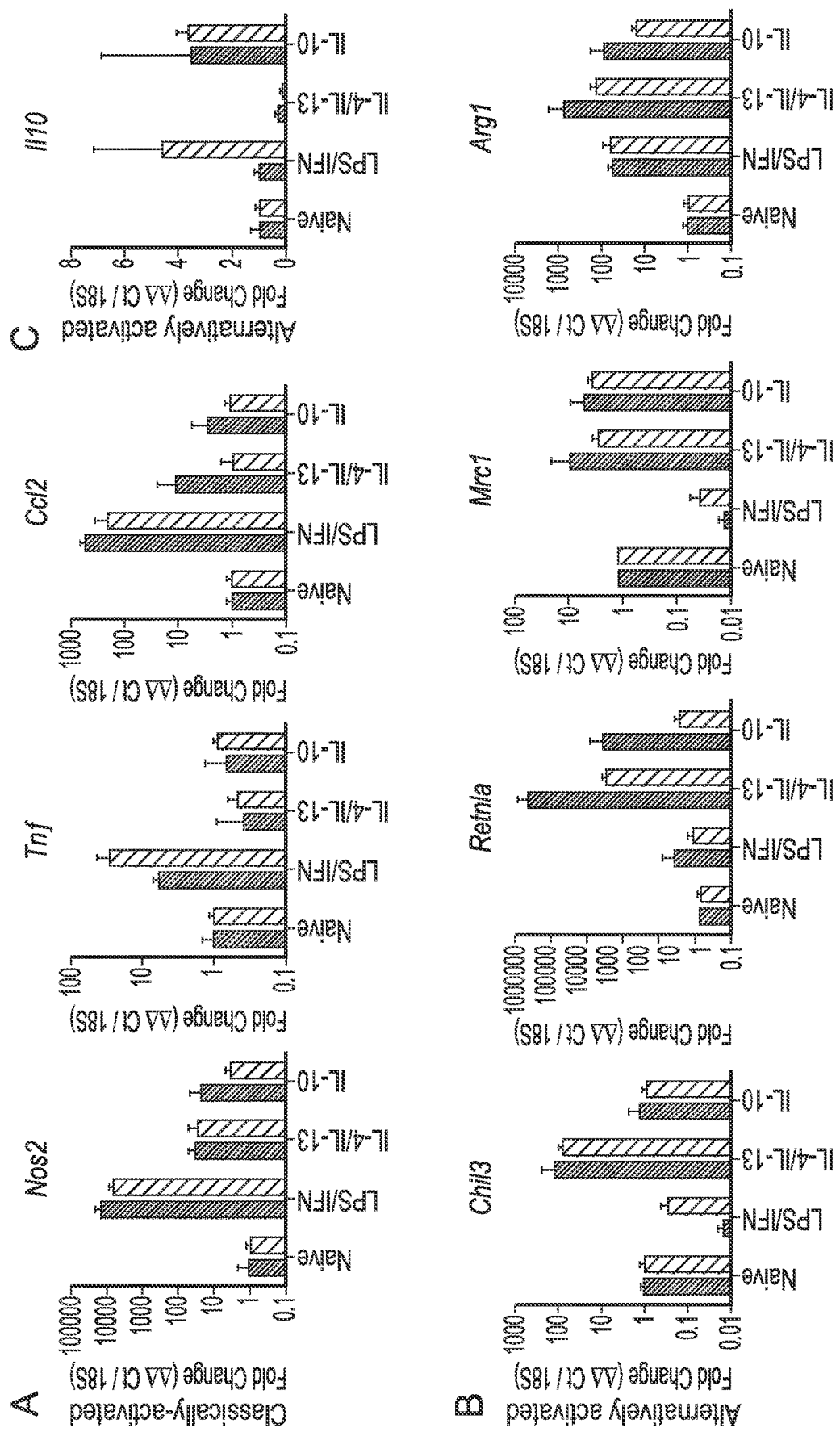
FIG. 10 shows cytokine-mediated BMDM polarisation occurs on normal and ultra low-attachment plastics. BMDMs were cultured with either LPS (50 ng/mL) and IFNγ (20 ng/mL)—for CAMs), IL-4 (20 ng/mL) and IL-13 (20 ng/mL)—for AAMs, IL-10 (10 ng/mL)—for DAMs or without growth factors (naïve macrophages) for 48 hours on either normal plastic (black bars) or ultra-low attachment plastic (grey bars). (A) Relative gene expression analysis for classically-activated genes (Nos2, Tnf, Ccl2) show a substantial and consistent increase in expression in BMDMs treated with LPS/IFN on both normal and low-attachment plastics. (B, C) Gene expression analysis of archetypal alternatively-activated genes (B, alternatively-activated genes: Chil3, Retnla, Mrc1, Arg1; C, DAM: Il10) show consistent increase in expression in BMDMs cultured with IL-4/IL-13 (B) and IL-10 (C) respectively. Alternatively activated genes were upregulated by IL-4/IL-13 on both plastic types whereas Il10 gene expression was higher on low-attachment plastics after IL-10 treatment.
Figure 11:
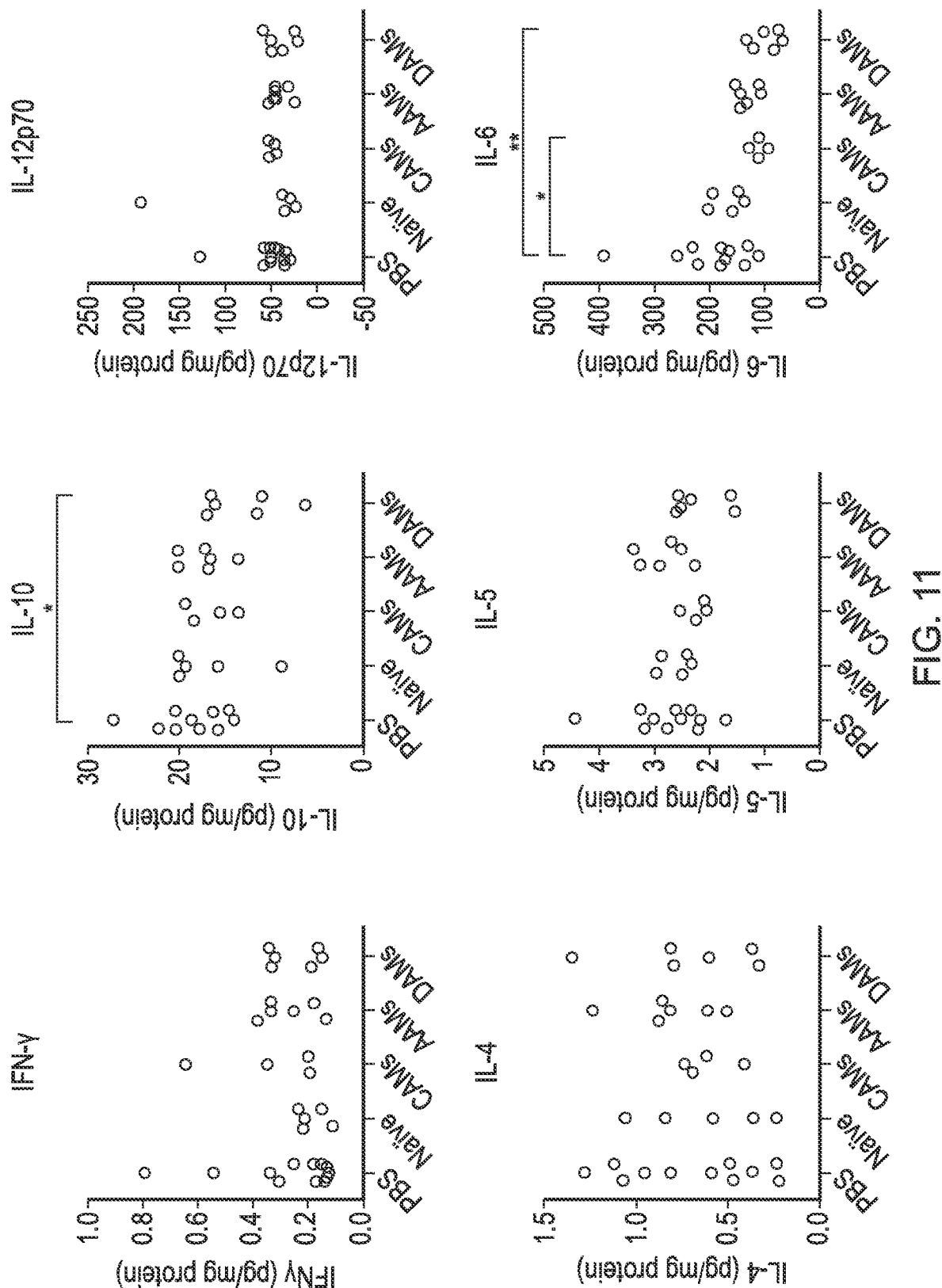
FIG. 11 shows polarised BMDM administration shows a lower trend across a panel of inflammatory cytokines in whole liver in mice with APAP-induced liver injury. Serum from mice treated with BMDMs (naïve, CAMs, AAMs) were assayed for a 10-plex panel of pro-inflammatory cytokines using electrochemiluminescence technology (Meso Scale Discovery, Gaithersburg, Md.). Panels show data in groups for each cytokine analysed (IFN-γ, IL-10, IL-12p70, IL-1β, IL-2, IL-4, IL-5, IL-6, CXCL1 (KC/GRO), TNFα). Each open circle represents data points from individual animals per group. Asterisks represent levels of statistical significance (* P<0.05,  P<0.01, * P<0.001; one-way ANOVA).
Figure 11:
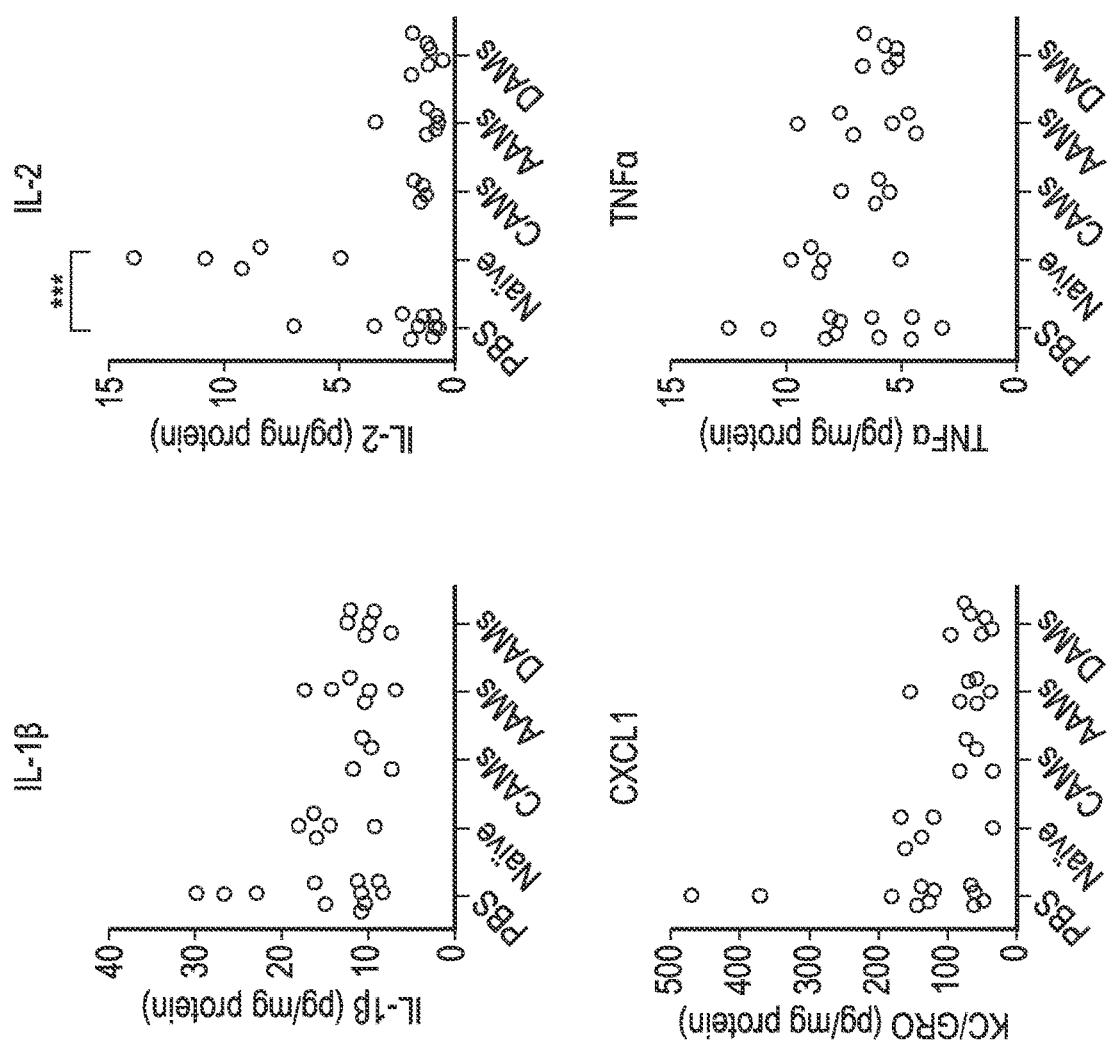
Figure 12:
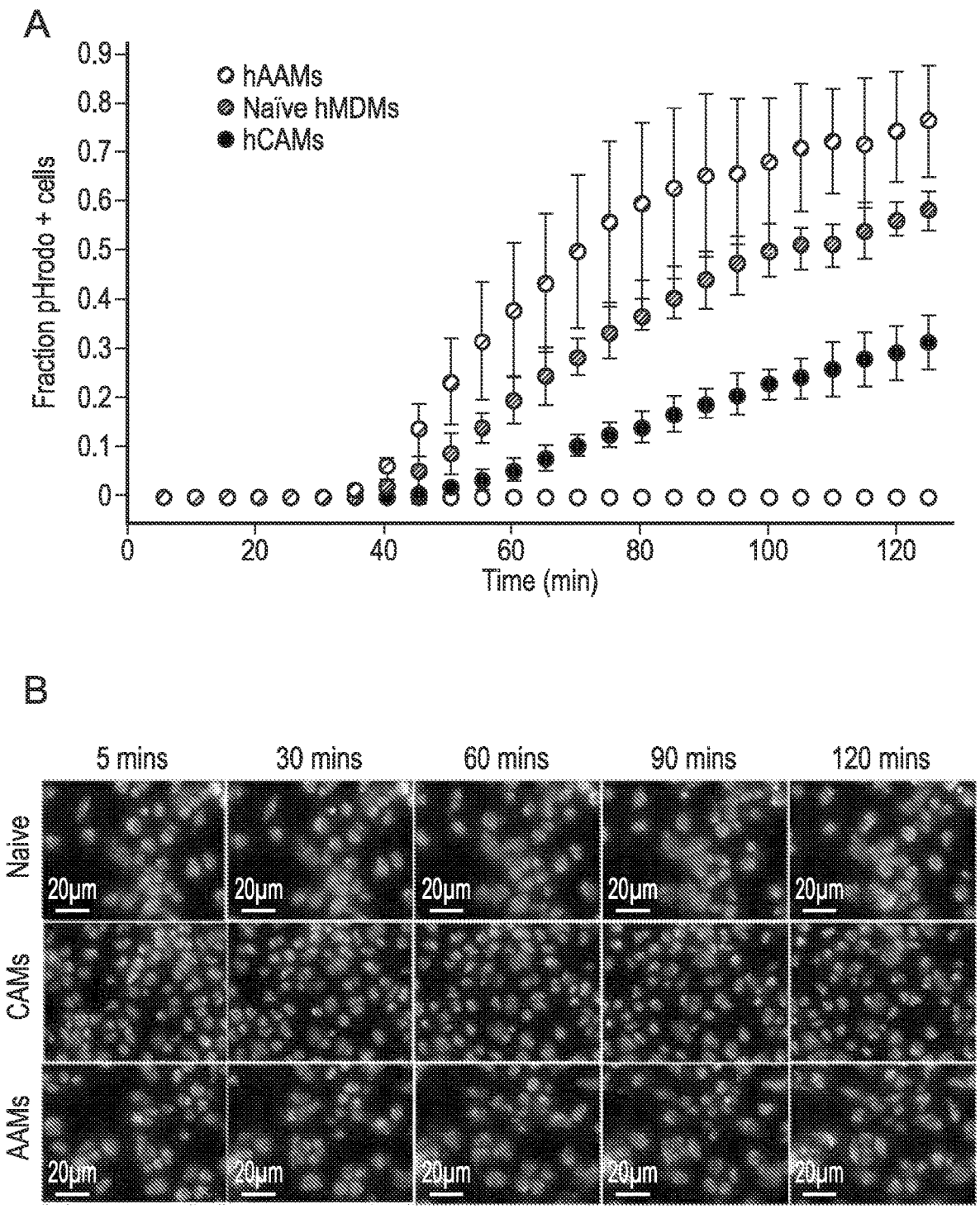
FIG. 12 shows human monocyte derived macrophages show altered phagocytosis kinetics after in vitro polarisation. Human monocytes were incubated in vitro with human recombinant CSF1 for 7 days to drive differentiation before culture with LPS/IFN (for classical activation, towards hCAMs), IL4/IL-13 (for alternative activation, towards hAAMs), or no stimuli (naïve MDMs). Macrophages were seeded at 1×105 cells/well in 96-well CellCarrier plate and incubated with zymosan green pHrodo bioparticles for 125 minutes. (A) Real time mean fraction of pHrodo positive cells from four wells per group. Spots show the mean value around the standard deviation. (B) Representative images from hMDMs in culture at different times during the incubation. Blue stain presents NucBlue nuclei. Red stain is Deep Red cell mask cytoplasmic stain. Green signal represents ingested pHrodo bioparticles in the acidic lysosomes. Trend of phagocytosis was similar to mouse BMDMs but with a delayed onset of particle ingestion.
Figure 13:
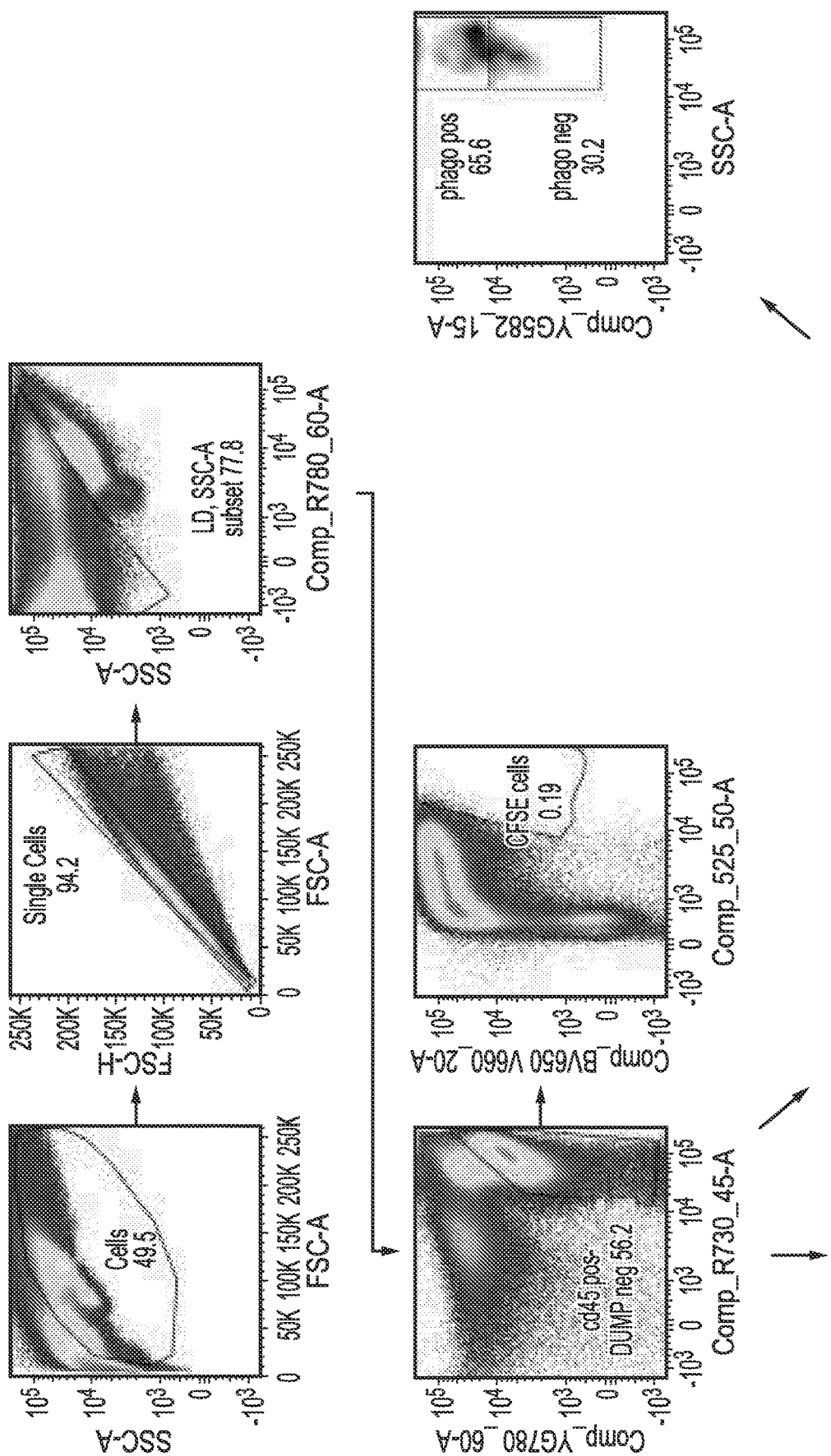
FIG. 13 shows flow cytometry gating strategy. Representative flow plots from categorising sub-populations of liver digests. Top panels show all cells used for analysis, excluding doublets, and negative for the liver/dead stain. Sub-populations were expressed as proportions of total hepatic macrophages or CD45+cells. Hepatic resident macrophages were defined as viable CD45+ Ly6G− CD3− NK1.1− CD19− CD11b$^{low}$ F4/80$^{high}$. Hepatic infiltrating macrophages were defined as viable CD45+ Ly6G− CD3− NK1.1− CD19− CD11b$^{high}$ F4/80$^{low}$ cells from non-parenchymal fraction of digested livers and used to identify macrophage subsets. Quantification of absolute numbers of cells per liver was performed by expressing each subset as a proportion of NPCs, counting total number of NPCs in the digested portion of liver, calculating the total number of NPCs in the whole liver by weight differential, thereby calculating the total number of each subpopulation. Transplanted AAMs were identified as CFSE+. The percentage CFSE+ cells was calculated on the gate of total viable CD45+ Ly6G− CD3− CD19− NK1.1− cells. The negative was set on a liver from an APAP-poisoned mouse receiving vehicle instead of AAMs. AAMs were further classified on their Ly6C expression, gating set using FMO controls. The percentage of phagocytic cells (positive and negative) was calculated on the gate of CFSE+ cells. The negative was set using the liver from an APAP-poisoned mouse transplanted with AAMs but injected with the vehicle instead of PKH26PCL. PKH26PCL MFI was calculated in the same gate.
Figure 13:
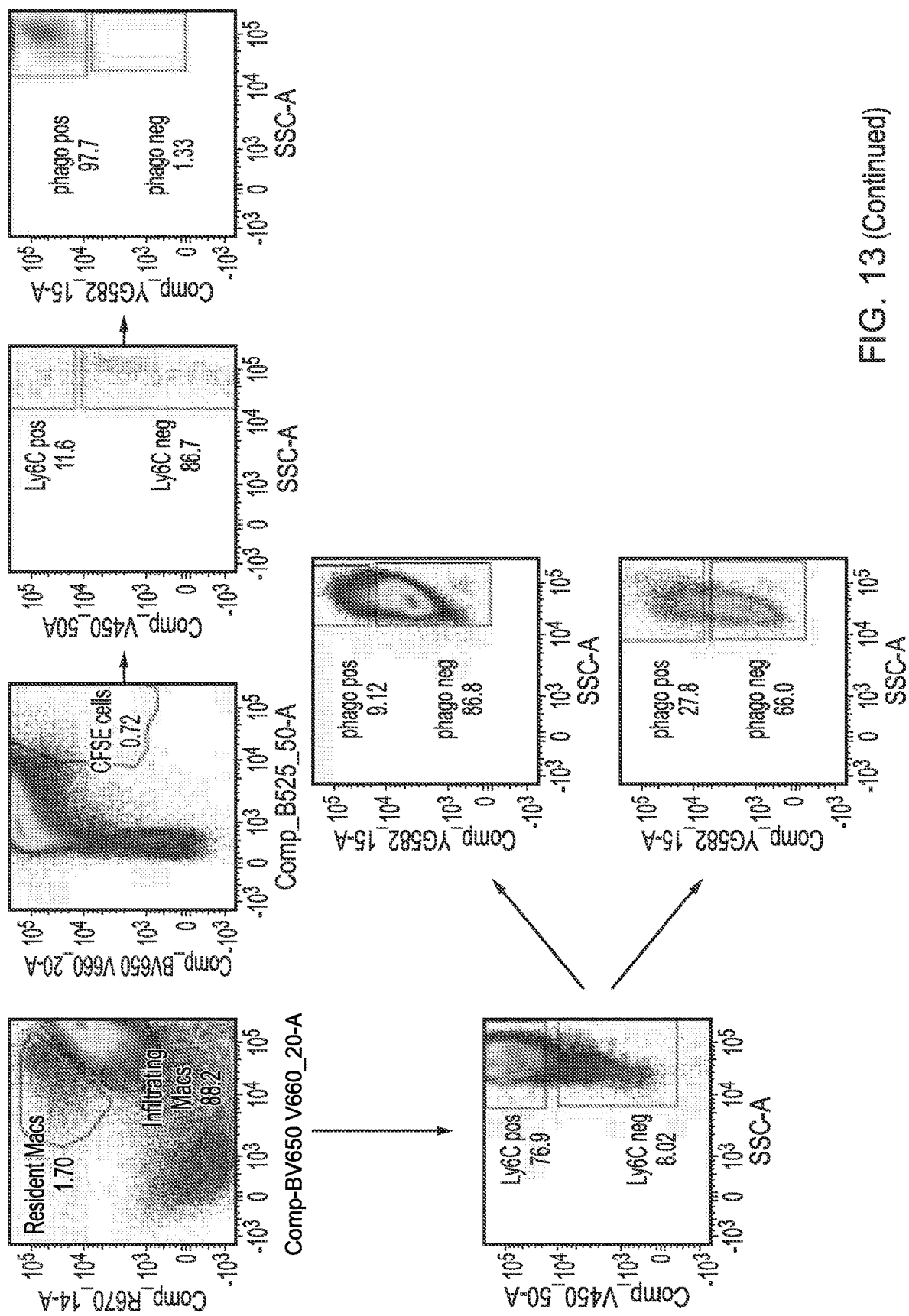
Figure 14:
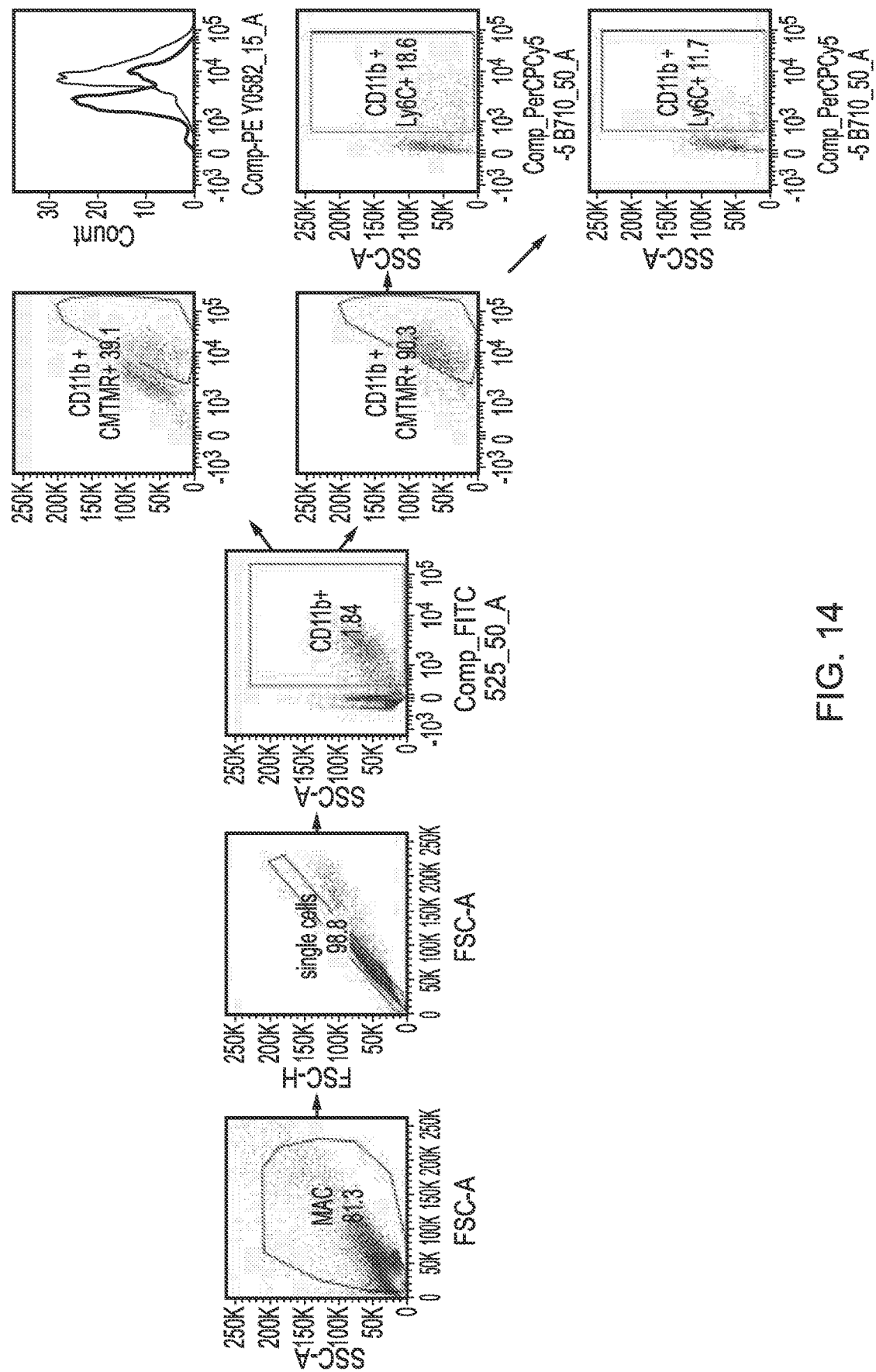
FIG. 14 shows flow cytometry gating strategy. Representative flow plots from categorising sub-populations of phagocytosis analysis. Panels show all cells analysed in the study, excluding doublets. BMDMs were identified as CD11b+. The percentage of phagocytic cells was calculated on the gate of CD11b+ cells. BMDMs positive for phagocytosis were defined as CMTMR+ (i.e. fluorescent apoptotic thymocytes). The percentage of non-specific binding (phagocytosis at 4° C., top right panels) was subtracted from the percentage of phagocytic BMDMs (at 37° C.). Phagocytic cells were further classified based on their Ly6C expression (bottom right panels). Gates were set using FMO controls.
Figure 15:
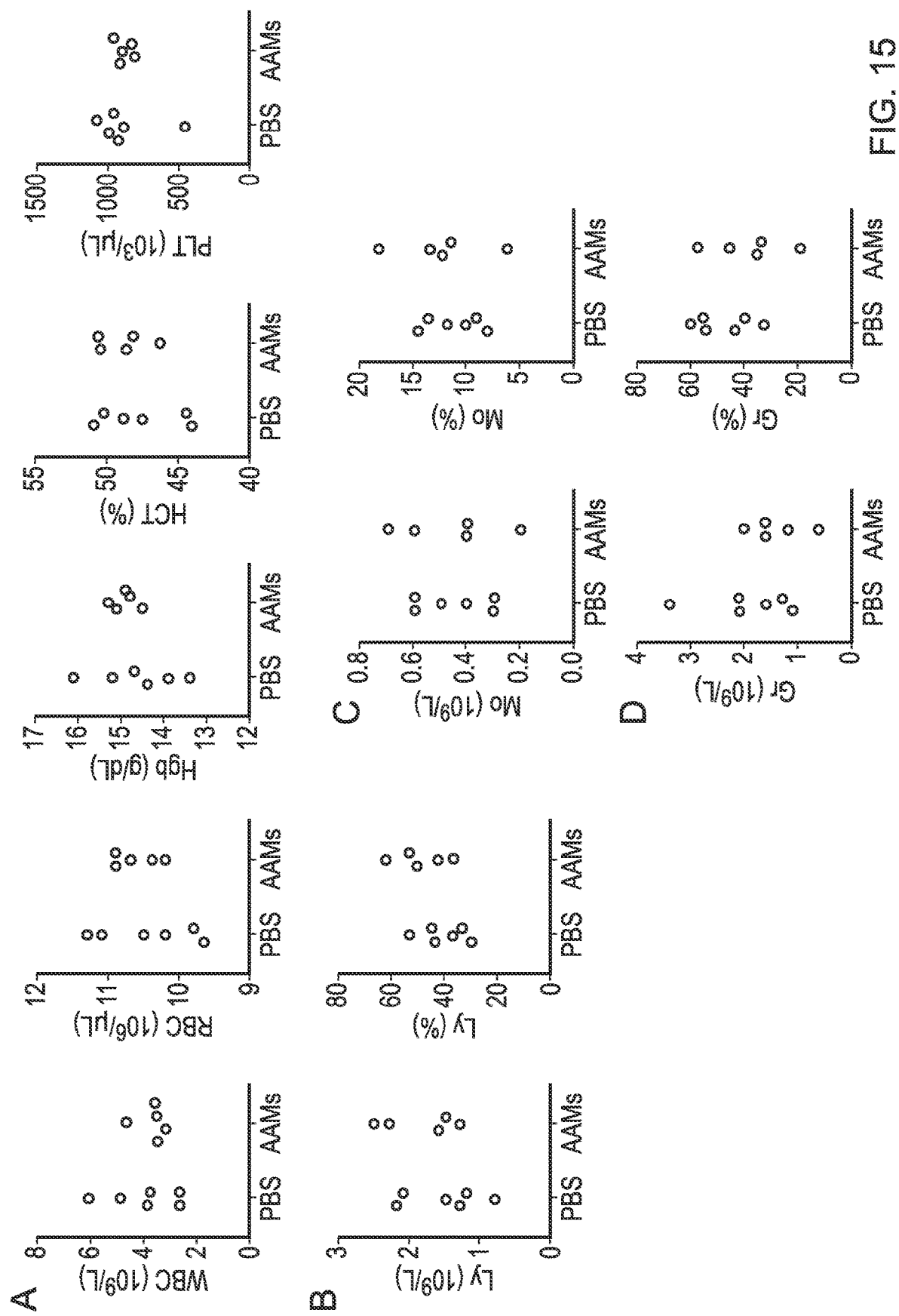
FIG. 15 shows whole blood parameters following AAM delivery in APAP poisoned mice. We observed no statistical difference between any parameter of whole blood in poisoned animals that received DPBS (vehicle control) versus AAM (5×106, i.v.). (A) Panels show open circles (individual animals) categorised per group as indicated for white blood cells (WBC), red blood cells (RBC), haemoglobin (Hgb), haematocrit (HCT), and platelets (PLT). (B) The number (left) and percentage (right) of lymphocytes per group. (C) The number (left) and percentage (right) of monocytes per group. (D) The number (left) and percentage (right) of granulocytes per group.

AAM treatment reduces necrotic area in APAP-treated mice: To test the therapeutic potential of BMDMs to treat ALI, we used a mouse model of APAP-induced liver injury which leads to peak hepatic injury necrosis peaking at approx. 12 hours post-APAP administration. BMDM transplantation alone in healthy animals did not cause any significant perturbations to circulating liver biomarkers (FIG. 8) routinely measured during clinical chemistry. We tested whether unmanipulated (naïve) BMDMs (1×106, i.v.) could reduce injury given shortly (four hours) after APAP administration. Naïve BMDM therapy had no therapeutic benefit given 4 hours after APAP as evidenced by lack of reduction of serum transaminases at 24 hours post-APAP (APAP/PBS vs APAP/BM DMs; ALT: 6365±2955 vs 10603±7974 U/L, AST: 6333±3138 vs 7068±5584 U/L) (FIG. 9). Also, two mice in the BMDM-treated group were culled early for humane reasons after showing an exaggerated phenotype. Therefore, we transplanted BMDMs 16 hours after APAP administration (1×106, i.v.) during the regenerative phase. BMDMs were polarised to different phenotypes in vitro using recombinant factors. Serum ALTs at 36 hours post-APAP were moderately lower in all BMDM-treated groups (FIG. 2A, PBS: 3800±1934 U/L vs Naïve: 2737±2020, CAMs: 2413±1222, AAMs: 2248±1196, DAMs: 2993±2182) but did not reach statistical significance. Since serum transaminases have a relatively long circulatory half-life and may still be raised by subsequent injury, we performed haematoxylin and eosin staining on liver tissue harvested at 36 hours. Centrilobular necrosis caused by APAP was quantified using image analysis software, necrotic area was expressed as a percentage of all liver tissue. Mice treated with AAMs showed a 60% reduction in necrotic area (FIG. 2B, P<0.03).

Figure 3:
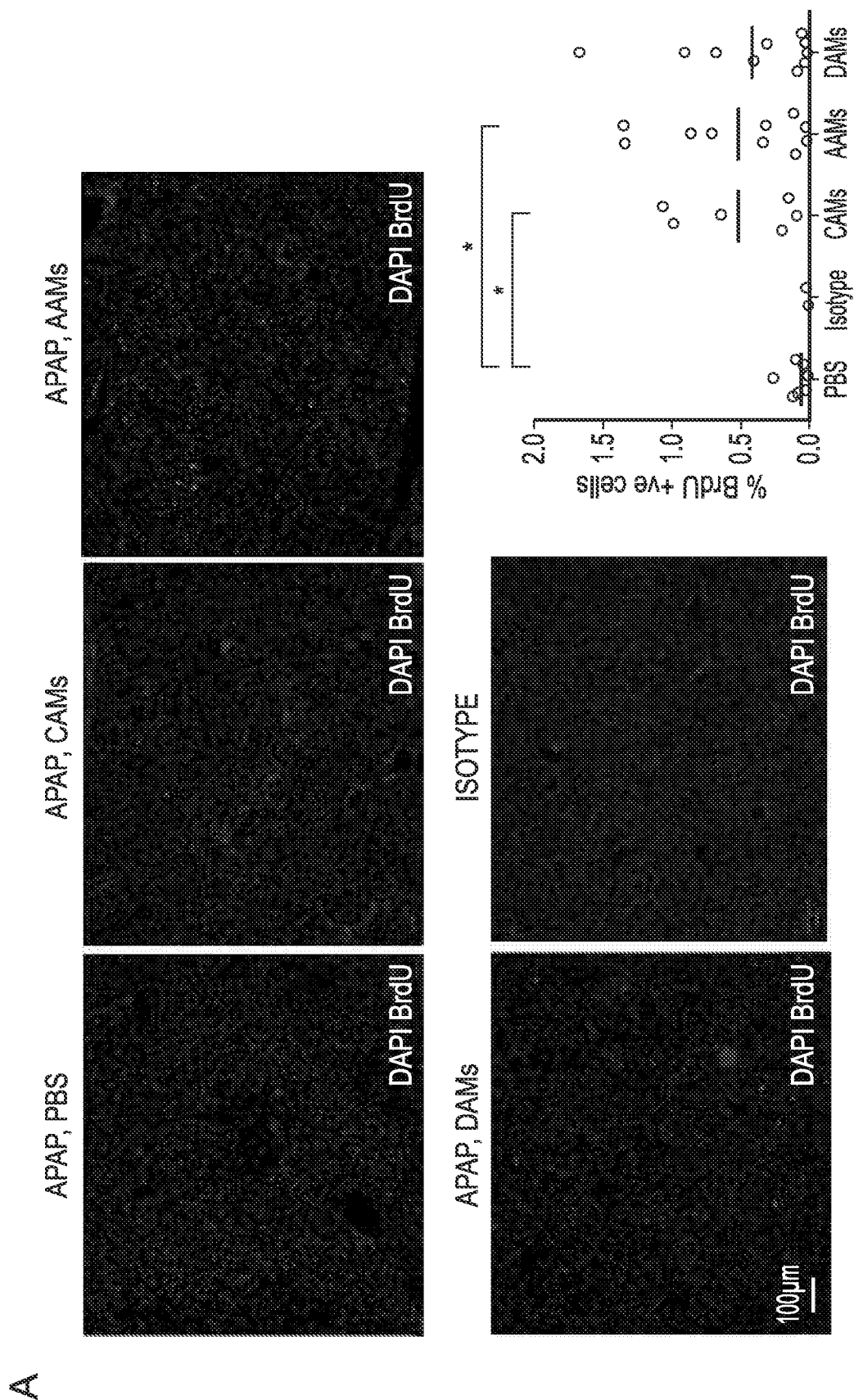
FIG. 3 shows polarised BMDM treatment induces hepatocellular proliferation following APAP-induced liver injury. (A) Mice treated with polarised BMDMs following APAP-induced liver injury were labelled with BrdU (1 mg, i.p.) one hour before sacrifice to label proliferating cells. Panels show representative immunofluorescence (IF) stains from each group as indicated. Nuclei are stained with DAPI and BrdU positivity was stained using anti-BrdU primary antibody (or isotype control antibody) before an Alexa Fluor 555 nm secondary antibody. Sections were imaged and quantified on an Operetta High Content Imaging System (Perkin Elmer). Sections were quantified by counting number of BrdU positive nuclei (red-stained nuclei, minimum fluorescent intensity 500 RFU in 546 nm channel) expressed as a percentage of total nuclei. BrdU quantification is shown (bottom right) in groups as open circles per individual animal around the mean (black line). Scale bar is indicated bottom-left per panel. Asterisks indicate statistical significance between groups ($P<0.05$, one-way ANOVA). (B) Co-immunostains indicate proliferating cells of parenchymal and non-parenchymal origin regenerate the liver in AAM mice.
Figure 3:
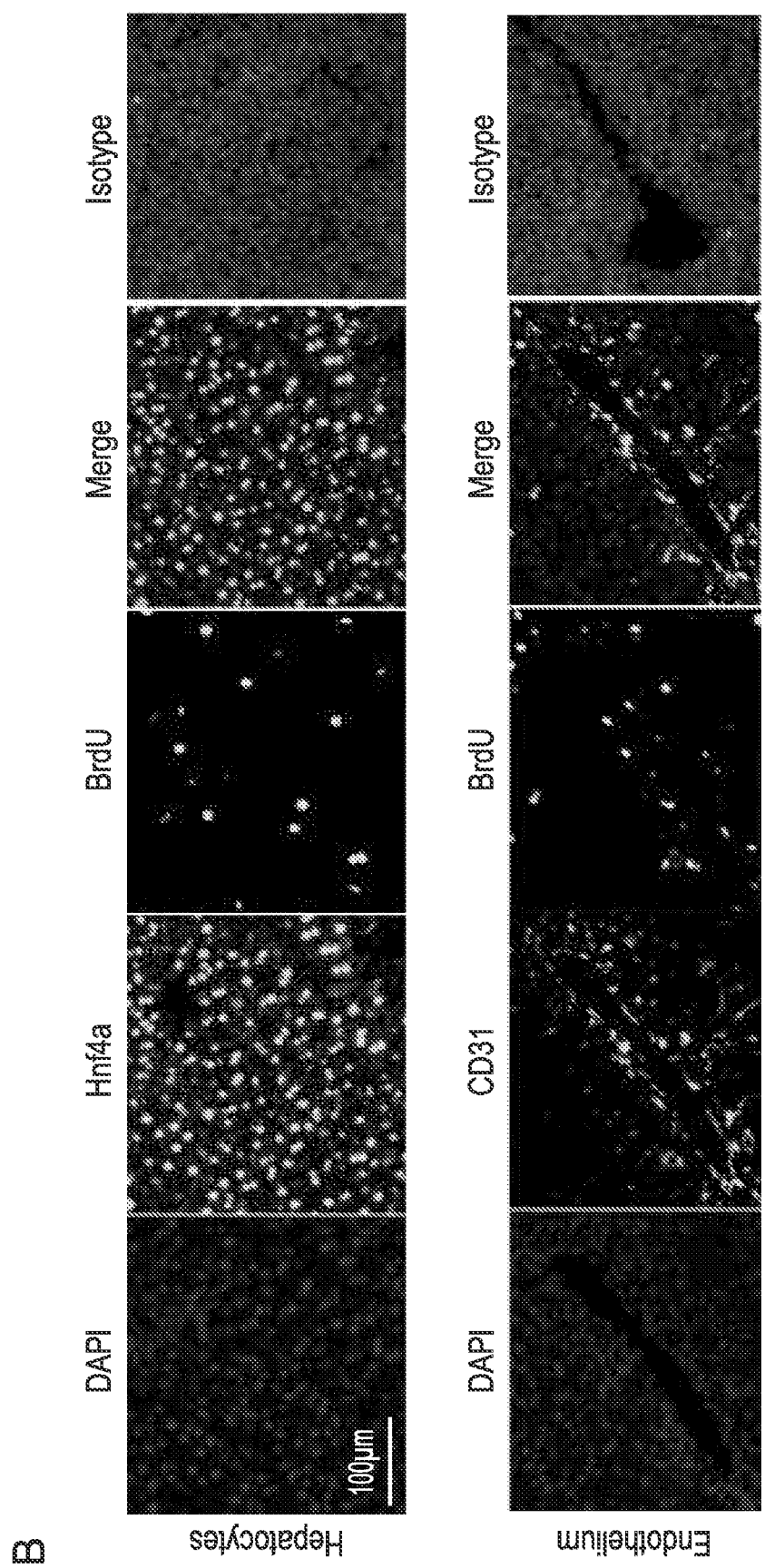

AAM treatment induces parenchymal and non-parenchymal proliferation following APAP-induced liver injury: We measured BrdU incorporation in liver 20 hours after macrophage therapy (36 hrs post-APAP). Mice were pulsed with 1 mg BrdU one hour before cull (i.p.) to label proliferating cells. Immunofluorescent (IF) sections were imaged on a high-content imaging system and BrdU positivity was confirmed by co-localisation with DAPI-stained nuclei to disregard background staining. IF analysis showed an 8.4-fold increase (P<0.05) in proliferating cells in the liver after AAM therapy (FIG. 3A). Proliferating cells were also 8.5 fold-higher (P=0.03) in mice treated with CAMs, but not DAMs, which although higher did not reach statistical significance. To understand the identity of the proliferating cells in AAM treated mice, we performed dual stains with Hnf4a (hepatocyte marker) and CD31 (endothelium maker). We observed most BrdU-positive cells colocalised with Hnf4a with a contribution of non-parenchymal cells around the central veins that were closely-associated with CD31 (FIG. 3B).

Figure 4:
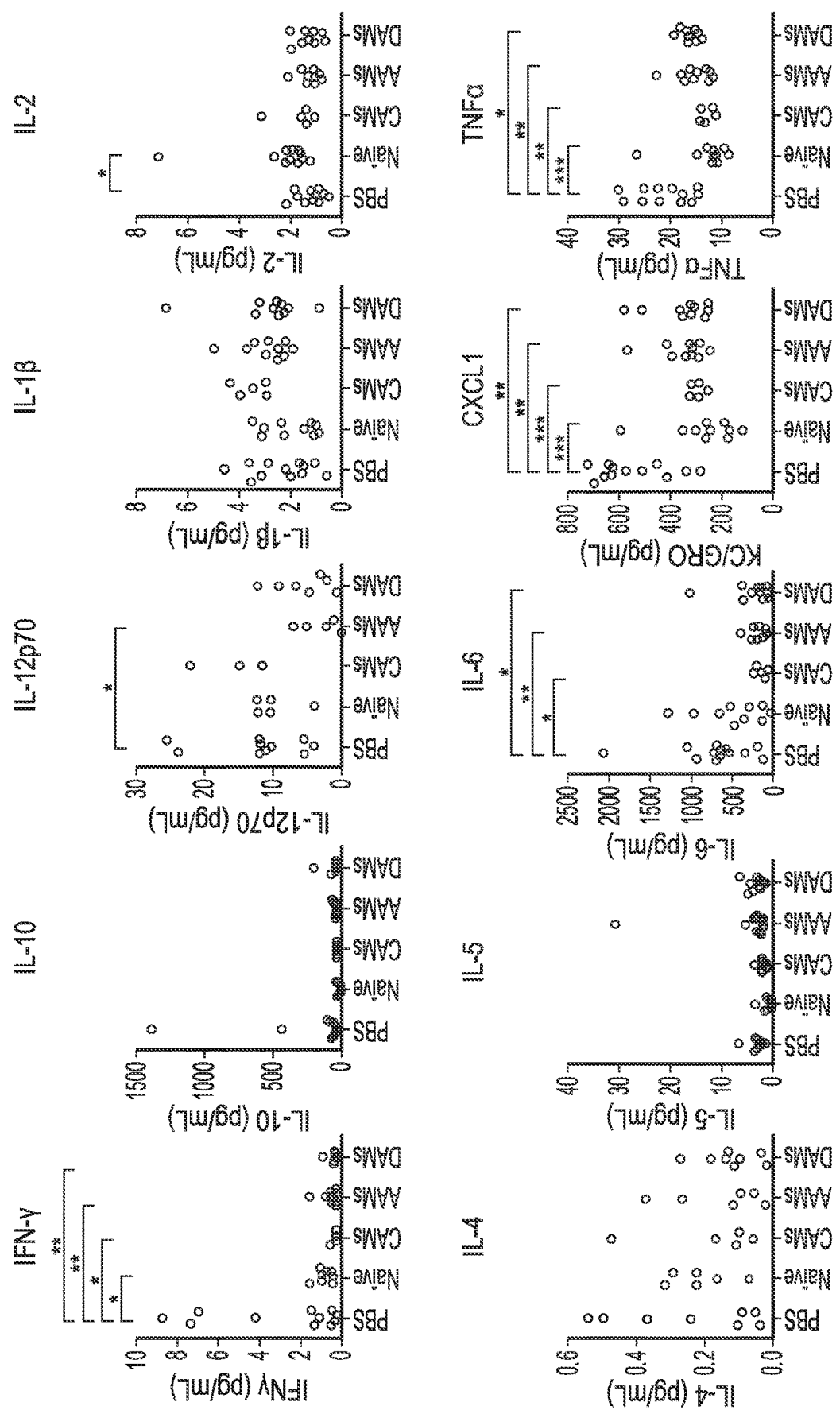
FIG. 4 shows polarised BMDM administration attenuates a panel of circulating inflammatory cytokines in mice with APAP-induced liver injury. Serum from mice receiving BMDMs (naïve BMDMs, CAMs and AAMs) was assayed for a 10-plex panel of pro-inflammatory cytokines using electrochemiluminescence technology (Meso Scale Discovery, Gaithersburg, Md.). Panels show data in groups for each cytokine analysed (IFN-γ, IL-10, IL-12p70, IL-1β, IL-2, IL-4, IL-5, IL-6, CXCL1 (KC/GRO), TNFα). Each open circle represents data points from individual animals per group. Asterisks represent levels of statistical significance (* $P<0.05$,  $P<0.01$, * $P<0.001$; one-way ANOVA).

A panel of circulating proinflammatory cytokines are lower in polarised-macrophage treated mice following APAP-induced liver injury: We posited that macrophages reduce the inflammatory response after injury to promote healing. To investigate this, we measured a 10-plex panel of inflammatory cytokines (IFN-γ, IL-10, IL-12p70, IL-1β, IL-2, IL-4, IL-5, IL-6, KC/GRO, TNF-α) in mouse serum harvested at 36 hours using electrochemiluminescence technology. Consistently, AAMs showed a substantial reduction in a panel of pro-inflammatory cytokines (FIG. 4) exhibiting reductions in IFN-γ (82%, P<0.01), IL-12p70 (73%, P=0.02), IL-6 (75%, P<0.01), CXCL1 (36%, P<0.01), and TNFα (27%, P<0.01). Reduced circulating pro-inflammatory cytokines were also observed in mice treated with both CAMs—IFN-γ (88%, P=0.03), IL-6 (80%, P=0.01), CXCL1 (45%, P<0.01) and TNFα (39%, P<0.01)—and DAMs—IFN-γ (86%, P<0.01), IL-6 (64%, P=0.01), CXCL1 (35%, P<0.01), TNFα (23%, P=0.02). Furthermore, mice treated with naive BMDMs showed reduction in some pro-inflammatory markers, albeit to a lesser extent than the polarised equivalents—IFN-γ (73%, P<0.01), CXCL1 (36%, P<0.01), TNF (23%, P<0.01). These data indicate that macrophages administered during the regenerative phase of APAP-poisoning exert an anti-inflammatory response, particularly in mice treated with AAMs.

Figure 5:
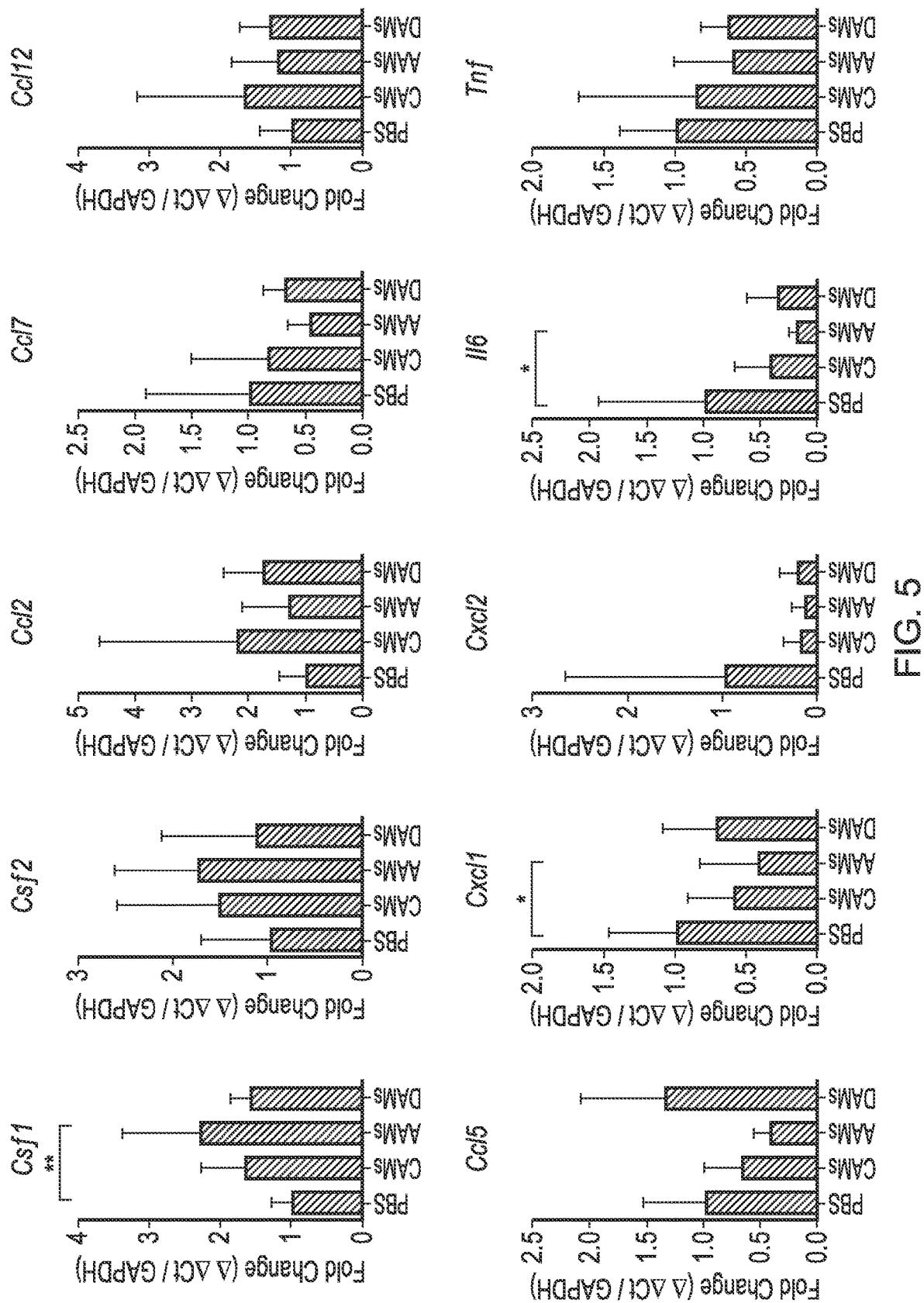
FIG. 5 shows AAM administration upregulates Csf1 expression and reduces inflammatory Cxcl1 and Il6 expression in mice following APAP-induced liver injury. A panel of cytokines and chemokines known to be implicated in macrophage signaling during ALI was assayed in whole liver following BMDM-treatment for APAP-induced liver injury. Panels show the mean relative expression of each gene in groups relative to mice who received PBS following APAP administration (no BMDMs). The black bars show the mean fold-difference around the standard deviation (n=6). Expression of pro-survival gene Csf1 was significantly higher in AAM-treated mice. Consistent with circulating markers, expression of Cxcl1 and Il6 was significantly lower in AAM-treated mice. Gapdh served as the housekeeping gene. Asterisk indicates statistical difference (P<0.05; one-way ANOVA).
Figure 6:
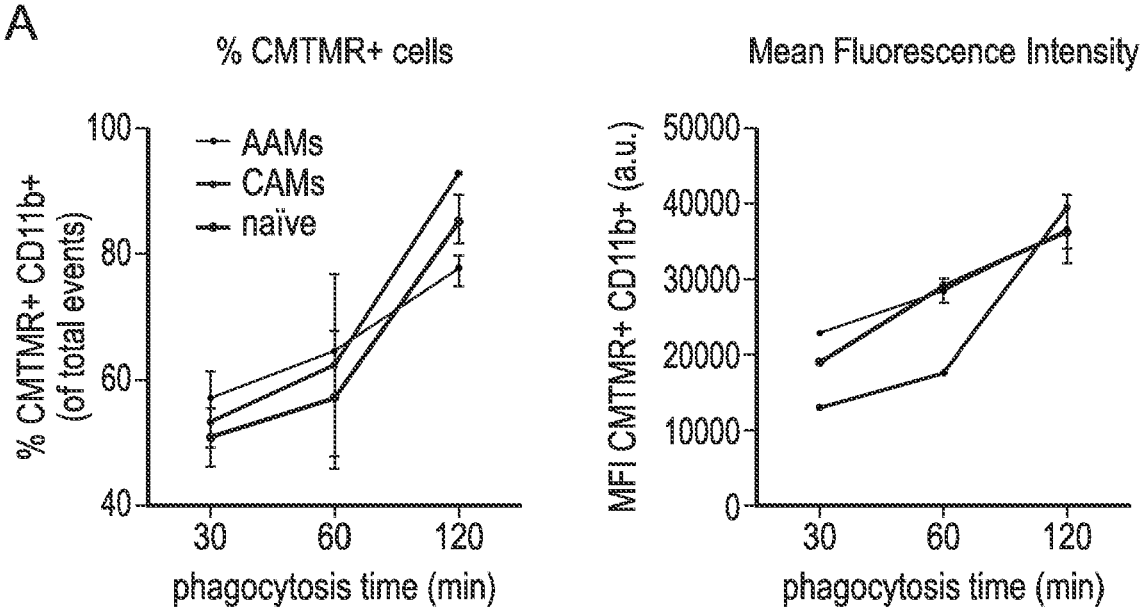
FIG. 6 shows AAMs exhibit enhanced phagocytic capacity over naïve- and CAMs. (A) Polarised BMDMs were incubated with apoptotic fluorescent thymocytes. BMDMs were incubated with apoptotic thymocytes (primary thymocytes harvested from 3-5 week old C57BL6 mice, treated with 1 µM hydrocortisone, as previous (D. A. Ferenbach et al., 2010). Apoptotic thymocytes were labelled using CMTMR (Invitrogen) according to the manufacturer's instructions (L. Bosurgi et al. 2015) and then incubated with BMDMs polarised towards different phenotypes (green, AAMs; red, CAMs; black, naïve) for 30, 60, or 120 minutes. Panels show the percentage of CMTMR-positive BMDMs (left), their mean fluorescent intensities (MFIs; second from left), the normalised MFI (second from right), and the MFI histogram (right). The pale blue histogram represents unstained cells. (B) Ly6C expression on BMDMs is reduced following phagocytosis in AAMs. Left panel shows the percentage of Ly6C-positive BMDMs polarised towards different phenotypes, right panel shows representative histogram. (C) AAMs phagocytose more zymosan-coated pHrodo particles than naïve or CAMs. BMDMs were incubated with zymosan-coated pHrodo bioparticles for up to 125 mins and analysed in real-time via high-content imaging. Graph shows the mean fraction of cells that are above the fluorescent threshold (positive for phagocytosis) around the standard deviation in groups (green, AAMs; red, CAMs, black, naïve) over time. (D) Representative images taken at different times show AAMs exhibit green fluorescence earlier and to a greater capacity than naïve macrophages or CAMs. Cells are visualised with blue nuclei stain (NucBlue) and DeepRed Cell Mask.
Figure 6:
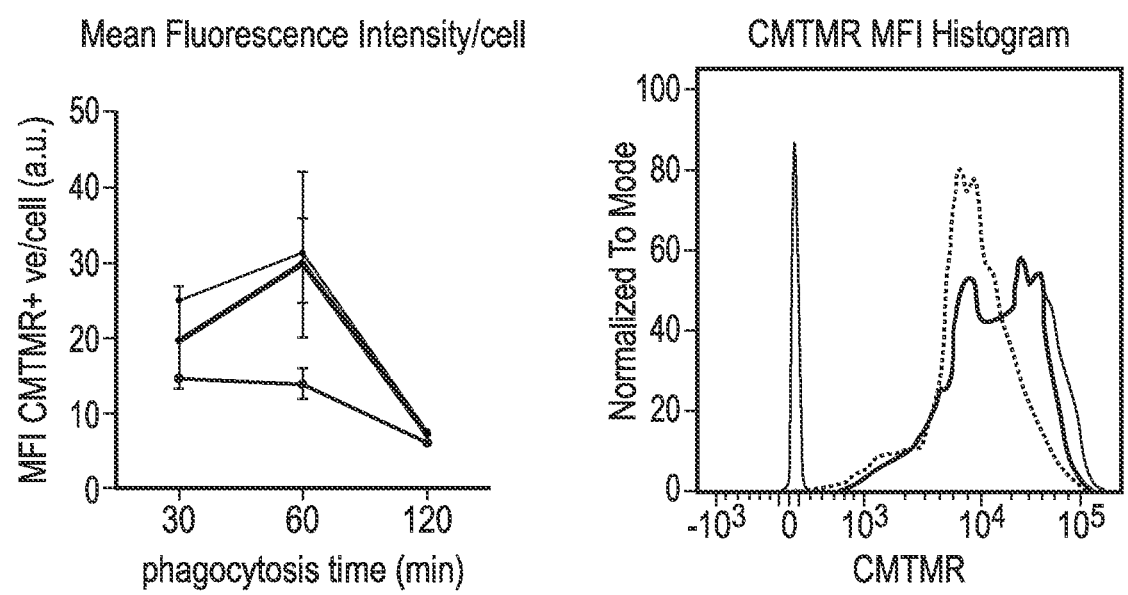
Figure 6:
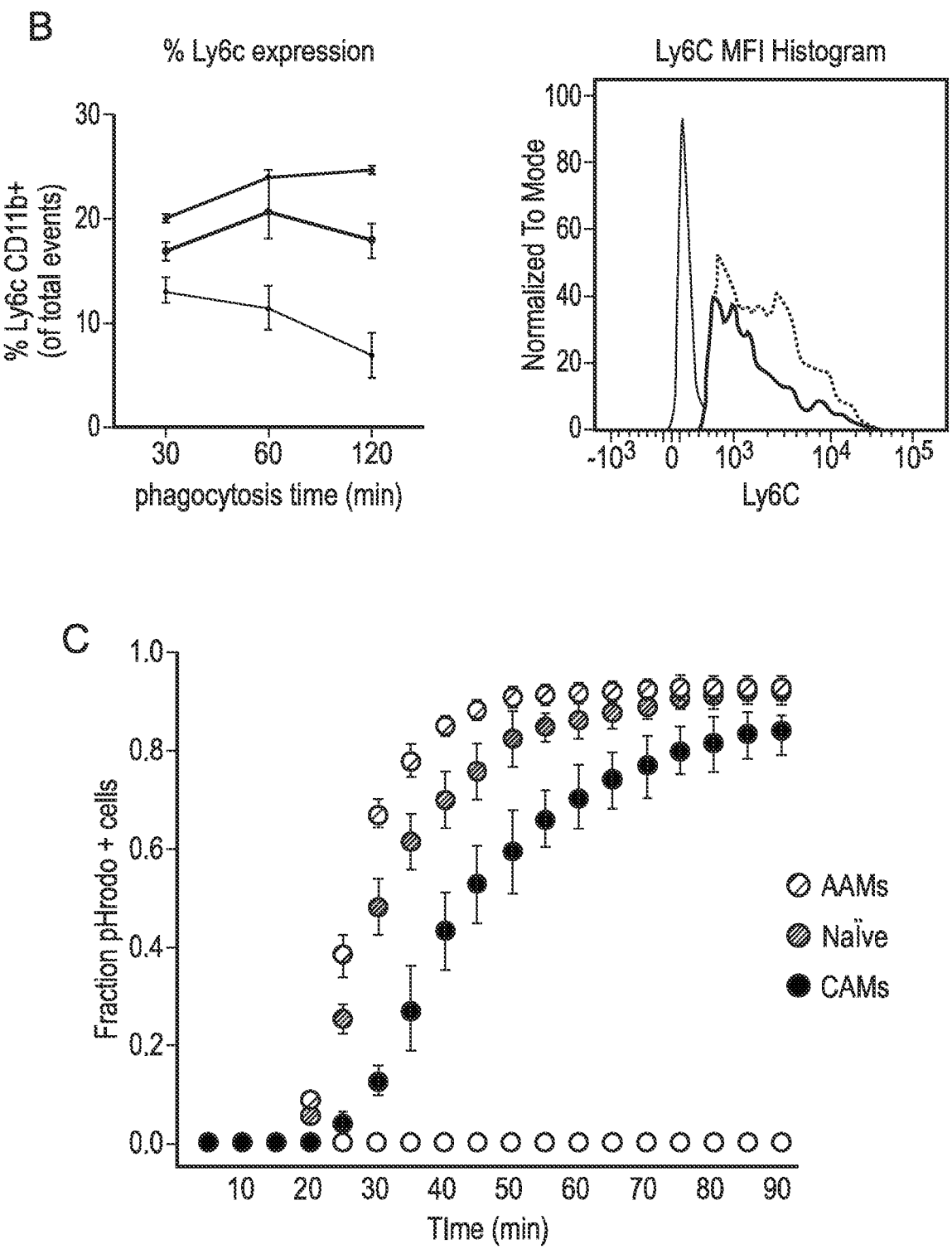
Figure 6:
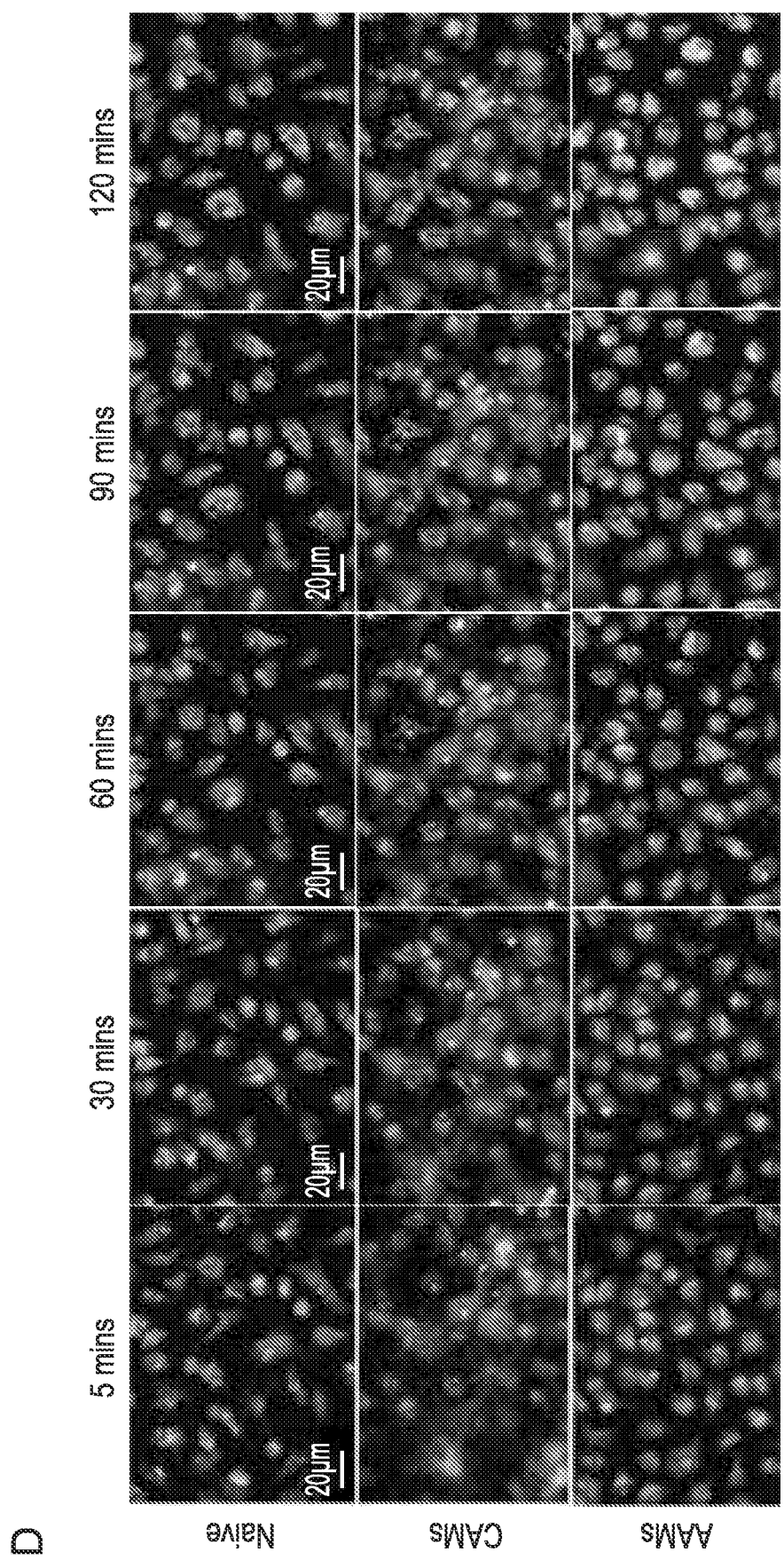

Further, we measured the expression of a panel of genes (Csf1, Csf2, Csf3, Ccl2, Ccl3, Ccl5, Ccl7, Ccl12, Cxcl1, Cxcl2, Il-6, Tnf and Tgfβ) in whole liver tissue implicated in inflammation and/or repair via qPCR. This showed an average 2.3-fold increase (P<0.01) in pro-survival Csf1 gene expression in AAM treated mice versus vehicle control (FIG. 6). Consistent to this, the only significant changes we observed were in the same group of animals which showed a reduction in pro-inflammatory genes Cxcl1 (2.4-fold, P<0.05) and Il-6 (5.8-fold, P<0.05). This data explains the histological differences observed between groups (FIG. 3B), in which only AAMs provide a significant reduction in necrotic area. Furthermore, the gene expression data of the proinflammatory cytokines Cxcl1 and IL-6 reflect the circulating profiles at the protein level (FIG. 5).

AAMs display increased phagocytic rate and capacity in vitro: We measured phagocytosis of BMDMs polarised to different phenotypes in vitro. After incubation of polarised BMDMs with fluorescently-labelled apoptotic thymocytes, we observed a non-significant trend that more AAMs had phagocytosed (11% increase vs naïve, 7.3% increase vs M1) after 30 mins phagocytosis, but this difference plateaued after 60 and 120 minutes (FIG. 6A). Furthermore, there was a significant increase in the mean fluorescence intensity (MFI) in AAMs at 30 mins versus other groups (21% increase vs naïve, 75% increase vs CAMs, data plotted in histogram) and a 64% increase versus CAMs macrophages at 60 mins. A higher MFI in AAMs (67% increase vs CAMs) after normalisation to cell number is observed. The percentage of BMDMs that express the inflammatory marker Ly6C, a classical inflammatory myeloid surface marker was measured. AAMs have a significantly lower percentage of Ly6C positive cells at 30 mins (22% lower vs naïve, 34% vs CAMs), 60 mins (44% lower vs naïve, 52% vs CAMs), and 120 mins (61% lower vs naïve, 72% vs CAMs; FIG. 6B).

A real-time phagocytosis assay to monitor phagocytosis of pH-sensitive fluorescent microbeads coated with zymosan (a glucan present in yeast) using polarised BMDMs was performed. Concordant to flow cytometry analysis, an increased percentage of pHrodo positive cells in AAMs over time was observed, which plateaued approaching 90 minutes (FIG. 6C). Representative images are provided showing an increased phagocytic rate and capacity in AAMs versus naïve and CAMs (FIG. 6D).

Figure 7:
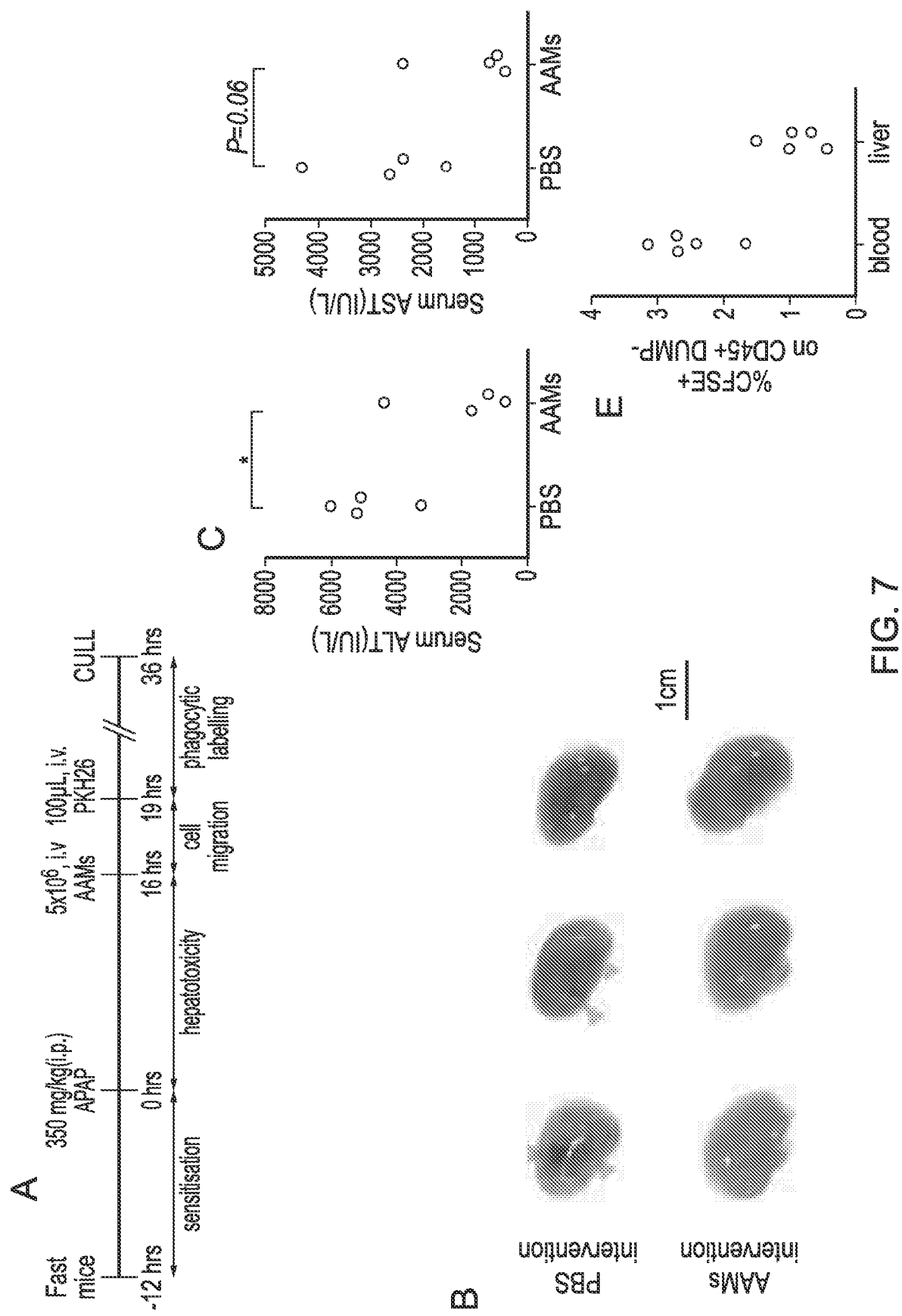
FIG. 7 shows transplanted AAMs are highly phagocytic in vivo and retain their anti-inflammatory phenotype. (A) Study design timeline shows a single APAP administration to fasted mice before BMDM transplantation 16 hrs post-APAP. Phagocytic capability of endogenous and exogenous cells was assessed by a challenge of PKH26 dye (i.v.; dye ingested exclusively by phagocytic cells) before culling at 36 hours post-APAP. (B) Photographs of presentative left lateral lobes in petri-dishes from mice receiving PBS (top row) or AAMs (bottom row). Focal regions of haemorrhagic necrosis are observed in PBS-treated mice following APAP (blue arrowhead) which are not observed in livers of macrophage-treated mice. (C) Serum transaminases are substantially reduced in mice receiving BMDM therapy (ALT, left panel; AST, right panel) (D) Upper panels show macrophage-treated mice exhibit a modest reduction in Ly6C+ infiltrating macrophages in the liver, panel shows the percentage (left) and absolute number (right) of infiltrating cells. Lower panels show a trend to suggest that the Ly6C+ macrophages have a higher phagocytic activity in the liver of macrophage-treated mice (left panel, percentage; right panel absolute number). (E) Transplanted BMDMs are detected in both blood and liver in high numbers 20 hrs post-transplantation. (F) The majority of BMDMs detected in the liver are Ly6C negative, suggesting most cells retain their anti-inflammatory phenotype (G) Transplanted macrophages exhibit substantial phagocytic activity in the liver, phagocytosis was gated on CFSE+ and PKH26+ macrophages. Over 95% of Ly6C- BMDMs are positive for phagocytosis confirming high phagocytic activity in vivo.
Figure 7:
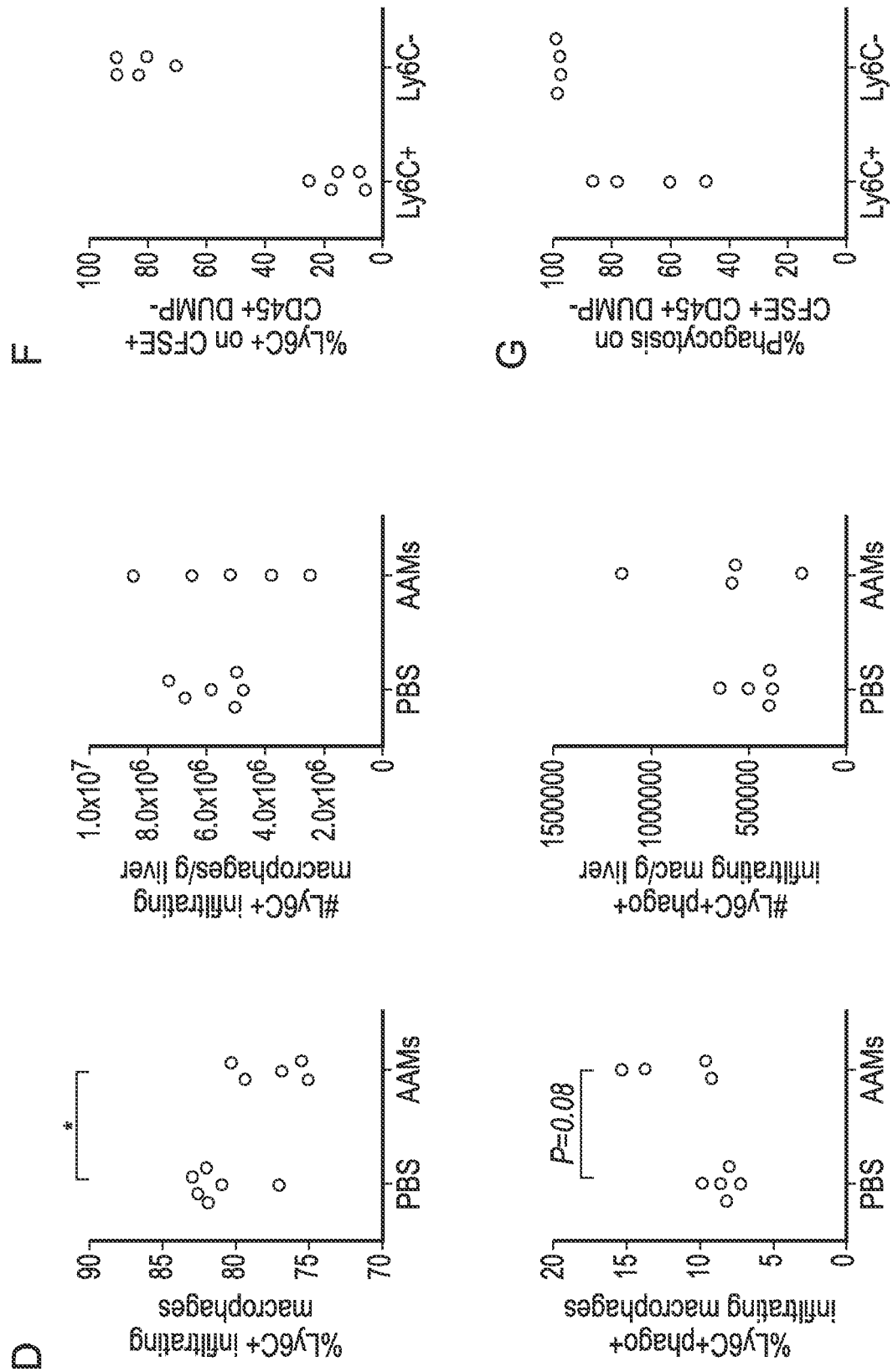

AAMs are highly phagocytic and retain an anti-inflammatory phenotype in vivo: An in vivo phagocytosis experiment was performed to characterise AAMs post-transplantation. CFSE-labelled AAMs were transplanted (5×10⁶, i.v.) to mice 16 hours after APAP administration. Three hours later, mice were challenged with an i.v. administration of PKH26 (a red fluorescent dye for specific labelling of phagocytes) to label endogenous and exogenous macrophages (see FIG. 7A for study design). Gross histological abnormalities in mice receiving vehicle only was observed, characterised by punctate areas of haemorrhagic necrosis which were largely absent in AAM-treated mice (FIG. 7B). Serum chemistry analysis showed a significant reduction serum transaminases (59% lower ALT, 75% lower AST) in AAM-treated mice (FIG. 7C).

A modest but statistically significant reduction in the percentage of infiltrating inflammatory macrophages in the liver of BMDM-treated mice was observed (FIG. 7D) which corresponded with an increased trend of phagocytic cells in these inflammatory cells (P=0.08). Transplanted AAMs in both liver and blood 20 hours after i.v. transplantation were detected, accounting for approximately 1% of the liver leukocytes harvested during liver digestion (FIG. 7E). Of the transplanted AAMs, 83% of those detected were Ly6Clo, confirming these cells retain their anti-inflammatory phenotype in vivo (FIG. 7F). The percentage of transplanted cells that had phagocytosed PKH26 based on their Ly6C expression was measured. 70% of Ly6Chi cells, and over 98% of Ly6Clo cells were PKH26 positive suggesting transplanted AAMs are highly phagocytic in situ.

Discussion

APAP poisoning is a common reason to attend hospital accounting for many thousands of emergency room admissions in the United States and United Kingdom per annum. The mainstay of treatment involves early administration of NAC, a sulfhydryl donor, to boost the antioxidant capacity in the liver before widespread injury occurs. However, the effectiveness of this antidotal therapy is profoundly diminished in patients who present later where liver necrosis may already be established. APAP poisoning represents the leading cause of ALF in the United States with liver transplantation the only effective therapy. Therefore, there is a clinical need to identify and develop novel therapeutic strategies to treat patients with bona fide liver injury in order to reduce the risk of ALF. Furthermore, a treatment to expedite recovery from ALI and reduce the associated costs and clinical expenditure would also be highly beneficial.

We tested a potential cell therapy for livery injury (such as ALI). Macrophages are involved in the clearance of both apoptotic and necrotic cells in vivo. However, KCs (liver resident macrophages) become depleted during APAP-ALI causing a deficit in innate immunity (8). Macrophages have previously been investigated as a potential cell therapy for other disease indications including diabetes (30), renal fibrosis (31), pulmonary disorders (32), and malignancies (33) but have not yet been evaluated in the context of liver injury (such as ALI). Invasive surgery is not practical in the APAP model due to potential coagulopathy, however it would be essential to deliver a therapy to the site of injury rapidly due to the fulminant nature of the disease. Therefore, we delivered BMDMs intravenously (via tail vein) to the liver and spleen within four hours in healthy and APAP poisoned mice. We observed a reduction in BMDM engraftment in APAP-treated mice compared to healthy controls. This may be due to an infiltrated niche or perturbed hepatic microcirculation that is a hallmark of APAP-ALI (34). The lung is another obstacle for cells after i.v. injection, but macrophages are suited for peripheral administration due to their relatively small size. In fact, we did not observe any macrophages in the lung 20 hours after administration suggesting that lung localisation is temporary after a bolus injection. Nevertheless, pulmonary embolism remains a safety concern. Therefore, other non-invasive administration routes could be used. I.v. administration of 1×10⁶ BMDMs in healthy mice appeared safe resulting in no change to any index of blood chemistry and did not change any haematological parameter in APAP-treated mice upon delivery of 5×10⁶ cells (data not shown).

Hepatocyte death during APAP-ALI is the priming event of the activation of the innate immune system, through release of inflammatory mediators and danger associated molecular patterns (DAMPs), e.g. HMGB1 (35). The uncontrolled systemic activation of the innate immune system can lead to multiorgan failure and death, clinically recognised as SIRS which is a key determinant of clinical outcome (7). Administration of AAMs in our mouse model led to reductions in circulating proinflammatory cytokines known to be elevated during human ALF (36, 37). Furthermore, clearance of necrotic material may be delayed in APAP-ALI since endogenous KCs are also lost during the initial injury resulting in a diminished hepatic innate immune capacity (8). Replenishment of this innate immune capacity via adoptive transfer of phagocytes may limit the inflammatory signals released from dying cells, or from gut-derived pathogens, in order to reduce systemic inflammation, and prevent progression towards ALF. One potential safety concern of macrophage-therapy for livery injury is the potential for transplanted macrophages themselves become pro-inflammatory and exacerbate inflammation and injury, however, we found that once primed in culture to an alternatively-activated phenotype, the transplanted AAMs retained their anti-inflammatory phenotype in vivo at least for 20 hours (FIG. 7F).

Liver regeneration following APAP-ALI is an important feature in the resolution of injury. We found an 8-fold increase in the number of proliferating cells at 36 hours post-APAP suggesting AAM therapy accelerates the regenerative response. This demonstrates that AAMs may have utility in treating various causes of liver injury.

Dual staining revealed proliferating cells were of hepatocellular (Hnf4a positive) and endothelial (CD31 positive) origin. Centrilobular hepatocytes are the main site of injury, since these CYP2E1-positive cells generate the toxic metabolite of APAP, N-acetyl-p-benzo-quinoneimine (NAPQI) that ultimately causes cell death. However, liver sinusoidal endothelial cells are also known to become perturbed during APAP-ALI (38, 39). Regeneration of the both the parenchyma and the vasculature are perhaps key mechanisms during AAM-mediated repair of the liver.

Without wishing to be bound by theory, we hypothesise that AAMs remove necrotic material due to their highly phagocytic phenotype. CAMs, which display a diminished phagocytic capacity, also partly reduced inflammation and stimulated proliferation, albeit to a lesser extent than AAMs. It is possible that transplanted BMDMs provide a therapeutic secretome and deliver trophic factors to reduce inflammation or promote liver regeneration in situ.

The longevity of transplanted BMDMs in the liver is likely to be transient. Previous work has showed that transplanted BMDMs are detectable for at least 7 days after transplantation in fibrotic liver via direct hepatic portal vein injection (18). Our group have also used SPIONs to detect BMDMs via MRI not more than 3 weeks in healthy mice. (data not shown). The transient nature of these cells might be beneficial to allow the natural clearance of transplanted cells over several weeks permitting the liver to return to its normal physiological condition. Nor is the transient nature of this therapy a concern since the therapeutic window is likely to occur within the first 48 hours post-transplantation. Nevertheless, the pharmacokinetics of this cell based therapy could be optimised to compare multiple rounds of BMDM administrations, if necessary, or supply a constant infusion of BMDMs to reduce the risk of embolism.

APAP poisoning is a medical emergency which can lead to ALF devastatingly quickly. This is in contrast to other liver diseases such as liver fibrosis where patients can be monitored for weeks and months before and after treatment allowing time for cell harvest, expansion, characterisation, and re-infusion. In the case of an emergency clinical situation with ALI, an existing bank of macrophages could be set up so that AAMs could be administered immediately in an intensive care unit. Huge advances in the stem cell field have recently described macrophages derived from human induced pluripotent stem cells (iPSCs) that recapitulate the biology and function of primary equivalents (40-42). It is conceivable that AAMs derived from these cells could represent a viable cell therapy.

In summary we have shown that by polarising BMDMs with defined factors to a highly phagocytic phenotype, these cells can serve as a cell therapy to stimulate cell proliferation, reduce systemic inflammation, and ameliorate necrotic lesions in liver injury (e.g. during the regenerative phase of APAP-ALI). AAMs may represent a promising cytotherapy to expedite liver tissue repair that has translational potential.

Example 2

Murine Embryonic Stem Cell Derived Macrophages (ESDM)

Key points:
- ESDMs reduced fibrosis in a murine model of liver injury and stimulated a ductular response, features seen with BMDM therapy
- ESDM show some similarity to tissue-resident macrophages, possibly reflecting their developmental origin.
- ESDMs repopulated the Kupffer cell compartment of mice that had been depleted of macrophages using liposomal clodronate
- A novel live cell imaging technique has been developed to quantify phagocytosis using which we demonstrate differences in the phagocytic index of embryonic stem cell derived- and bone marrow derived macrophages.

We demonstrate that pure populations of macrophages can be produced from mouse ESCs in vitro at scale and that these cells have the capacity for repair in vivo in a murine model of liver fibrosis. ESC-derived macrophages can be distinguished from their bone marrow derived counterparts in phagocytic activity and in the expression of key functional markers supporting the recent study suggesting that PSC-derived macrophages are developmentally related to tissue resident macrophages including Kupffer cells and Langerhans cells (Buchrieser, J., James, W. & Moore, M. D. Human Induced Pluripotent Stem Cell-Derived Macrophages Share Ontogeny with MYB-Independent Tissue-Resident Macrophages. Stem Cell Reports 8, 334-345). We show that ESC-derived macrophages are able to repopulate the Kupffer cell compartment of macrophage-depleted livers efficiently and thus provide an effective strategy to study the role of tissue resident macrophages in tissue repair.

Results

A Comparison of Embryonic Stem Cell Derived- and Bone Marrow Derived Macrophages.

Figure 16:
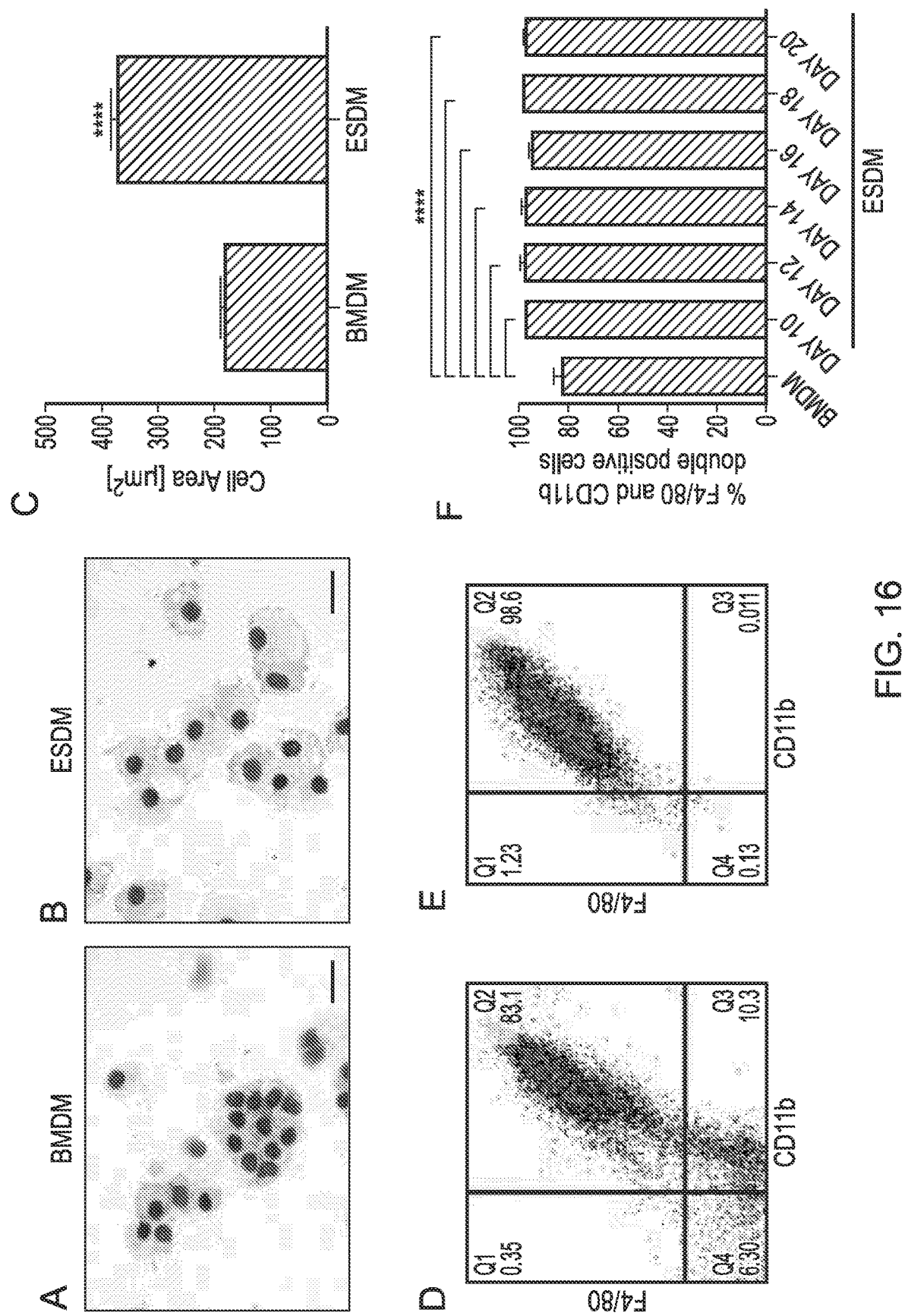
FIG. 16 shows a comparison of ESDMs and BMDMs. Stained cytospins of BMDMs (A) and ESDMs (B) with image analyses demonstrating that ESDMs are larger (C) (Scale bars 30 μM). Flow cytometry analyses of BMDMs (D) and ESDM (E) demonstrating a pure population in ESDMs. Images from live phagocytosis assay of BMDMs (G) and
ESDMs (H) at 0 (I), 50 (II, 100 (III) and 150 (IV) minutes after the addition of Phrodo beads and quantification of rate of phagocytosis using Harmony image analysis software (I) (Scale bars 50 μM). [*<0.05, p<0.01, *p<0.001, ****p<0.0001; n=3, (C) Unpaired t-test, (F) One-way ANOVA with Kruskal-Wallis test, (I) Two-way ANOVA with Sidak's multiple comparison test]
Figure 16:
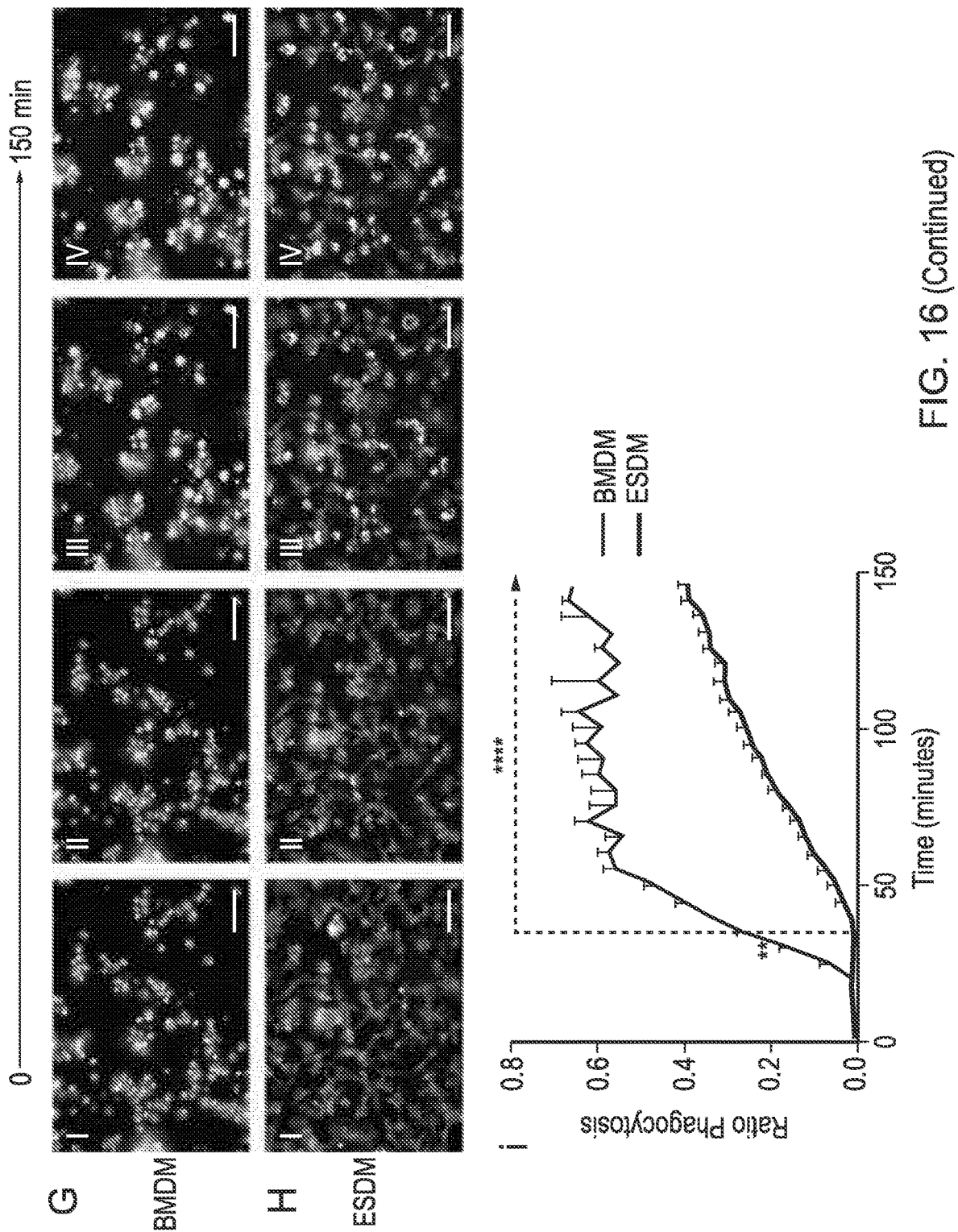

We produced macrophages from embryonic stem cells (ESC) using our published method (Zhuang, L. et al. Pure populations of murine macrophages from cultured embryonic stem cells. Application to studies of chemotaxis and apoptotic cell clearance. J Immunol Methods 385, 1-14, doi:10.1016/j.jim.2012.06.008 (2012)) and directly compared their phenotype and function with classic bone marrow derived macrophages (BMDMs), the gold-standard source of primary macrophages. Briefly, ESC were grown in the presence of CSF-1 and IL-3 to form embryoid bodies (EB). EBs adhere to tissue culture plastic and release non-adherent macrophage progenitor cells into the medium. These cells are harvested and plated onto non-treated Petri dishes in the presence of CSF-1 alone. They give rise to macrophages that adhere to the plastic and form a monolayer. Embryonic stem cell derived macrophages (ESDMs) and BMDMs had a comparable morphology but ESDMs appeared slightly larger in size than BMDMs (FIG. 16A-C). Flow cytometry analyses revealed that over 90% of ESDMs were double positive for the macrophage markers, F4/80 and CD11b, and that cells derived from different time points during the differentiation process (day 10 to 20) demonstrated comparable levels of cell surface marker expression (FIG. 16E, F). In comparison, the population of BMDMs had a slightly lower percentage of double positive F4/80 and CD11b cells indicating BMDMs generated in this protocol were more heterogeneous than ESDMs (FIG. 16D, F).

To compare the phagocytic activity of ESDMs and BMDMs, we developed a novel live imaging assay using the Operetta High-Content Imaging system (Perkin Elmer) which is fully automated and thus eliminates operator bias out of imagining and analysis. In this assay pH-sensitive pHrodo™ Bioparticles were used that only fluoresce within the acidic intracellular environment (Thermo Fisher Scientific). This assay allowed us to quantify amount as well as rate of uptake of bioparticles in real time. Cells were stained with a Deep Red Plasma Membrane stain and NucBlue Live ReadyProbes reagent, incubated with pHrodo™ bioparticles and imaged every 5 minutes for 2.5 hours using the Operetta High-Content System (FIG. 16G, H). An increase in the number of fluorescing cells was observed over time in both cell types but the phagocytosis rate of ESDMs was significantly lower than BMDMs (FIG. 16I). Our previous work using flow cytometry indicated that there was no significant difference in phagocytic activity between BMDMs and ESDMs whereas this sensitive, real time strategy has uncovered subtle differences.

Figure 17:
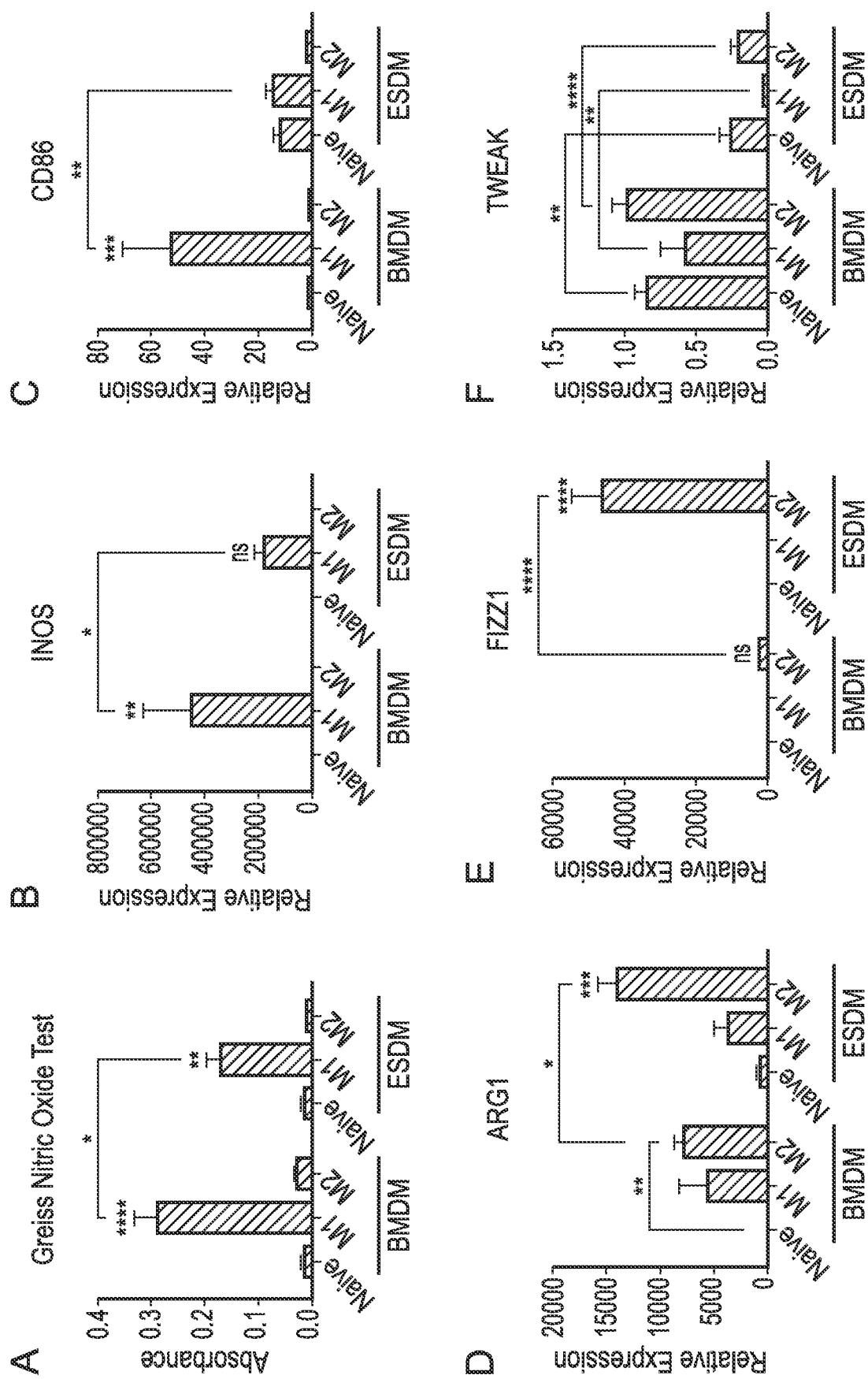
FIG. 17 shows M1 and M2 stimulation of ESDMs and BMDMs. Griess Nitric oxide assay of naïve, M1 and M2-stimulated BMDMs and ESDMs (A), and expression of key markers by qRT-PCR analyses, iNos (B) and Cd86 (C) as markers of M1, Arg1 (D) and Fizz1 (E) as markers of M2 phenotypes, and Tweak (F), Mmp9 (G), Mmp12 (H), and Mmp13 (I) as markers of tissue remodeling. Quantification of phagocytosis of M1-and M2-stimulated BMDMs (J) and ESDMs (K). [*p<0.05, p<0.01, *p<0.001, ****p<0.0001; n=3 per group, Two-way ANOVA with Tukey's multiple comparison test].
Figure 17:
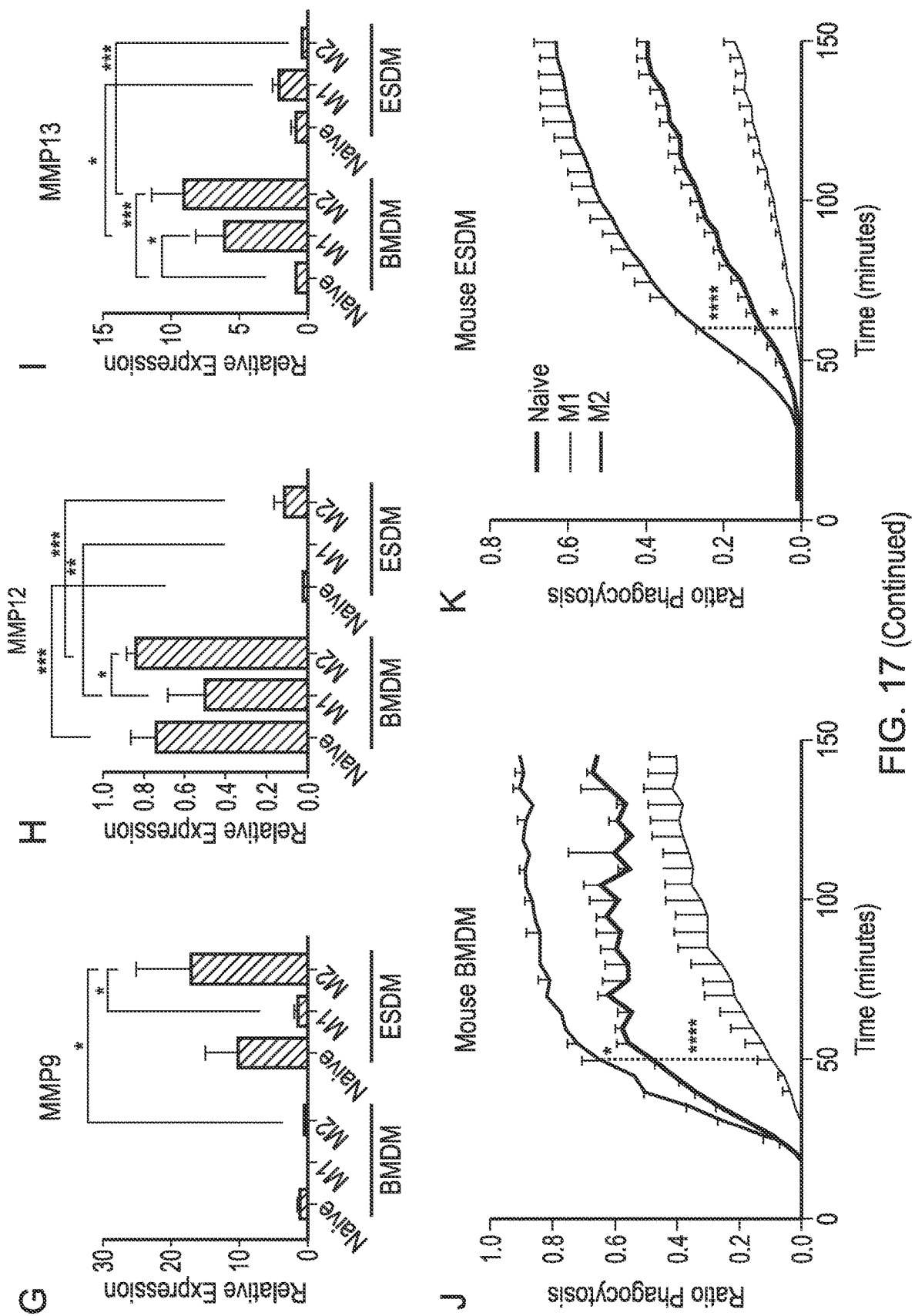

ESDMs and BMDMs were primed in vitro to adopt a M1- or M2-like phenotype by treating them with LPS and IFNγ or IL-4, respectively. There was a significant increase in nitric oxide (NO) production upon LPS/IFNγ-stimulation from both BMDM and ESDMs but the activation level of ESDMs was not as high as BMDMs (FIG. 17A). This was confirmed by the lower level of expression of M1-related genes, iNos and Cd86 (FIG. 17B, C) in ESDMs. In contrast, the response of ESDMs to IL4 was significantly higher than BMDMs as assessed by the increased expression of the M2-related genes, Arg1 and Fizz1 (FIG. 17D, E). Markers of tissue regeneration such as Tweak, Mmp12 and Mmp13 were lower in ESDMs compared to BMDM whereas Mmp9 was expressed at a higher level (FIG. 17F-I)

We used our novel imaging strategy to compare the phagocytic activity of M1- and M2-polarised ESDM and BMDM. LPS-IFNγ stimulation reduced and IL4 increased the rate of phagocytosis in both cell types but, ESDMs had a lower rate of phagocytosis in their stimulated cultures compared to the equivalent cultures of BMDMs (FIG. 17J, K).

Taken together these data demonstrate that the phenotype of ESDMs can be modified in a comparable manner to BMDMs but subtle differences in the extent of their response to polarization.

ESDMs as an Effective Cell Therapy in a Murine Model of Liver Fibrosis

We next tested whether ESDMs could have a therapeutic effect in a murine model of liver injury. Mice were treated with carbon tetrachloride $CCl_4$ twice weekly for four weeks with a proportion being randomly selected to receive either 10 or $20 \times 10^6$ ESDM intravenously at the start of the second week. Mice were sacrificed 21 days after ESDM injection and livers were processed for immunohistochemistry (FIG. 18A).

Figure 18:
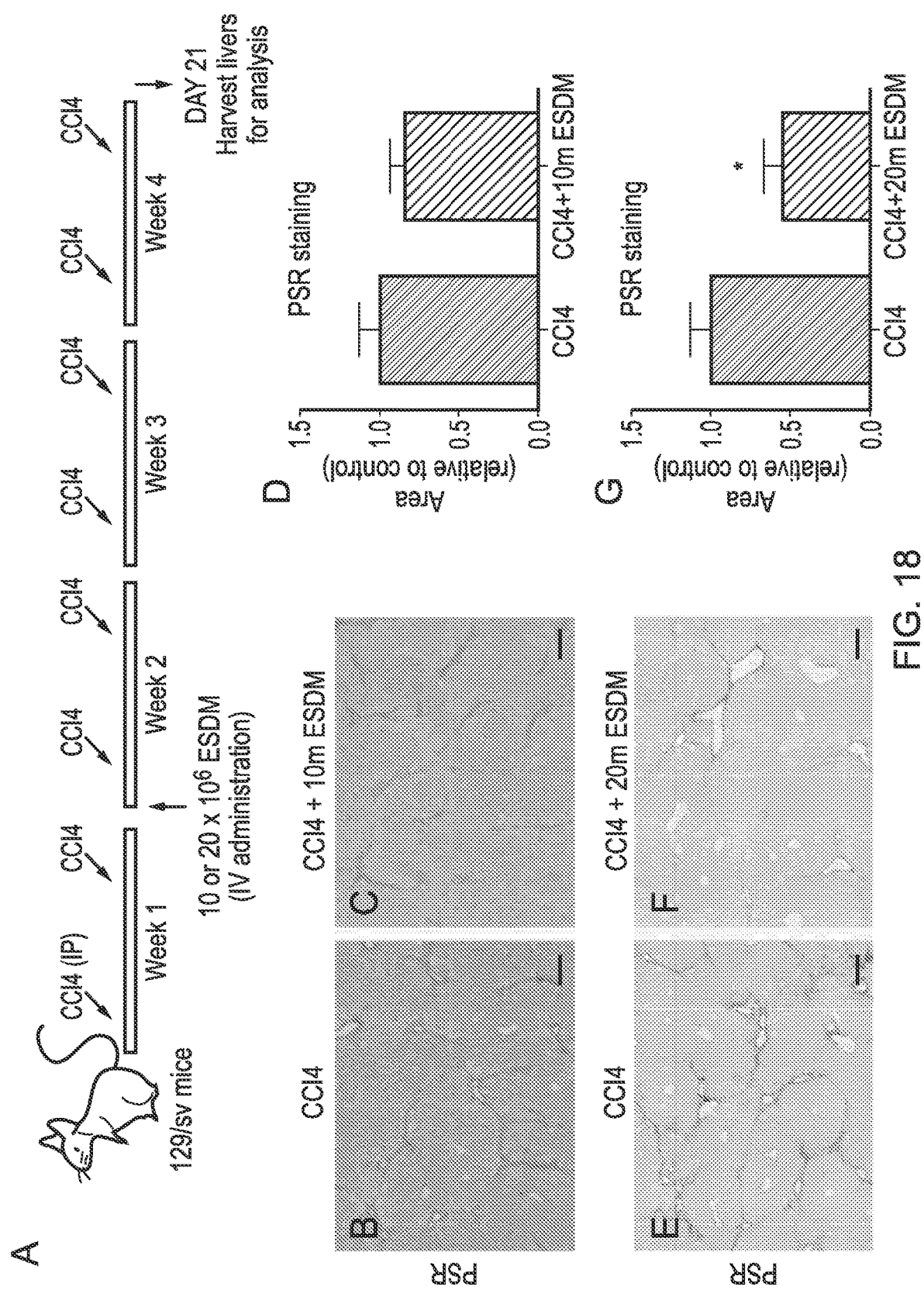
FIG. 18 shows that higher dose of ESDMs has an anti-fibrotic effect. Schematic (A) of injury and macrophage injection of 10 or 20 million macrophages. PSR staining (B-G) and aSMA staining (H-M) of liver sections from CCl4-treated livers that were injected with either 10 million (10 m) or 20 million (20 m) ESDMs. Scale bars 200 μM. [*p<0.05, n=5 per group, Unpaired t-test].
Figure 18:
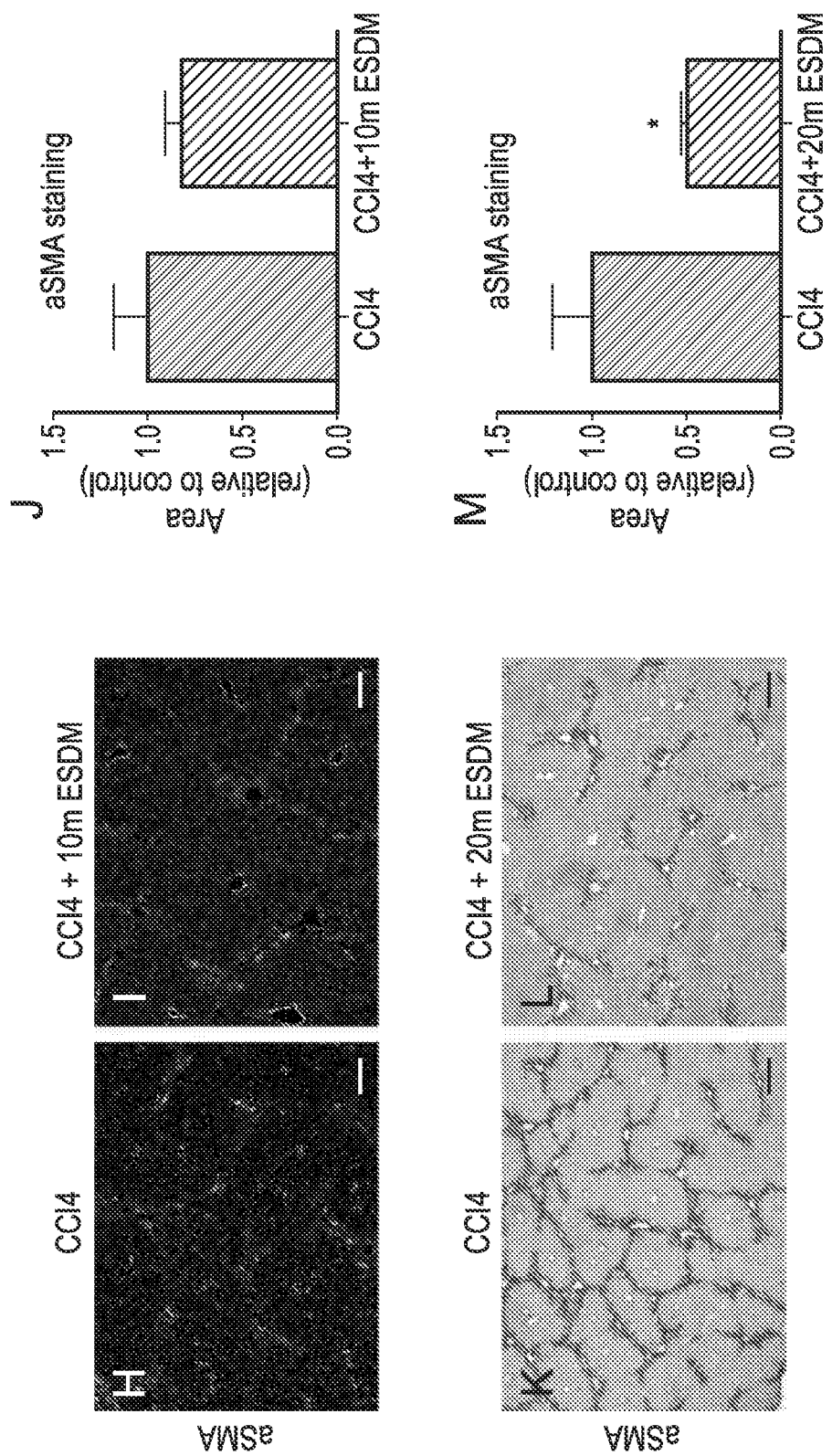
Figure 19:
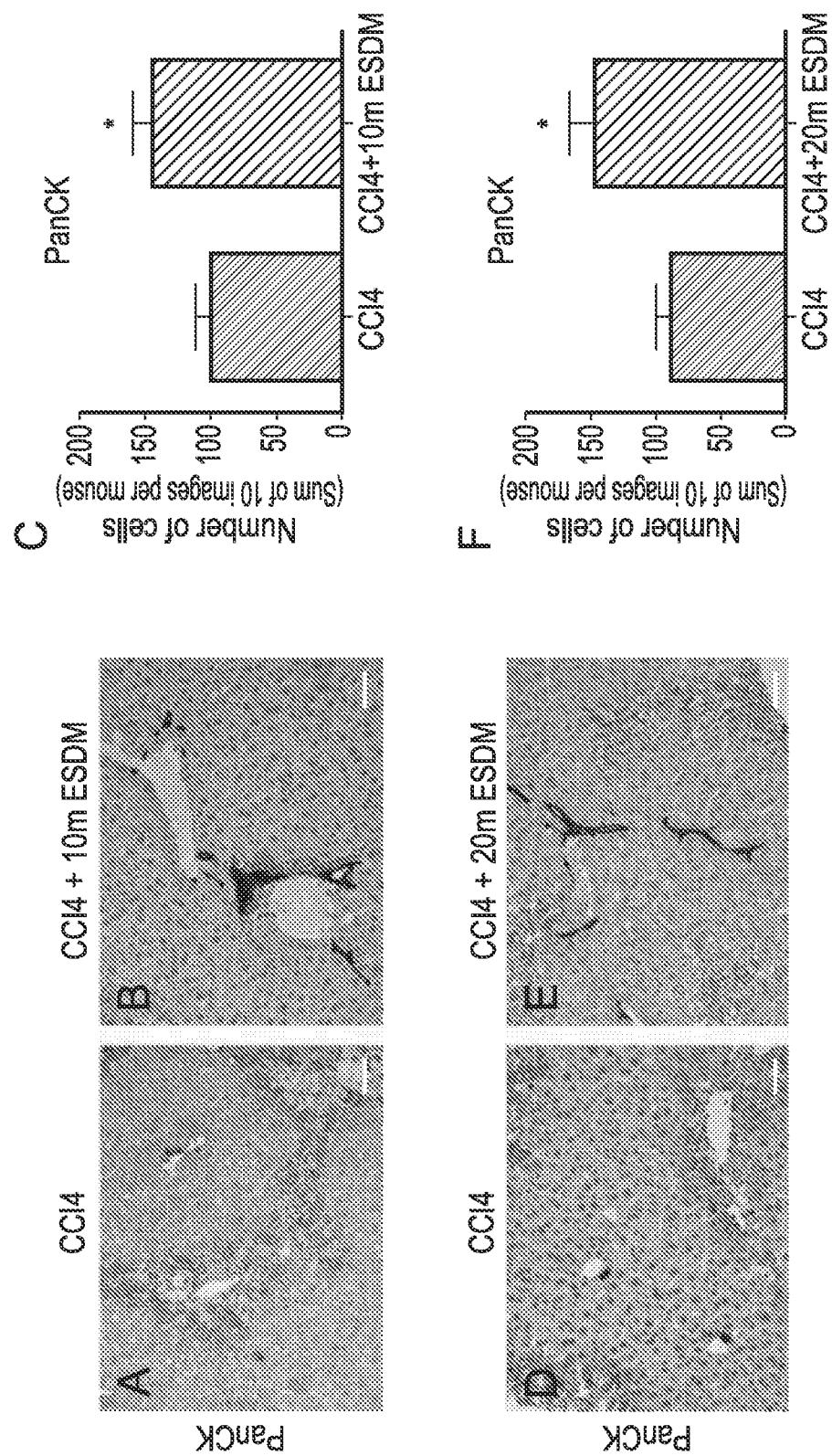
FIG. 19 shows that ESDMs can initiate a progenitor response in injured livers. A significantly higher number of PanCK-positive cells were observed in mice injected with ESDMs compared to control injury livers (A-F). Scale bars 100 μM. [*p<0.05, n=5 per group, Unpaired t-test].

BMDM therapy had previously been shown to ameliorate fibrosis so we assessed whether ESDMs also had an effect on hepatic fibrosis using Picro Sirius Red (PSR) stain for hepatic collagens. When the lower number ($10 \times 10^6$) of ESDM was used there was no significant effect on the level of fibrosis (FIG. 18B-D) whereas when twice as many ESDMs were injected, a significant reduction in PSR staining was observed (FIG. 18E-G). A decline in the number of myofibroblasts is a key event during fibrosis resolution and we also noted a significantly lower number of αSMA positive myofibroblasts in mice treated with the higher dose of ESDMs (FIG. 18 K-M). Healthy, uninjured livers was also stained and analysed.

We observed a significantly higher number of hepatic ductular cells, marked by PanCK staining, in $CCl_4$-injured livers that had been injected with ESDMs compared to control injured livers (FIG. 19A-F). The higher number of PanCK-positive cells was evident in animals receiving both doses of ESDMs replicating an effect previously observed with BMDMs (Bird, T. G. et al. Bone marrow injection stimulates hepatic ductular reactions in the absence of injury via macrophage-mediated TWEAK signaling. *Proc Natl Acad Sci USA* 110, 6542-6547, doi:10.1073/pnas.1302168110 (2013)).

In conclusion this study demonstrates that ESDMs can be produced on a large scale and they have the potential to modulate the effect of liver injury by reducing the density of myofibroblasts and resultant collagen deposition. The cell number of ESDM used in these experiments was 10 fold higher than that used for BMDMs in previous studies.

Do ESDMs Have a Phenotype Comparable to Tissue Resident Macrophages?

Haematopoietic cells derived from ESCs in vitro are thought to be more related to the blood cells associated with the primitive wave of haematopoiesis in the yolk sac during development (Zambidis, E T, Peault, B, Park, T S, Bunz, F & Civin, C I 2005, 'Hematopoietic differentiation of human embryonic stem cells progresses through sequential hematoendothelial, primitive, and definitive stages resembling human yolk sac development' Blood, vol 106, no. 3, pp. 860-870. DOI: 10 1182/blood-2004-11-4522). Tissue resident macrophages are known to be derived from the primitive wave of haematopoiesis, well before the appearance of haematopoietic stem cells (HSC) in the embryo and develop in the absence of Myb, an important HSC transcription factor (Schulz, C. et al. A lineage of myeloid cells independent of Myb and hematopoietic stem cells. Science 336, 86-90, doi:10.1126/science.1219179 (2012)). We considered that the subtle differences that we observed between murine ESDM and BMDMs could be related to their source rather than their culture conditions. We confirmed this by demonstrating that Myb and Ccr2 are expressed at a lower level in ESDMs compared to BMDMs, whereas Pu. 1was higher (FIG. 20A-C). Thus if ESDMs are more like tissue resident macrophages than circulating monocyte-derived cells, we hypothesised that they would be more efficient at repopulating the Kupffer cell compartment of the liver following ablation of endogenous resident macrophages with liposomal clodronate.

We first confirmed that liposomal clodronate treatment did indeed ablate the resident macrophage population and analysed the tissue at different time-points to determine the optimal time for the addition of exogenous macrophages. No $F4/80^+$ macrophages were observed in liver sections 48 hours after liposomal clodronate treatment indicating that complete depletion had occurred by this time point. A few $F4/80^+$ macrophages were evident 72 hours after treatment when endogenous circulating macrophages begin to repopulate the tissue (FIG. 20P).

ESDM and BMDM were labelled with CFSE cell tracking dye (Molecular probes, Life Technologies) and $5 \times 10^6$ cells were injected intravenously 48 hours after liposomal clodronate treatment (FIG. 20D). Liver, lung, kidney and heart tissue was harvested 24 hours later and immunostaining using an anti-FITC antibody (which detects all derivatives of fluorescein including CFSE) was used to detect the injected CFSE-stained cells (FIG. 20E-H, R). $CFSE^+$ cells were detected in liver sections derived from liposomal clodronate treated mice that received either BMDM or ESDM. Quantification of images demonstrated that there were significantly more $CSFE^+$ cells in the livers of mice that were injected with ESDMs compared to BMDMs (FIG. 20M). This result was confirmed by quantification of a DAB-based detection method to identify $CSFE^+$ cells (FIG. 20I-L, N). Some BMDMs and ESDMs were also detected in lung tissue but very few cells engrafted in the kidney and heart of clodronate treated animal. (FIG. 20R).

These data indicate that ESDMs have a higher capacity to repopulate the Kupffer cell compartment than BMDMs.

Figure 20:
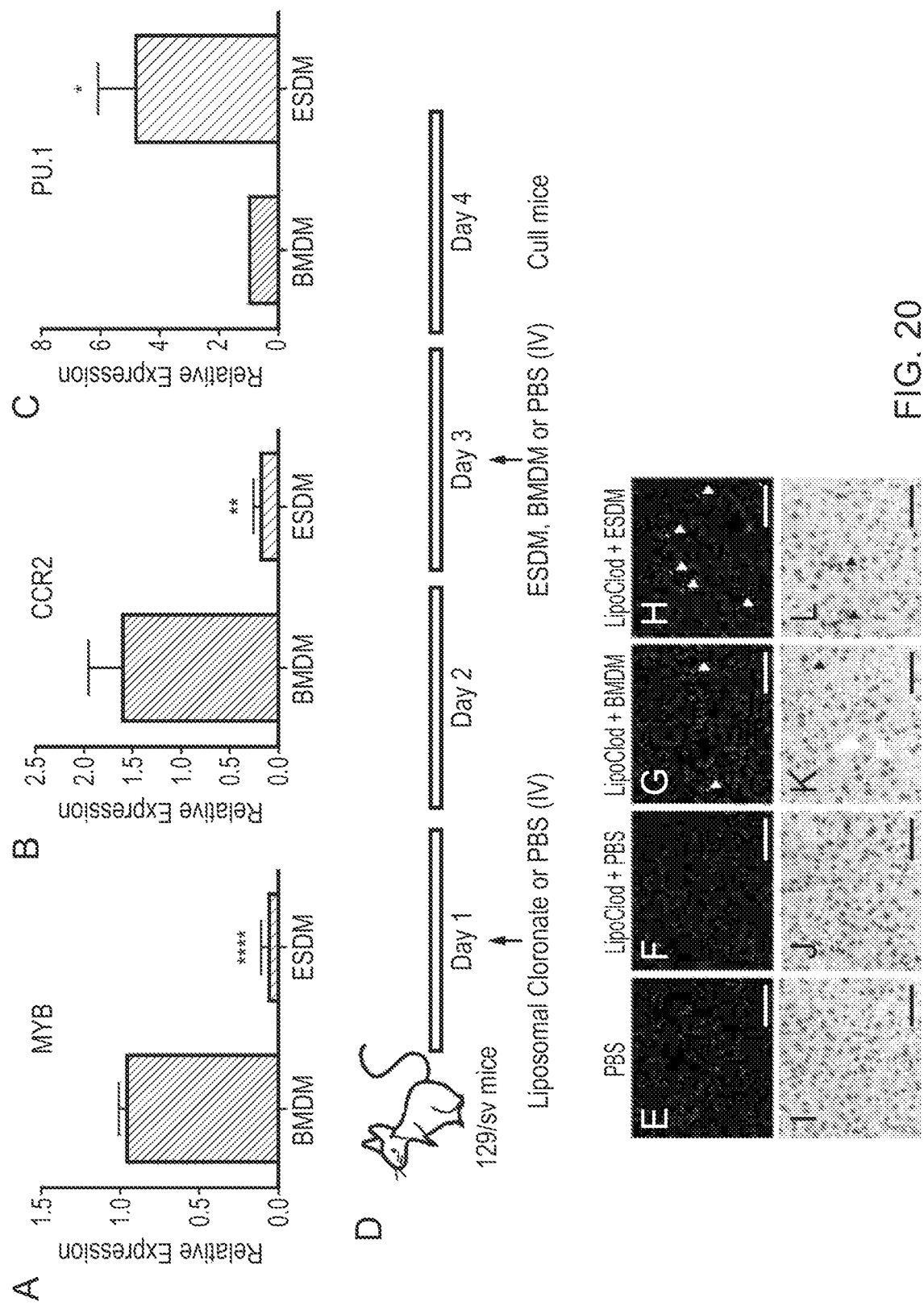
FIG. 20 shows that ESDMs can repopulate the liver of liposomal chlodronate-treated mice. Expression of markers differentially expressed in monocyte-derived versus tissue-resident macrophages, Myb (A), Ccr2 (B), and Pu.1 (C). Schematic representation (D) of liposomal clodronate-induced Kupffer cell depletion and injection of ESDM or BMDM. CFSE immunostaining (E-H; Scale bars 100 μM) and CFSE immunohistochemistry (I-L, Scale bars 50 μM.) of liver sections from the different treatment groups. Quantification of CFSE+ immunostaining (M) and CFSE+ immunohistochemistry (N). Arrowheads point at CFSE+ cells detected. Blood serum analysis of (O) Alkaline phosphatase (ALP), and (P) Albumin levels. (Q) Macrophage populations in livers assessment after liposomal clodronate treatment by F4/80 immunohistochemistry. Representative images of F4/80 stained liver sections of PBS controls (A), 24 hours (B), 48 hours (C), and 72 hours (D) after clodronate treatment. Quantitative analysis of F4/80+ staining (S). (R) Assessment of ESDM and BMDM engraftment in different organs by FITC immunohistochemistry. Representative images of exogenous macrophages in liver, lung, kidney and heart sections of mice treated with PBS (A-D), liposomal clodronate (E-H), liposomal clodronate and BMDM (I-L), and liposomal clodronate and ESDM (M-P), respectively (Scalebars 100 μM). [*p<0.05,p<0.01, *p<0.001, ****p<0.0001; n=5 per group, One-way ANOVA]
Figure 20:
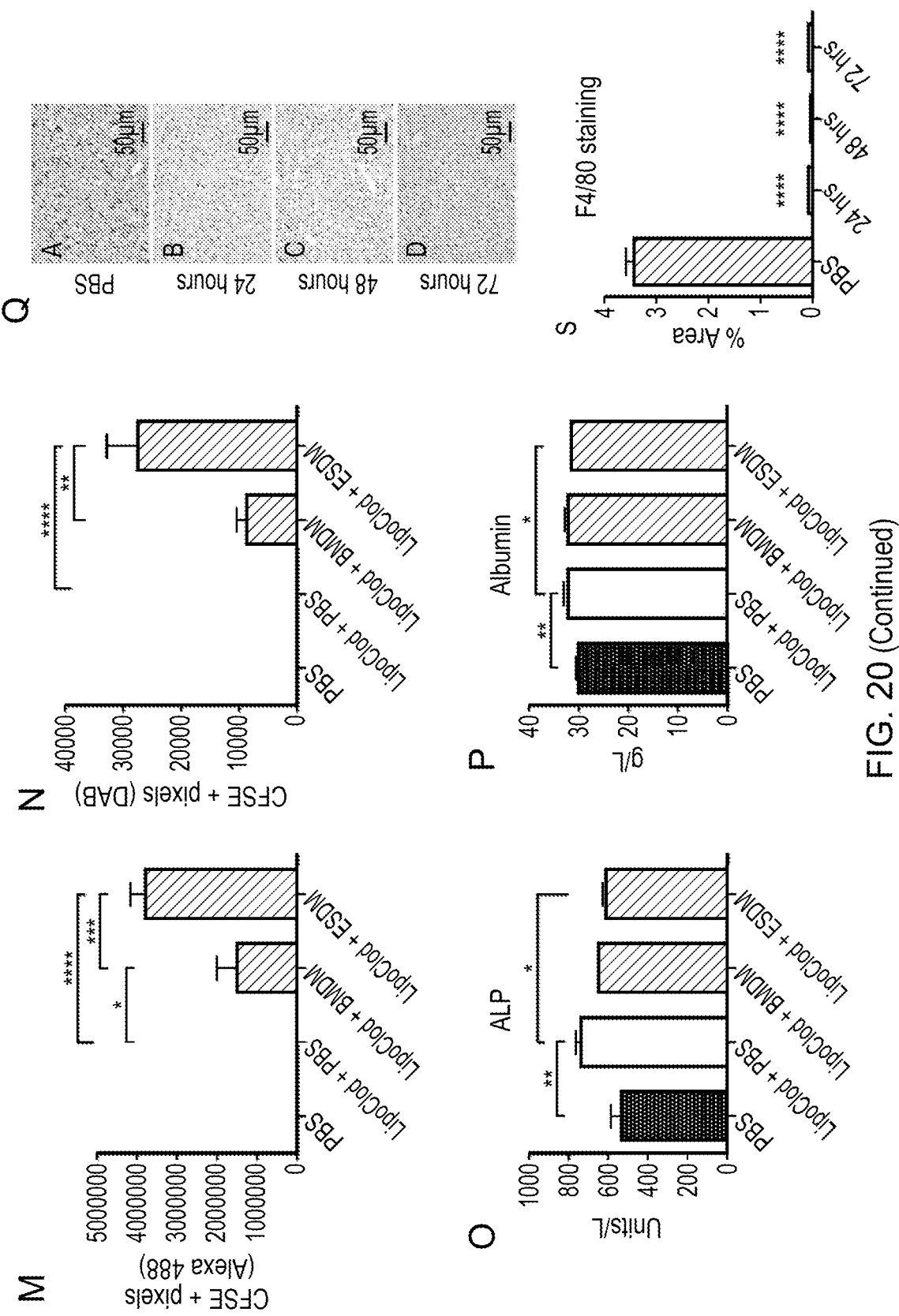
Figure 20:
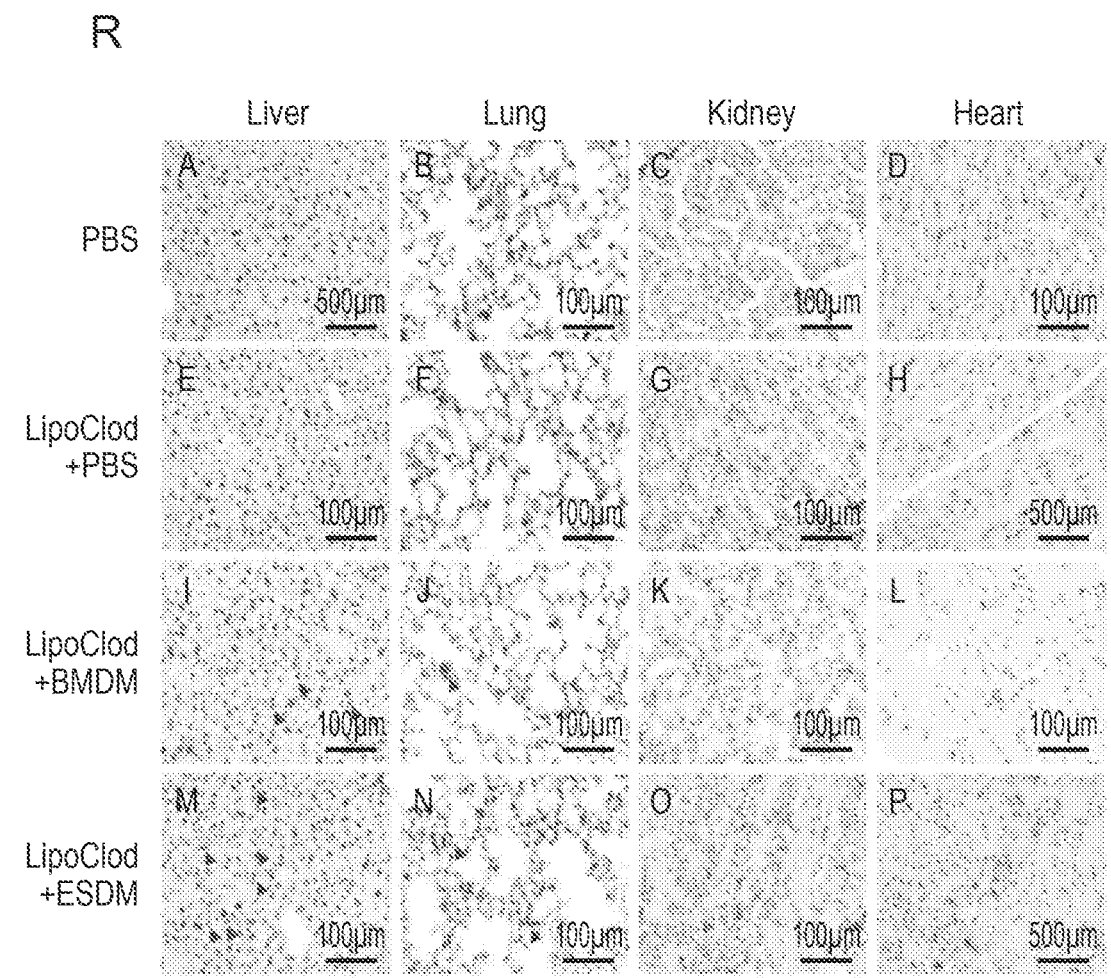

Serum analysis was carried out to assess the effects of the treatments carried out on liver function of the mice (FIG. 20 O, P). Alkaline phosphatase (ALP) levels were significantly elevated in liposomal clodronate treated mice compared to PBS control mice indicating liver damage. ALP levels were significantly lowered in mice that received ESDM, compared to controls indicating that ESDMs had some reparative effect. Serum albumin levels of ESDM recipient mice were also comparable to healthy controls.

Figure 21:
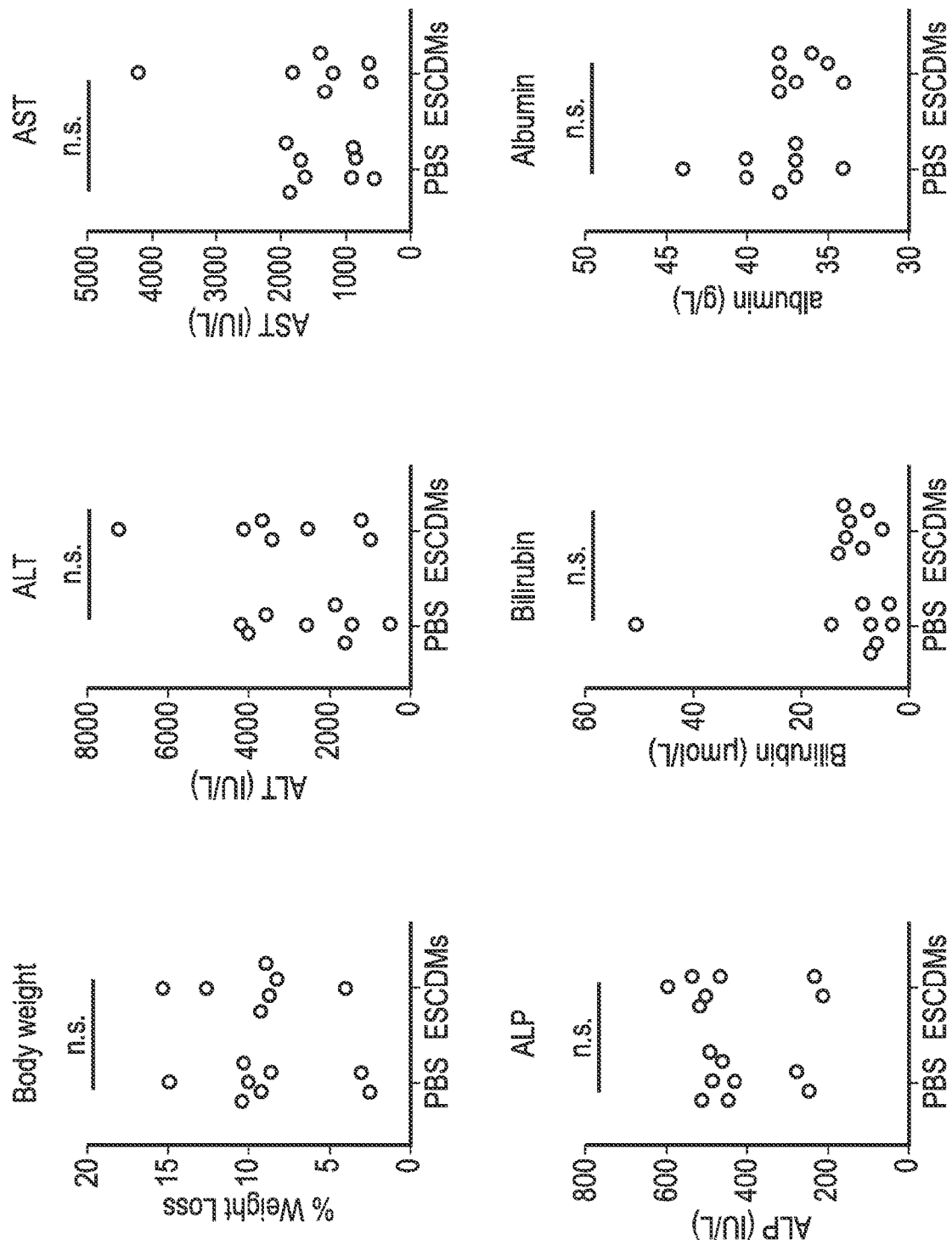
FIG. 21 shows Serum transaminases are not different in ESDM-treated mice 20 hours after injection versus vehicle control.
Figures 22, 23:
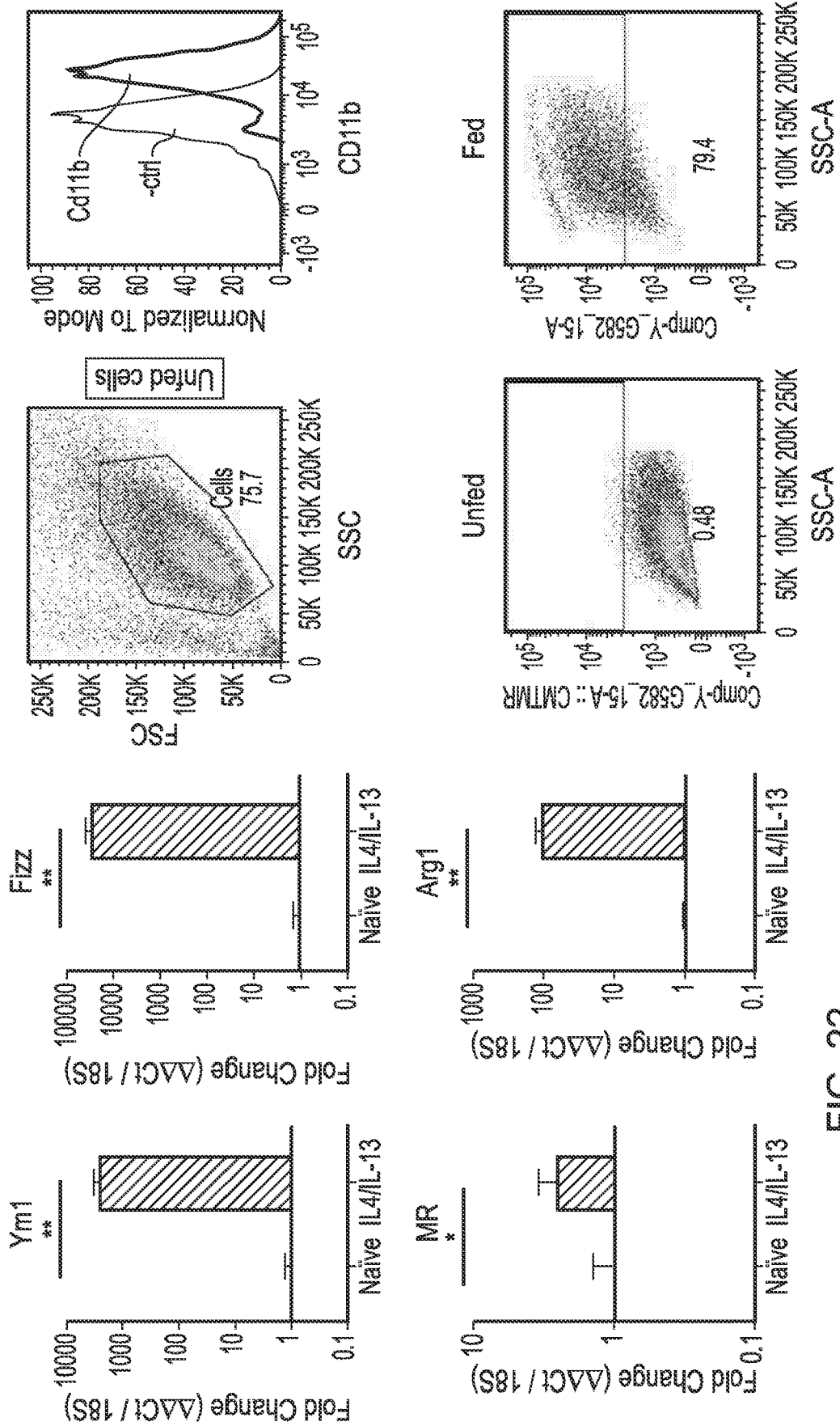
FIG. 22 shows ESDMs show a marked increase in M2-associated genes after 24-hour polarisation in vitro with recombinant murine IL-4/IL-13.
FIG. 23 shows alternatively-activated ESDMs are proficient at phagocytosis in vitro. ESDMs incubated with apoptotic thymocytes in vitro show 79% positivity for phagocytosis versus unfed equivalent cells.
Figure 24:
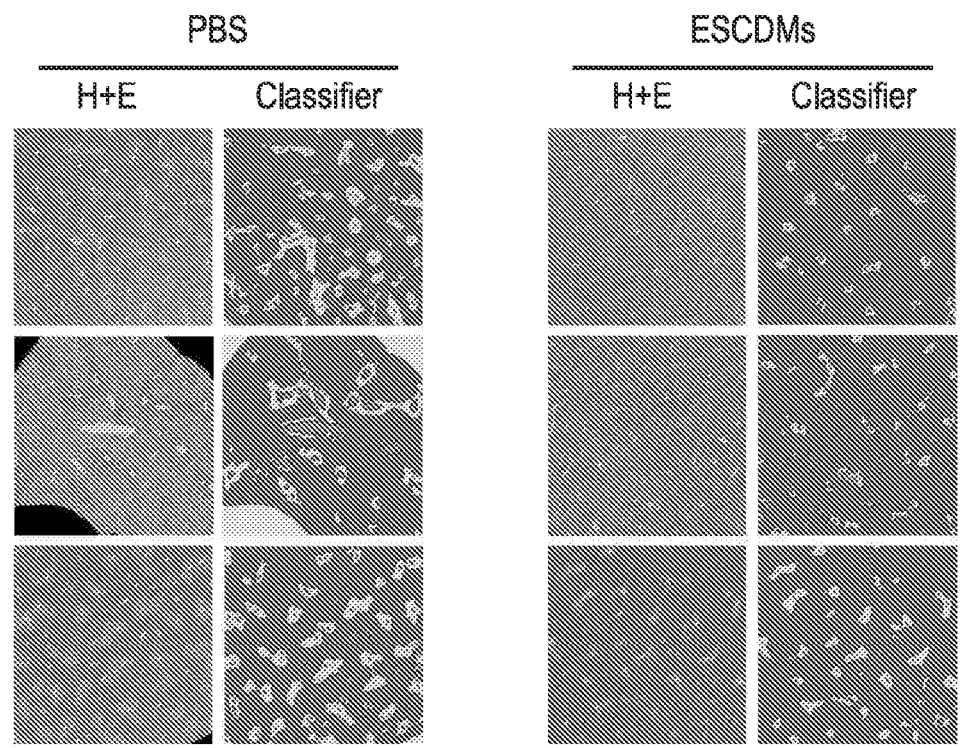
FIG. 24 shows ESDM-treated mice show a reduced area of centrilobular necrosis 20 hours after ESDM-injection (5×106, i.v). Panels show Haemotxylin and Eosin (H+E) stains and their corresponding image segmentation (classifier) used during image quantification.
Figure 24:
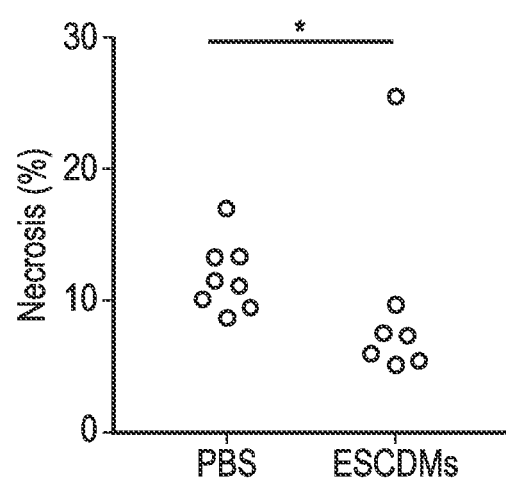

We then tested if macrophages derived from cultured embryonic stem cells can recapitulate the therapeutic efficacy of primary macrophage to ameliorate acetaminophen-induced liver injury. We tested the therapeutic performance of murine ESDMs in the acetaminophen-induced liver injury model via a single i.v. injection ($5 \times 10^6$ cells) at 16 hours. Whilst we observed no significant differences in serum chemistry markers (FIG. 21), we did observe a significant reduction in necrotic area as assessed by H+E staining (FIG. 24). Similar to BMDMs, ESDMs exhibited a highly dynamic switch in gene expression for markers of alternative activation (Ym-1, Fizz, MR, Arg-1) after overnight polarisation with IL-4/IL-13 confirming these signaling pathways are intact in these cells (FIG. 22). Furthermore, polarised ESDMs were shown to be capable of phagocytic ingestion of apoptotic material, a proposed therapeutic mechanism of these cells in the liver injury model: we demonstrate that polarised ESDMs can readily phagocytose fluorescently-labelled apoptotic thymocytes in vitro (FIG.

Figure 25:
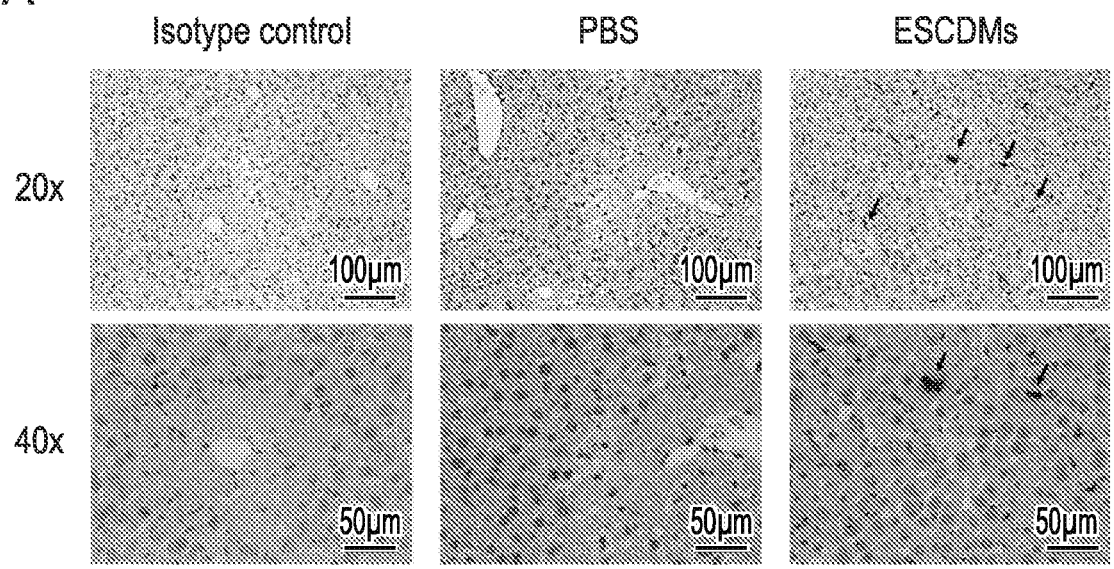
FIG. 25 shows transplanted ESDMs (black arrows) localise to the liver and spleen. Panel A—liver (top row, ×20 magnification; bottom row, ×40 magnification) sections. Panel B—spleen sections.
Figure 25:
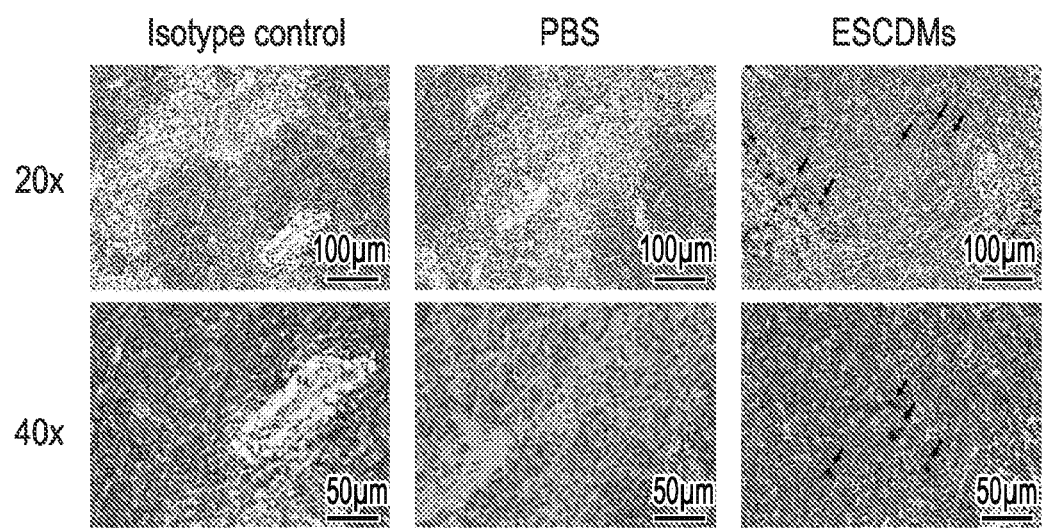

23). Finally, we show via cell tracking that ESDMs populate the liver and spleen soon after i.v. injection (FIG. 25) analogous to BMDMs. Results indicate that ESDMs have therapeutic capacity analogous to primary BMDMs in a model of acute liver injury.

Discussion

We developed a live imaging assay to evaluate macrophage phagocytic ability. This allowed us to monitor not only the number of particles engulfed at the end, but also the rate at which macrophages phagocytosed the particles. We found that unstimulated ESDM did not phagocytose as fast or as many bioparticles as BMDM. Furthermore, ESDM and BMDM primed towards the M2-like phenotype phagocytosed more bioparticles than their M1-primed equivalents ESDM Aids Fibrosis Regression in a Murine Model of Liver Fibrosis When $20 \times 10^6$ ESDM were transplanted, the amount of liver fibrosis was significantly reduced and the number of αSMA+ myofibroblasts was reduced to 50% of control after ESDM delivery. No significant changes were observed in fibrosis or myofibroblast numbers when $10 \times 10^6$ ESDM were transplanted indicating that this anti-fibrotic effect was dose dependent. Interestingly, like BMDMs, both high and low doses of ESDMs stimulated a ductular response as demonstrated by a significant increase in PanCK+ progenitors. These data demonstrate that ESDM therapy can aid in regeneration of damaged liver tissue by inducing the proliferation of PanCK+ ductular cells, and at high dose, ameliorate fibrosis. To our knowledge, this is the first study that demonstrates a therapeutic effect of ESDMs in a model of liver injury.

ESDM are More Efficient at Repopulating a Kupffer Cell-Depleted Liver than BMDM

We found that ESDMs expressed lower levels of Myb and Ccr2 and higher expression of Pu.1 than BMDMs, indicating a tissue-resident macrophage profile. Therefore we assessed the repopulation capacities of ESDM and BMDM in vivo in Kupffer cell depleted livers to test if ESDM would be more efficient than BMDM in this experiment. Significantly higher numbers of CFSE+transplanted cells were detected in ESDM recipients compared to BMDM recipients. These results indicated that ESDM were more efficient than BMDM at reversing the effects of liposomal clodronate treatment in mice by partially repopulating the Kupffer cell compartment. This could either be due to the fact that the phenotype of ESDMs is more comparable to a tissue resident macrophage than BMDMs or that they have an enhanced ability to migrate to the macrophage-depleted tissue.

Materials and Methods

Mouse ESC maintenance and differentiation: The mouse embryonic stem cell (ESC) line E14IV was maintained in Glasgow Minimum Essential Medium (Gibco) supplemented with 10% fetal calf serum (FCS) (Lonza), 2 mM Sodium pyruvate (Gibco), 4 mM L-glutamine (Gibco), 1% Non-essential amino acids (Gibco) and 0.1 mM β-mercaptoethanol (Sigma) and 100 U/ml of Leukaemia Inhibitory Factor (LIF) as previously described (Jackson, M., Taylor, A. H., Jones, E. A. & Forrester, L. M. The culture of mouse embryonic stem cells and formation of embryoid bodies. Methods Mol Biol 633, 1-18, doi:10.1007/978-1-59745-019-5_1 (2010)). The same medium (without LIF) supplemented with 15% L929-conditioned media and 1 ng/ml recombinant IL-3 (Stem Cell Technologies)(herein referred to as Differentiation medium) was used for the production of macrophage as described previously (Zhang et al). Briefly, $6 \times 10^5$ ESCs were cultured in suspension in Differentiation medium to form embryoid bodies (EB). On day 8, EBs were plated onto gelatinised tissue-culture dishes then non-adherent cells were harvested from these cultures on alternate days (day 10 to 20) then plated onto non-treated bacteriological Petri dishes in Differentiation medium without IL-3. These monocyte-like cells adhered to the plastic petri-dishes forming a monolayer and matured into embryonic stem cell derived macrophages (ESDM).

Bone marrow derived macrophages: Bone marrow was flushed from murine femurs and tibia, cultured in Ultra-low attachment 25 $cm^2$ flasks (Corning) in Dulbecco's Modified Eagle Medium (DMEM) (Sigma) with 10% FCS, 15% L929-conditioned media and 1% Pen/Strep for 7 days (with a media change on day 4) then bone marrow-derived macrophages (BMDM) were harvested by collecting all adherent and non-adherent cells.

Cytospin and Rapid Romanowsky Staining: Cytospins of macrophages were prepared by harvesting, counting and re-suspending $1 \times 10^5$ macrophages in 200 μL PBS. They were cytocentrifuged at 300 g for 3 minutes in a Thermo Shandon Cytospin 4 and allowed to air dry. The Rapid Romanowsky Stain Pack (TCS Biosciences) was used to fix and stain the cells as per manufacturer's instructions. The slides were rinsed briefly in water, air-dried and mounted with Mowiol (Sigma).

Macrophage polarisation: Adherent ESDM and BMDM were primed in vitro to adopt a M1- or M2-like phenotype by treating with LPS (0.1 μg/ml)(Sigma L4391-1 mg) and IFNγ (10 U/ml) or IL-4 (20 ng/ml) respectively for 48 hours. The Griess Reagent System (Promega) was used to measure $NO^-$ levels in culture supernatants according to the manufacturer's instructions.

Flow cytometry: Cells were harvested, counted and $1 \times 10^6$ cells were resuspended in 100 μL PBS containing 1% Bovine Serum Albumin (BSA). Pre-conjugated antibodies were added at their optimal concentrations and incubated on ice for 20 minutes. Cells were subsequently washed in 2 mL PBS (containing 1% BSA) and centrifuged at 400 g for 5 minutes. Cell pellets were resuspended in 200 μL PBS with 1% BSA. In most experiments cells were stained with a Live/Dead cell viability stain such as DAPI or 7-AAD. The following anti-mouse antibodies were used: anti-F4/80 APC (BioLegend), anti-CD11b Alexafluor 488 (BioLegend). The following anti-human antibodies were used: anti-CD93 PE (eBioscience), anti-25F9 APC (eBioscience), anti-CD11b Alexafluor 488 (BioLegend).

Quantitative Real-Time PCR (qRT-PCR): qRT-PCR was performed using the ABI 7500 Fast Real-Time PCR System (Applied Biosystems) and analysed with SDS software Version 1.4 (Applied Biosystems). The Taqman Fast Universal PCR Master Mix (2×) (Applied Biosystems) was used with UPL assays that were designed on the Universal ProbeLibrarySystem Assay Design Center (Roche)(Table 1). The ΔΔCt method was used with GAPDH to normalize cDNA levels and the "control" sample of each experiment was used as a calibrator to calculate relative change in gene expression. All data is presented as fold-change over the expression level of the calibrator.

TABLE 1

Primer sequences

A Primers for qRT-PCR analysis of mouse macrophage gene expression analysis

| Gene | Forward primer (5'-3') | Reverse primer (5'-3') |
|---|---|---|
| iNOS | AACACCCGGGACATGAGAC | CCTGGGAGGATCAGGAAGTC |
| CD86 | GAAGCCGAATCAGCCTAGC | CAGCGTTACTATCCCGCTCT |
| ARG1 | GAATCTGCATGGGCAACC | GAATCCTGGTACATCTGGGAAC |
| FIZZ1 | TATGAACAGATGGGCCTCCT | AGGCAGTTGCAAGTATCTCCA |
| TWEAK | CAGGATGGAGCACAAGCAG | GGCTGGAGCTGTTGATTTTG |
| MMP9 | ACGACATAGACGGCATCCA | GCTGTGGTTCAGTTGTGGTG |
| MMP12 | GCTGCTCCCATGAATGACA | AAGCATTGCACACGGTTGTA |
| MMP13 | GCCAGAACTTCCCAACCAT | TCAGAGCCCAGAATTTTCTCC |

B Primers for qRT-PCR analysis of human macrophage gene expression analysis

| Gene | Forward primer (5'-3') | Reverse primer (5'-3') |
|---|---|---|
| CD40 | GCCAAGAAGCCAACCAATAA | TGGCATCCATGTAAAGTCTCC |
| CD80 | AAGCAAGGGGCTGAAAAGAT | AAGGGCAAGGTGGGGTAAT |
| TGM2 | TCACCTTCAGTGTCGTGACC | CAGCATCTCTTAGTGGAAAACG |
| MRC1 | TGTTTTGGTTGGGATTGACA | TCTCCATAAGCCCAGTTTTCA |

Phagocytosis assay by Live Imaging: $1 \times 10^5$ macrophages were plated in tissue-culture grade 96-well plates (CellCarrier, PerkinElmer) three days prior to imaging. Cells were washed with PBS, 100 µl NucBlue Live ReadyProbes Reagent (Molecular Probes) (two drops per 1 ml PBS) was added to each well and incubated at 37° C. for 20 minutes. Cells were washed with PBS and treated with 100 µl/well of CellMask™ Deep Red Plasma membrane Stain (Molecular Probes) as per the manufacturer's instructions and incubated for a further 30 minutes. CellMask™ reagent was aspirated and 100 µL PBS was added to each well. One vial of pHrodo™ Green Zymosan A BioParticles Conjugate (Molecular Probes) was resuspended in 2 ml PBS at 0.5 mg/mL, thoroughly vortexed and briefly sonicated then further diluted 1:5 in PBS. 100 µL of pHrodo™ BioParticles were added to each immediately prior to imaging. Imaging was performed on the Operetta High-Content Imaging System (Perkin Elmer) at 5 minute intervals, at 40× magnification, and images were analyzed on the Harmony High-Content Imaging and Analysis Software (Perkin Elmer). Each experiment was carried out three times, and included 3 technical replicates.

Liver fibrosis model: Liver injury was induced in 8-10 weeks old 129/SV mice (Harlan Laboratories) by intraperitoneal injection of 2 µL/g $CCl_4$ (1:3 CCL4:olive oil) twice a week over a 4-week period. Mice were randomly selected to receive intravenous injections of ESDMs or control saline (n=5 per group) at the start of week two and mice were culled 21 days later. Livers were perfused with saline, removed and fixed in formalin and processed for immunohistochemistry.

Liposomal clodronate-mediated Kupffer cell depletion: Liposomal clodronate (5 mg/mL) was purchased from clodronateliposomes.org. The clodronate suspension was brought to 37° C. and mixed thoroughly prior to injecting. 200 µL of liposomal clodronate or control PBS (n=5 per group) was injected into the tail vein.

Immunohistochemistry: Tissues were embedded in paraffin and 4 µm slices were cut and mounted on glass slides and immunohistochemistry was carried out for detection of αSMA, PanCK, CFSE and F4/80 as described (Thomas, J. A. et al. Macrophage therapy for murine liver fibrosis recruits host effector cells improving fibrosis, regeneration, and function. Hepatology 53, 2003-2015, doi:10.1002/hep.24315 (2011); Russo, F. P. et al. The bone marrow functionally contributes to liver fibrosis. Gastroenterology 130, 1807-1821, doi:10.1053/j.gastro.2006.01.036 (2006)) (Table 2). For PSR staining, sections were dewaxed and rehydrated. Sections were treated in haematoxylin for 8 minutes followed by Picro Sirius Red for an hour. Slides were subsequently washed in acidified water, dehydrated and mounted.

TABLE 2

List of Antibodies

| Antibody | Fluorochrome | Dilution | Supplier |
|---|---|---|---|
| A Anti-mouse antibodies for flow cytometry | | | |
| F4/80 | APC | 1/100 | BioLegend |
| CD11b | Alexafluor488 | 1/100 | BioLegend |
| SSEA1 | APC | 1/100 | RnDSystems |
| CSF1R | PE | 1/100 | BioLegend |
| B Anti-human antibodies for flow cytometry | | | |
| CD43 | PE | 1/100 | eBioscience |
| CD45 | APC | 5/100 | eBioscience |
| CD93 | PE | 0.5/100 | eBioscience |
| CD14 | APC | 5/100 | eBioscience |
| 25F9 | APC | 4/100 | eBioscience |

TABLE 2-continued

List of Antibodies

C Antibodies for immunohistochemistry

| Antibody | Description | Dilution | Supplier |
|---|---|---|---|
| aSMA | Mouse anti-mouse | 1/2000 | Ab7817, Abcam |
| PanCK | Rabbit anti-mouse | 1/200 | Z0622, Dako |
| F4/80 | Rat anti-mouse | 1/50 | Ab6640, Abcam |
| FITC | Goat anti-mouse | 1/100 | 71-1900, Invitrogen |

For quantification of PSR and αSMA staining, images at 40× (Nikon Eclipse E600 microscope) were tiled and quantification of positive staining was carried out using the image analysis software, ImageJ. For quantification of PanCK staining, positive cells were counted from 20 non-overlapping fields per sample as described (Thomas J. A. et al. Macrophage therapy for murine liver fibrosis recruits host effector cells improving fibrosis, regeneration, and function. Hepatology 53, 2003-2015, doi:10.1002/hep.24315 (2011)).

Statistical analysis: Statistical analysis was performed using the GraphPad Prism software version 6.0 c. All data are expressed as Mean+Standard Error of the Mean (SEM). p-values less than 0.05 were considered statistically significant (*$p<0.05$, $p<0.01$, *$p<0.001$, ****$p<0.0001$). The following statistical analyses were used: Unpaired Student's t-test and ANOVA.

Murine embryonic stem cell-derived macrophages: A pure population of mESDMS were differentiated from murine E14 mouse embryonic stem cell line (Handyman et al., 1989) essentially as described previously (Zhuang et al. 2012). Briefly, ESCs were cultured with GMEM containing recombinant IL-3 (1 μg/mL) and L929-conditioned medium containing m-CSF (15% v/v) for 8-days to yield non-adherent macrophage progenitor cells. Macrophage progenitors were matured in GMEM containing only L929-conditioned medium containing m-CSF (15% v/v) for 6-10 days after. mESDMs were harvested from ultra-low attachment flasks (Corning), counted and polarised in GMEM containing recombinant murine IL-4 (20 ng/mL), IL-13 (20 ng/mL), and CSF1 (20 ng/mL) for 24 hours. Polarised ESDMs were harvested, counted, and stained with CFSE before injection into mice with acetaminophen (APAP)-induced liver injury ($5 \times 10^6$, i.v.).

APAP-induced liver injury: Prior to APAP administration, mice were fasted for 14 hours. Mice received either a single injection of APAP (350 mg/kg, i.p.) in warm saline or saline alone. CFSE-stained ESDMs were resuspended in Dulbecco's Phosphate-Buffered Saline (DPBS) and administered ($5 \times 10^6$ cells, 100 μL) via tail vein to mice 16 hours after APAP administration. One hour before cull, mice were pulsed with 1 mg (i.p.) of 5-Bromo-2'-deoxyuridine (BrdU, Sigma Aldrich) in PBS to label proliferating cells. Mice were culled and whole blood was collected via cardiac puncture. Serum was collected via centrifugation (14,000 g, 4° C.) after clotting. Liver tissue was harvested and fixed in formalin (20 hours) or frozen on dry ice and stored at −80° C. before analysis.

Necrosis quantification: Four micron sections of liver tissue were cut on a rotary microtome and collected on Surgipath Superior Adhesive Slides (Leica Biosystems) and dried overnight at 45° C. Sections were stained with haematoxylin and eosin on a Shandon Varistain Gemini ES Automated Slide Stainer (ThermoScientific) and mounted using the Shandon ClearVue Coverslipper (ThermoScientific). For necrosis quantification, slides were scanned to create a single image with Dotslide VS-ASW software (Olympus) using a motorised stage and an Olympus BX51 microscope, acquiring images using an Olympus PlanApo 2× lens and Olympus XC10 camera. Images were analyzed using the Trainable WEKA Segmentation plugin in FIJI. A separate classifier identifying necrotic and viable tissue was determined and applied to all tissue in each image.

Gene expression analysis: To confirm appropriate ESDM cytokine-induced polarisation on ultra-low attachment plastics in vitro, ESDM were seeded at $2.5 \times 10^5$ cells/well in 24 well plastic plates or 24-well ultra-low attachment plates. Cells were allowed to adhere overnight in complete media (DMEM:F12 media containing 20 ng/mL CSF1). Media was removed and replaced with DMEM:F12 media with and without appropriate cytokines (n=3; see methods above) for 24 hours to drive polarisation. RNA was harvested from cells using the RNeasy Mini Kit (Qiagen) according to the manufacturer's instructions. RNA was quantified spectrophotometrically using Nanodrop ND-1000 (Thermo Scientific) and reverse transcribed using Quantitect Reverse Transcription kit (Qiagen) including genomic DNA removal step. Gene expression was quantified using QuantiTect SYBR Green PCR Kit (Qiagen) in 384-well format on a Roche Lightcycler 480 II (Roche, Basel, Switzerland). Gene expression was measured using commercially-available Quantitect primers (Qiagen) designed for the following genes, Ym1, Fizz, Mr, Arg1. Relative expression was determined using the 2-ΔΔCT method versus naïve ESDMs using 18S rRNA as the housekeeping gene.

Phagocytosis assays: AAMs were incubated with apoptotic thymocytes (primary thymocytes harvested from 3-5 week old C57BL6 mice, treated with 1 μM hydrocortisone, as previous) (30). Apoptotic thymocytes were labelled using CMTMR (Invitrogen) according to the manufacturer's instructions (31). BMDMs were challenged with labelled apoptotic cells for 30 mins, 1 hour, or 2 hours at a 1:5 ratio at 37° C. or 4° C. Cells were washed and phagocytosis verified by flow cytometry after staining with anti-CD11b BV650 (clone M1/70; Ebioscience) and anti-Ly6C V450 (clone HK1.4; Ebioscience). Percentage of Ly6C+ cells was calculated in the gate of CD11b+ CMTMR+ cells at 37° C. Mean fluorescence intensity (MFI) for CMTMR was calculated on the same gate in the same conditions. Data were acquired on a LSRII Fortessa (BD Biosciences).

Immunohistochemistry for ESDM localisation: Four micron sections of liver and spleen tissue were cut on a rotary microtome, collected on Superfrost Plus adhesive slides (Thermo Fisher) and dried overnight at 45° C. The slides were dewaxed in xylene and rehydrated through alcohols (100%-70%). Antigen retrieval was performed by boiling for 15 min in sodium citrate buffer, pH 6.0. Endogenous peroxidase activity was blocked by incubation with Bloxall (Vector) for 15 min at room temperature. The slides were rinsed in PBS. Endogenous avidin and biotin binding sites were blocked by incubation with avidin block (Invitorgen) and biotin block (Invitrogen), each for 15 min at room temperature. The slides were rinsed in PBS after each step. Non-specific binding was blocked with Protein block (Spring Bioscience) for 1 hour at room temperature. The slides were incubated with primary anti-FITC antibody (Invitrogen, CAT #71-1900) diluted 1 in 200 in antibody diluent (Invitrogen). Isotype control antibody (Vector, I-1000) was diluted in antibody diluent to match the protein concentration of the primary antibody. The slides were incubated overnight at 4° C. The slides were rinsed in PBS. The slides were incubated with secondary biotinylated goat anti-rabbit antibody (Vector, BA-1000) diluted 1:500 in antibody diluent and incubated for 1 hour at room temperature. The slides were rinsed in PBS. The slides were incubated with Vector RTU ABC reagent (Vector) for 30 min at room temperature to allow DAB detection. The slides were rinsed in PBS and then incubated with DAB reagent (Dako) for 5 min at room temperature in the dark. The slides were rinsed in PBS. The slides were counterstained in Harris haematoxylin and then placed briefly in Scott's tap water. The slides were dehydrated through alcohols (70%-100%) and cleaned in xylene. The slides were mounted in Pertex mounting medium and imaged using Nikon Eclipse E600 microscope equipped with QImaging Retiga 2000R camera.

Example 3

Human iPSC Derived Macrophages

Differentiation of Human iPSCs to Macrophages

To extend our work to human studies, we optimised a feeder- and serum-free protocol to generate macrophages from human induced pluripotent stem cells (iPSC) based on work published by van Wilgenburg et al (Efficient, long term production of monocyte-derived macrophages from human pluripotent stem cells under partly-defined and fully-defined conditions. PLoS One 8, e71098, doi:10.1371/journal-.pone.0071098 (2013)). The human induced pluripotent stem cell line, SFCi55 was generated in house and was confirmed to be pluripotent and have a normal karyotype (Yang, C-T., Ma' R., Axton, R., Jackson, M., Taylor, H., Fidanza, A., Marenah' L., Frayne, J., Mountford, J & Forrester, L. M. (2016). *Activation of KLF1 Enhances the Differentiation and Maturation of Red Blood Cells from Human Pluripotent Stem Cells. Stem Cells* 10.1002/stem.2562). They were maintained in StemPro medium prepared by supplementing DMEM/F12 with Glutamax (Invitrogen) with StemPro supplement (Invitrogen), 1.8% BSA (Invitrogen), 0.1 mM β-mercaptoethanol (Invitrogen) and 20 ng/ml human basic FGF (Invitrogen). The method for differentiation of iPSCs to macrophages was adapted from van Wilgenburg et al. On Day 0, spent medium was removed from one confluent well of a 6-well plate, and replaced with 2 ml StemPro (ThermoFisher) supplemented with cytokine Mix 1 (50 ng/ml BMP4, 50 ng/ml VEGF, and 20 ng/ml SCF). Cells were cut using the EZPassage™ tool, and gently dislodged with a Pasteur pipette. They were divided equally into two wells of an Ulta-Low Attachment 6-well plate (Corning), and 2 ml X-VIVO™ 15 media with cytokine Mix 1 was added to each well. Cells were cultured in suspension for 3 days (with a cytokine top up on Day 2), to make embryoid bodies (EBs). On Day 4, EBs were lifted and transferred to gelatin-coated tissue-culture grade 6-well plates in X-VIVO™ 15 media supplemented with cytokine Mix 2 (100 ng/ml M-CSF, 25 ng/ml IL3, 2 mM Glutamax, 1% Penicillin/Streptomycin, 0.055 M β-mercaptoethanol). Approximately 30 EBs were plated in each well. EBs were maintained in this medium for the remaining duration of the protocol, with spent medium being replaced with fresh medium every 3-4 days. After about 2 weeks, the EBs produced macrophage progenitors in the culture supernatant and these were harvested and transferred to 10 cm² bacteriological dishes in X-VIVO™ 15 medium supplemented with cytokine Mix 3 (100 ng/ml M-CSF, 2 mM Glutamax, 1% Penicillin/Streptomycin) and allowed to mature for 5-7 days into iPSC-derived macrophages (iPSC-DM). Macrophage progenitors could be harvested twice a week for approximately 2 months.

Figure 26:
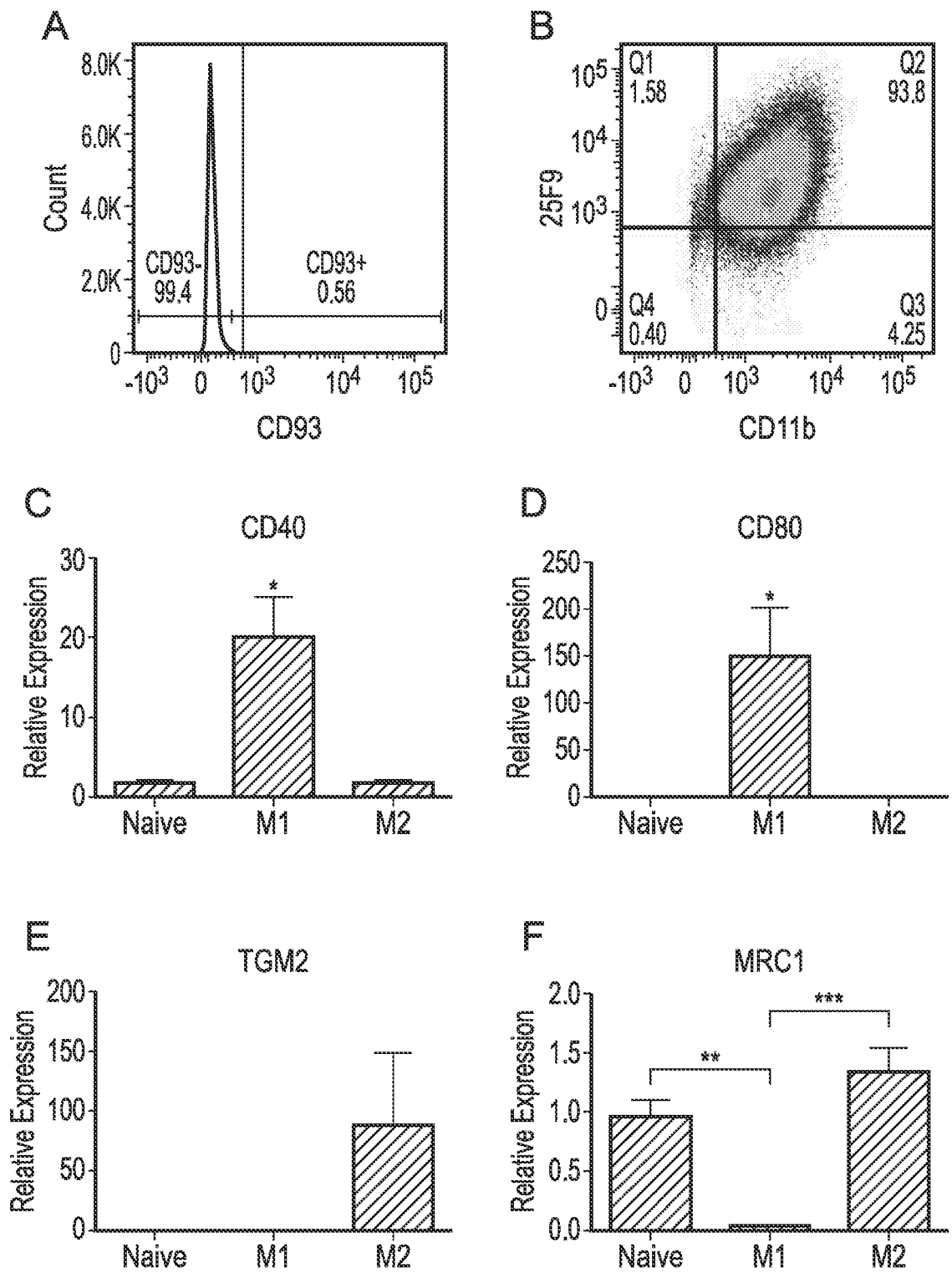
FIG. 26 shows production of macrophages from human pluripotent stem cells Macrophage derived from hPSC express both CD11 b and 25F9 (B) but not CD93 (A) and key M1 (C, D) and M2-associated genes (E, F) are upregulated upon stimulation. Using the live phagocytosis assay iPSC-DM followed the same trend as MDM, where "naïve" and M2 activated macrophages were more phagocytic then M1-activated macrophages (G, H). [$p<0.05$, $p<0.01$, *$p<0.001$; n=3, (C-F) One-way ANOVA, (G-H) Two-way ANOVA with Tukey's multiple comparison test].
Figure 26:
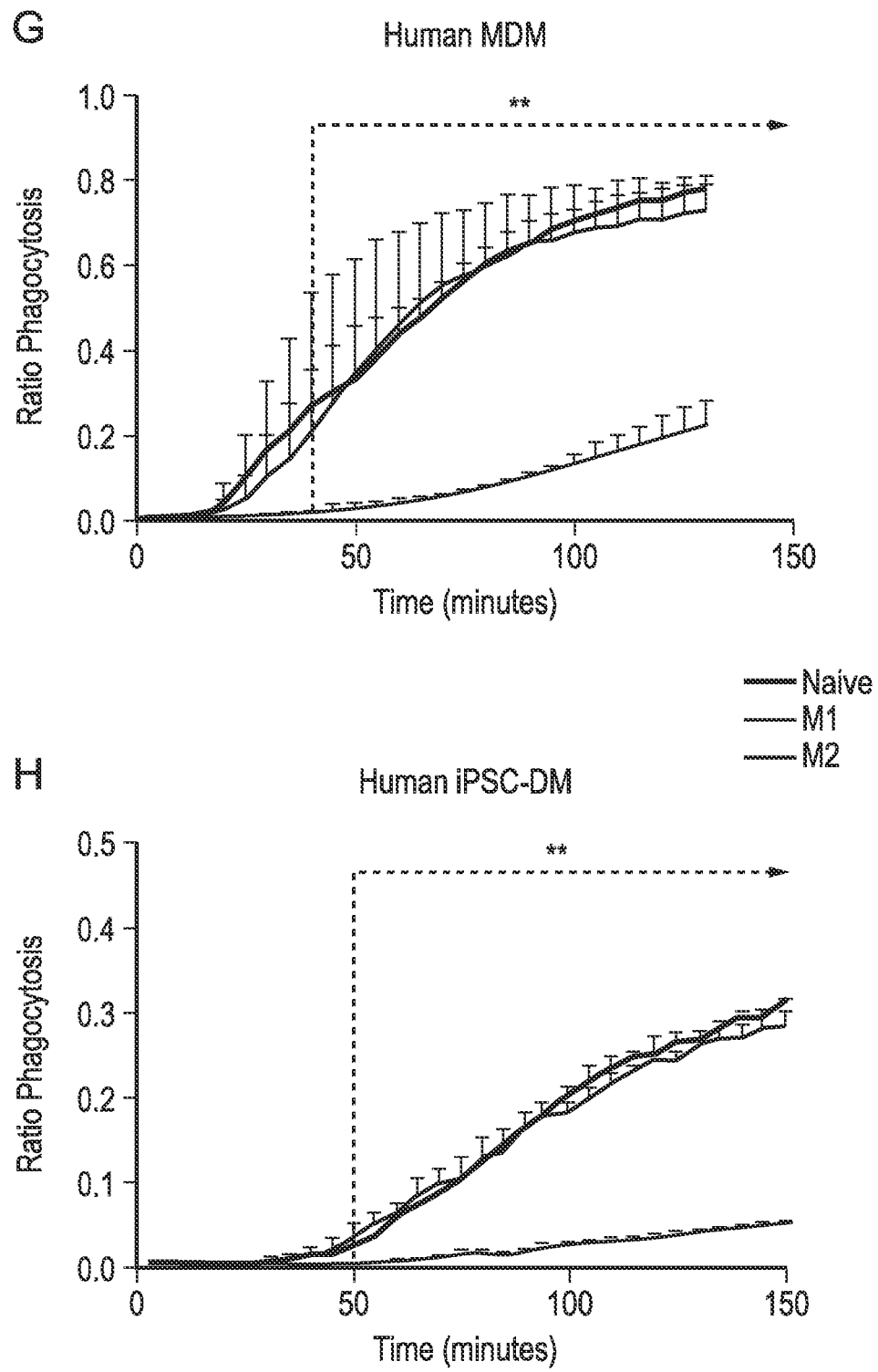
Figure 27:
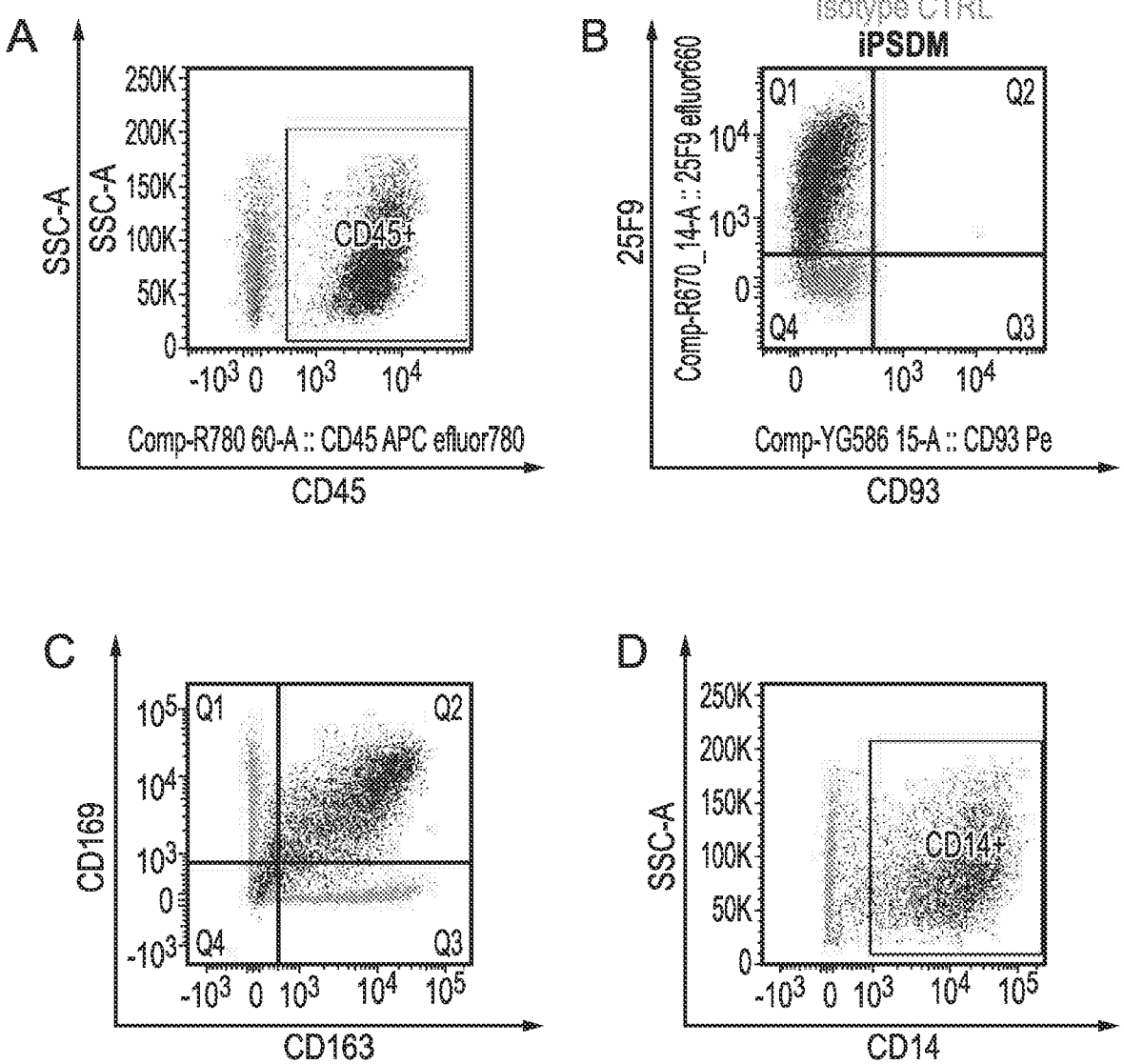
FIG. 27 shows iPSC-derived macrophages express CD45 (A) 25F9 (B), CD169 (C), CD163 (C), CD14 (D) and CD43 (E). There is a low level of VCAM1 (F) and CD15 (G) in a small proportion of iPSCs. iPSCs do not express CD93 (B).
Figure 27:
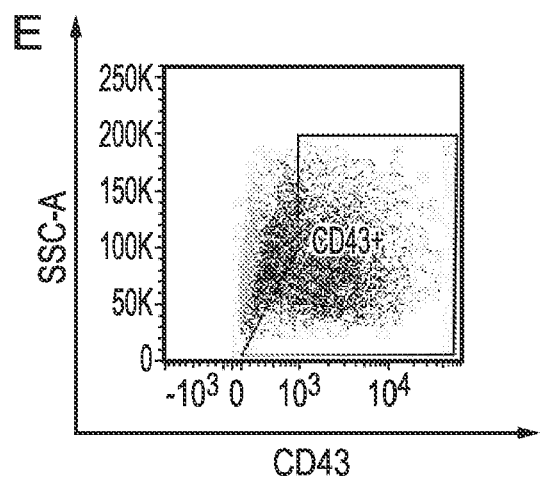
Figure 27:
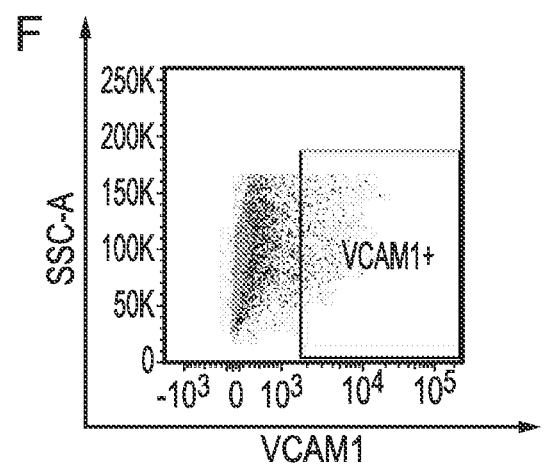
Figure 27:
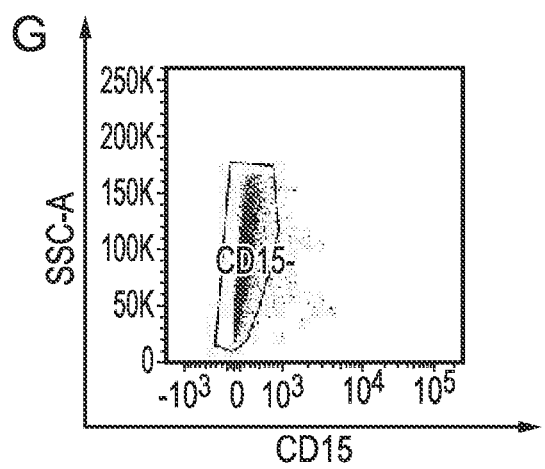
Figure 28:
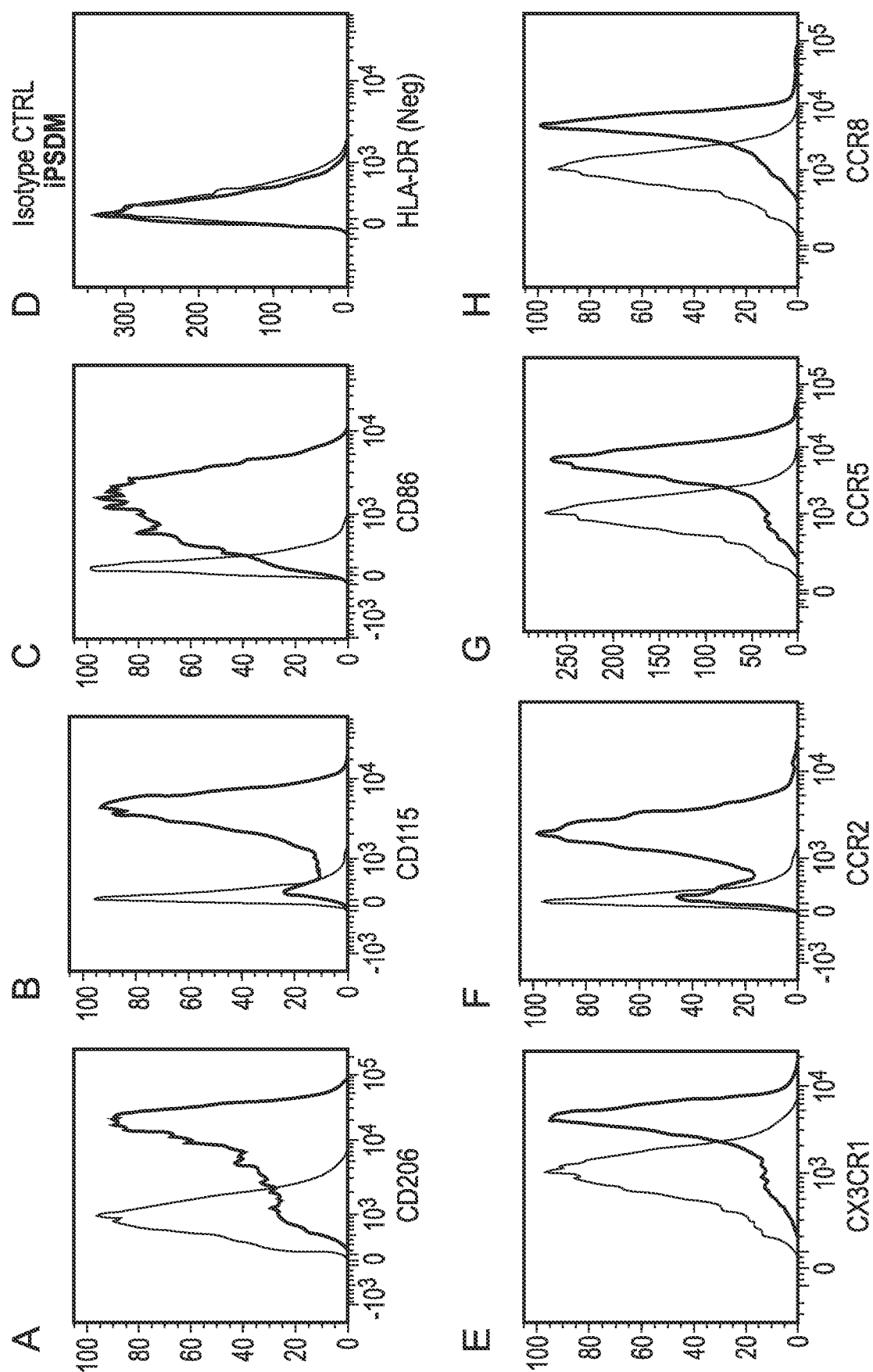
FIG. 28 shows iPSC-derived macrophages express CD206 (A), CD115 (B), CD86 (C), CX3CR1 (E), CCR2 (F), CCR5 (G) and CCR8 (H) but do not express HLA-DR (D).

The human iPSC-derived macrophages (iPSC-DM) that were generated expressed both the mature macrophage-specific cell surface marker 25F9 and CD11b (FIG. 18B) and did not express the monocyte marker CD93 (FIG. 26A). iPSC-derived macrophages also express CD45, CD169, CD163, CD14, CD43, CD206, CD115, CD86, CXCR1, CCR2, CCR5 and CCR8 (FIGS. 27 and 28). There is a low level of VCAM and CD15 in a small proportion of iPSCs (FIG. 27F, G). iPSCDM do not express HLA-DR. (FIG. 28D). Human iPSC-DM responded to stimuli: M1-related genes CD40 and CD80 were upregulated when activated by LPS-IFNγ, whereas M2-related genes TGM2 and MRC1 gene expression were elevated in response to IL4 (FIG. 26C-F).

We compared naïve and polarised human iPSC-DM with human monocyte-derived macrophages (MDM) in our live imaging phagocytosis assay. Human iPSC-DM followed the same trend as human MDM, where "naïve" and IL4 treated macrophages were found to be more phagocytic then LPS-IFNγ treated macrophages (FIG. 26G, H). However, reminiscent of our observations in mouse ESDM, human iPSC-DM phagocytosed less than human MDM in their "naïve" as well as polarised states indicating that they have a less inflammatory phenotype.

When directly compared to mouse BMDM and human MDM respectively, they were found to be less phagocytic and skewed towards an anti-inflammatory phenotype.

Example 3

Determining the Transcriptional Profile of Alternatively-Activated Macrophages Following Injection Into Mice with Paracetamol (APAP)-Induced Acute Liver Injury (APAP-ALI)

Methods:
CFSE-stained AAMs were collected from digested livers of healthy and APAP-poisoned mice as above, except collected directly into lysis buffer (Qiagen) after sorting via FACS (FACS ARIA II, BD Biosciences). Cell yields ranged from $4.3 \times 10^4$-$5.6 \times 10^5$. Lysates were homogenized using QIAshredder (Qiagen) columns following manufacturer's instructions. Total RNA was obtained using RNeasy Micro Kit (Qiagen), before pre-amplification using $RT^2$ PreAMP cDNA Synthesis Kit (Qiagen). Amplified cDNA was assayed using a catalogued $RT^2$ profiler PCR array (077ZG, Qiagen) with a Roche Lightcycler 480 II PCR machine (384-well format, Roche). Data was analyzed using Gene-Globe online portal (Qiagen). All samples passed data quality control criteria. The $C_T$ cut-off was set to 35. Normalization was performed using arithmetic mean of Actb, Gusb, and Hsp90ab1. Volcano plots were generated by plotting fold-change ($2^{[<]BEGINITALm-ACt}$) versus p-value (calculated based on a Student's t-test of n=3 replicates). The treatment and control groups were AAMs from APAP-treated and PBS-treated mice respectively.

Results
The following genes were analysed: C3, C3ar1, C4b, Ccl1, Ccl11, Ccl12, Ccl17, Ccl19, Ccl2, Ccl20, Ccl22, Ccl24, Ccl25, Ccl3, Ccl4, Ccl5, Ccl7, Ccl8, Ccr1, Ccr2, Ccr3, Ccr4, Ccr7, Cd14, Cd40, Cd40Ig, Cebpb, Crp, Csf1, Cxcl1, Cxcl10, Cxcl11, Cxcl2, Cxcl3, Cxcl5, Cxcl9, Cxcr1, Cxcr2, Cxcr4, Fasl, Fos, Ifng, Il10, Il10rb, Il17a, Il18, Il1a, Il1b, Il1r1, Il1rap, Il1rn, Il22, Il23a, Il23r, Il5, Il6, Il6ra, Il7, Il9, Itgb2, Kng1, Lta, Ltb, Ly96, Myd88, Nfkb1, Nos2, Nr3c1, Ptgs2, Ripk2, Sele, Tirap, Tlr1, Tlr2, Tlr3, Tlr4, Tlr5, Tlr6, Tlr7, Tlr9, Tnf, Tnfsf14, Tollip, Actb, B2m, Gapdh, Gusb, Hsp90ab1 and Hsp90ab1.

Figure 29:
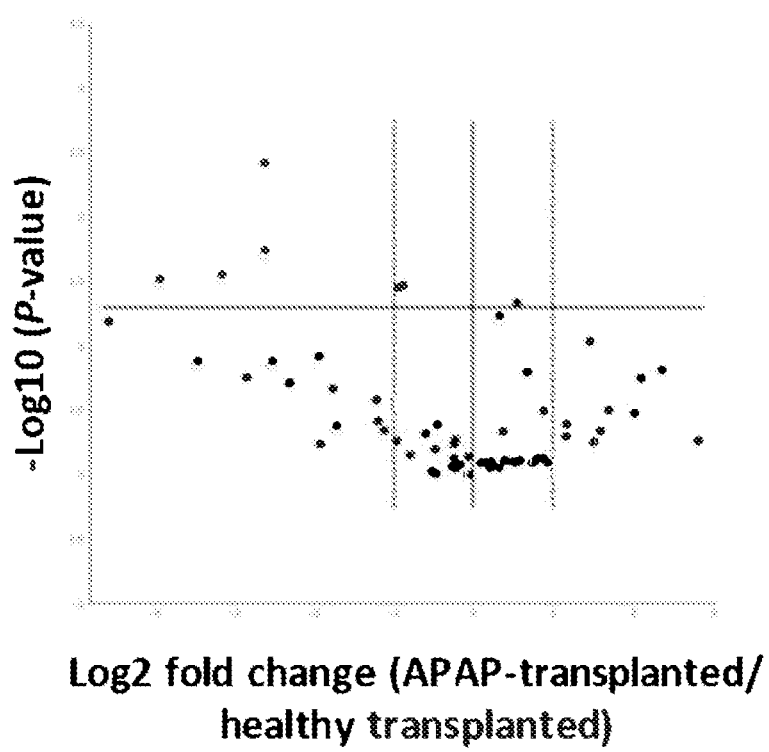
FIG. 29 shows a volcano plot demonstrating low density microarray data (statistical significance versus fold-change on the y- and x-axes, respectively) from FACS-sorted AAMs after transplantation into APAP-poisoned or healthy mice (n=3) in order to determine the degree of transcriptional change 20 hours post-transplantation. Statistically significant genes that are different between APAP and PBS treated mice are above the horizontal line. Student's t-test. AAMs generally retain their anti-inflammatory phenotype with 95% genes analyzed not different between APAP-treated and PBS-treated mice.

As can be seen from FIG. 29, AAMs generally retain their anti-inflammatory phenotype with 95% of genes analysed unaltered between APAP-treated and PBS-treated mice. Thus, the results indicated that AAMs retain their M2 phenotype in a pro-inflammatory environment.

REFERENCES

1. A. M. Larson et al., Acetaminophen-induced acute liver failure: Results of a United States multicenter, prospective study. *Hepatology* 42, 1364 (11 Jan. 2011, 2005).

2. G. Ostapowicz et al., Results of a prospective study of acute liver failure at 17 tertiary care centers in the United States. *Ann Intern Med* 137, 947 (Dec. 17, 2002).

3. W. M. Lee, Acetaminophen and the U.S. acute liver failure study group: Lowering the risks of hepatic failure. *Hepatology* 40, 6 (18 Dec. 2012, 2004).

4. W. M. Lee, Acetaminophen-related acute liver failure in the United States. *Hepatology Research* 38, S3 (27 Sep. 2012, 2008).

5. W. M. Lee, Recent developments in acute liver failure. *Best Pract Res Clin Gastroenterol* 26, 3 (February, 2012).

6. L. F. Prescott, R. N. Illingworth, J. A. J. H. Critchley, Intravenous N-acetylcysteine: The treatment of choice for paracetamol poisoning. *Br.Med.J.* 2, 1097 (20 Dec. 2010, 1979).

7. N. Rolando et al., The systemic inflammatory response syndrome in acute liver failure. *Hepatology* 32, 734 (October, 2000).

8. E. Zigmond et al., Infiltrating monocyte-derived macrophages and resident kupffer cells display different ontogeny and functions in acute liver injury. *J Immunol* 193, 344 (Jul. 1, 2014).

9. B. Gao, W. I. Jeong, Z. Tian, Liver: An organ with predominant innate immunity. *Hepatology* 47, 729 (February, 2008).

10. J. Canalese et al., Reticuloendothelial system and hepatocytic function in fulminant hepatic failure. *Gut* 23, 265 (April, 1982).

11. C. G. Antoniades et al., Reduced monocyte HLA-DR expression: a novel biomarker of disease severity and outcome in acetaminophen-induced acute liver failure. *Hepatology* 44, 34 (July 2006).

12. P. A. Berry et al., Admission levels and early changes in serum interleukin-10 are predictive of poor outcome in acute liver failure and decompensated cirrhosis. *Liver Int* 30, 733 (May, 2010).

13. J. C. Mossanen et al., Chemokine (C-C motif) receptor 2-positive monocytes aggravate the early phase of acetaminophen-induced acute liver injury. *Hepatology*, (Jun. 15, 2016).

14. C. Ju et al., Protective role of kupffer cells in acetaminophen-induced hepatic injury in mice. *Chem.Res.Toxicol.* 15, 1504 (27 Sep. 2012, 2002).

15. P. Ramachandran et al., Differential Ly-6C expression identifies the recruited macrophage phenotype, which orchestrates the regression of murine liver fibrosis. *Proc Natl Acad Sci USA* 109, E3186 (Nov. 13, 2012).

16. Q. You et al., Role of hepatic resident and infiltrating macrophages in liver repair after acute injury. *Biochem Pharmacol* 86, 836 (Sep. 15, 2013).

17. B. M. Stutchfield et al., CSF1 Restores Innate Immunity After Liver Injury in Mice and Serum Levels Indicate Outcomes of Patients With Acute Liver Failure. *Gastroenterology* 149, 1896 (December, 2015).

18. J. A. Thomas et al., Macrophage therapy for murine liver fibrosis recruits host effector cells improving fibrosis, regeneration, and function. *Hepatology* 53, 2003 (June, 2011).

19. J. K. Moore et al., Phenotypic and functional characterization of macrophages with therapeutic potential generated from human cirrhotic monocytes in a cohort study. *Cytotherapy* 17, 1604 (November, 2015).

20. D. S. Gilchrist, J. Ure, L. Hook, A. Medvinsky, Labeling of hematopoietic stem and progenitor cells in novel activatable EGFP reporter mice. *Genesis* 36, 168 (July, 2003).

21. H. U. Bergmeyer, P. Scheibe, A. W. Wahlefeld, Optimization of methods for aspartate aminotransferase and alanine aminotransferase. *Clin Chem* 24, 58 (January, 1978).

22. F. C. Pearlman, R. T. Lee, Detection and measurement of total bilirubin in serum, with use of surfactants as solubilizing agents. *Clin Chem* 20, 447 (April, 1974).

23. E. Frank, M. Hall, L. Trigg, G. Holmes, I. H. Witten, Data mining in bioinformatics using Weka. *Bioinformatics* 20, 2479 (Oct. 12, 2004).

24. J. Schindelin et al., Fiji: an open-source platform for biological-image analysis. *Nat Methods* 9, 676 (July, 2012).

25. C. A. Schneider, W. S. Rasband, K. W. Eliceiri, NIH Image to ImageJ: 25 years of image analysis. *Nat Methods* 9, 671 (July, 2012).

26. D. A. Ferenbach et al., Macrophages expressing heme oxygenase-1 improve renal function in ischemia/reperfusion injury. *Mol Ther* 18, 1706 (September, 2010).

27. L. Bosurgi et al., Vessel-associated myogenic precursors control macrophage activation and clearance of apoptotic cells. *Clin Exp Immunol* 179, 62 (January, 2015).28.

C. C. Bain et al., Long-lived self-renewing bone marrow-derived macrophages displace embryo-derived cells to inhabit adult serous cavities. *Nat Commun* 7, ncomms11852 (2016).

29. D. J. Antoine et al., Mechanistic biomarkers provide early and sensitive detection of acetaminophen-induced acute liver injury at first presentation to hospital. *Hepatology* 58, 777 (August, 2013).

30. R. Parsa et al., Adoptive transfer of immunomodulatory M2 macrophages prevents type 1 diabetes in NOD mice. *Diabetes* 61, 2881 (November, 2012).

31. M. Nishida et al., Adoptive transfer of macrophages ameliorates renal fibrosis in mice. *Biochem Biophys Res Commun* 332, 11 (Jun. 24, 2005).

32. T. Suzuki et al., Pulmonary macrophage transplantation therapy. *Nature* 514, 450 (Oct. 23, 2014).

33. R. Andreesen et al., Adoptive transfer of tumor cytotoxic macrophages generated in vitro from circulating blood monocytes: a new approach to cancer immunotherapy. *Cancer Res* 50, 7450 (Dec. 1, 1990).

34. Y. Ito, E. R. Abril, N. W. Bethea, R. S. McCuskey, Role of nitric oxide in hepatic microvascular injury elicited by acetaminophen in mice. *American Journal of Physiology-Gastrointestinal and Liver Physiology* 286, G60 (18 Dec. 2012, 2004).

35. P. Scaffidi, T. Misteli, M. E. Bianchi, Release of chromatin protein HMGB1 by necrotic cells triggers inflammation. *Nature* 418, 191 (28 Sep. 2012, 2002).

36. C. G. Antoniades et al., Source and characterization of hepatic macrophages in acetaminophen-induced acute liver failure in humans. *Hepatology* 56, 735 (August, 2012).

37. L. P. James et al., Elevation of serum interleukin 8 levels in acetaminophen overdose in children and adolescents. *Clin Pharmacol Ther* 70, 280 (September, 2001).

38. Y. Ito, N. W. Bethea, E. R. Abril, R. S. McCuskey, Early hepatic microvascular injury in response to acetaminophen toxicity. *Microcirculation* 10, 391 (October, 2003).

39. Y. Ito, E. R. Abril, N. W. Bethea, R. S. McCuskey, Role of nitric oxide in hepatic microvascular injury elicited by acetaminophen in mice. *Am J Physiol Gastrointest Liver Physiol* 286, G60 (January, 2004).

40. K. Alasoo et al., Transcriptional profiling of macrophages derived from monocytes and iPS cells identifies a conserved response to LPS and novel alternative transcription. *Sci Rep* 5, 12524 (2015).

41. N. Lachmann et al., Large-scale hematopoietic differentiation of human induced pluripotent stem cells provides granulocytes or macrophages for cell replacement therapies. *Stem Cell Reports* 4, 282 (Feb. 10, 2015).

42. H. Zhang et al., Functional analysis and transcriptomic profiling of iPSC-derived macrophages and their application in modeling Mendelian disease. *Circ Res* 117, 17 (Jun. 19, 2015).

43. Dreymueller, D. et al. Embryonic stem cell-derived M2-like macrophages delay cutaneous wound healing. *Wound Repair and Regeneration* 21, 44-54, doi:10.1111/j.1524-475X.2012.00858.x (2016).

44. Hume, D. A. & MacDonald, K. P. Therapeutic applications of macrophage colony-stimulating factor-1 (CSF-1) and antagonists of CSF-1 receptor (CSF-1R) signaling. *Blood* 119, 1810-1820, doi:10.1182/blood-2011-09-379214 (2012).

45. Klimchenko, O. et al. Monocytic cells derived from human embryonic stem cells and fetal liver share common differentiation pathways and homeostatic functions. *Blood* 117, 3065-3075, doi:10.1182/blood-2010-07-295246 (2011).

The invention claimed is:

1. A method of preventing or treating liver injury in a subject, comprising administering a therapeutically effective amount of alternatively-activated macrophages to said subject.

2. The method of claim 1, wherein the livery injury is an acute liver injury.

3. The method of claim 1 wherein the subject has or is suspected of having taken an overdose of one or more drugs selected from the group consisting of: acetaminophen, clarithromycin, statins, nicotinic acid, amiodarone, methotrexate, isoniazid, nitrofurantoin, augmentin, asprin, indomethacin, ibuprofen, naproxen, piroxicam, nabumetone, diclofenac, tacrine or disulfiram.

4. The method of claim 3, wherein the drug is acetaminophen.

5. The method of claim 3, wherein the alternatively-activated macrophages is administered at least 10 hours after the drug.

6. The method of claim 1, wherein the alternatively-activated macrophages are obtained by polarising macrophages with IL-4, IL-13, CSF-1 or any combination thereof.

7. The method of claim 1, wherein the macrophages are bone-marrow derived macrophages.

8. The method of claim 1, wherein alternatively-activated macrophages are autologous to the subject having a liver injury.

9. The method of claim 1, wherein the administration is intravenous.

10. The method of claim 1, wherein the alternatively-activated macrophages are provided at a dose of $1\times10^7$ to $1\times10^9$ cells.

11. The method of claim 1, wherein the alternatively-activated macrophages are derived from pluripotent stem cells, such as induced pluripotent stem cells or embryonic stem cells.

* * * * *

UNITED STATES PATENT AND TRADEMARK OFFICE
CERTIFICATE OF CORRECTION

PATENT NO. : 11,285,174 B2
APPLICATION NO. : 16/331787
DATED : March 29, 2022
INVENTOR(S) : Forbes et al.

Page 1 of 1

It is certified that error appears in the above-identified patent and that said Letters Patent is hereby corrected as shown below:

On the Title Page

Item (30) Foreign Application Priority Data: Please correct "1615923" to read -- 1615923.8 --

Item (30) Foreign Application Priority Data: Please correct "1707183" to read -- 1707183.8 --

In the Specification

Column 7, Lines 60-61: Please remove the paragraph break between "(G) and" and "ESDMs"

In the Claims

Column 45, Line 6, Claim 2: Please correct "livery" to read -- liver --

Signed and Sealed this
Thirteenth Day of September, 2022

Katherine Kelly Vidal
*Director of the United States Patent and Trademark Office*